(12) United States Patent
Fischetti et al.

(10) Patent No.: US 9,404,922 B2
(45) Date of Patent: Aug. 2, 2016

(54) RECOMBINANT PHAGES AND PROTEINS

(71) Applicant: The Rockefeller University, New York, NY (US)

(72) Inventors: Vincent Fischetti, New York, NY (US); Raymond Schuch, New York, NY (US); Sherry Kan, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/332,060

(22) Filed: Jul. 15, 2014

(65) Prior Publication Data

US 2016/0018397 A1    Jan. 21, 2016

Related U.S. Application Data

(60) Provisional application No. 61/846,287, filed on Jul. 15, 2013.

(51) Int. Cl.
| | |
|---|---|
| *C12Q 1/00* | (2006.01) |
| *G01N 33/53* | (2006.01) |
| *G01N 33/554* | (2006.01) |
| *G01N 33/567* | (2006.01) |
| *G01N 33/569* | (2006.01) |
| *C07K 14/005* | (2006.01) |
| *C12N 7/00* | (2006.01) |
| *G01N 21/64* | (2006.01) |

(52) U.S. Cl.
CPC ........ *G01N 33/56911* (2013.01); *C07K 14/005* (2013.01); *C12N 7/00* (2013.01); *G01N 21/6486* (2013.01); *C12N 2795/10031* (2013.01); *G01N 2333/705* (2013.01)

(58) Field of Classification Search
CPC .............................................. G01N 33/56911
See application file for complete search history.

(56) References Cited

U.S. PATENT DOCUMENTS

| | | | |
|---|---|---|---|
| 5,445,934 | A | 8/1995 | Fodor et al. |
| 5,653,939 | A | 8/1997 | Hollis et al. |
| 5,667,667 | A | 9/1997 | Southern |
| 5,929,208 | A | 7/1999 | Heller et al. |
| 6,093,302 | A | 7/2000 | Montgomery |
| 6,280,595 | B1 | 8/2001 | Montgomery |
| 6,444,111 | B1 | 9/2002 | Montgomery |
| 2012/0021454 | A1* | 1/2012 | Bikker et al. ........... 435/34 |

OTHER PUBLICATIONS

Kan et al (Journal of Bacteriology vol. 195, No. 19, pp. 4355-4364, Oct. 2013).*
Abshire et al., Production and Validation of the Use of Gamma Phage for Identification of Bacillus anthracis, J. Clin. Microbiol., Sep. 2005, pp. 4780-4788. Sep. 1, 2005.
Ackermann et al., Partial characterization of a cubic Bacillus phage, Can. J. Microbiol., vol. 24, 1978, pp. 986-993. Sep. 1, 1978.
Bamford et al., Evolution of Viral Structure, Tehoretical Population Biology, 61, 461-470 (2002), pp. 461-470. Jan. 1, 2002.
Bamford et al., A New Mutant Class, Made by Targeted Mutagenesis, of Phage PRD1 Reveals That Protein P5 Connects the Receptor Binding Protein to the Vertex, J. Virol., Sep. 2000, pp. 7781-7786. Jan. 1, 2000.
Bamford et al., Genome Organization of Membrane-Containing Bacteriophage PRD1, Virology 193, 658-676 (1991). Jan. 1, 1991.
Bamford et al., Large-Scale Purification of Membrane-Containing Bacteriophage PRD1 and Its Subviral Particles, Virology 181, 348-352 (1991). Jan. 1, 1991.
Benson et al., The X-ray crystal structure of P3, the major coat protein of the lipid-containing bacteriophage PRD1, at 1.65A resolution, Acta Cryst. (2002), D58, 39-59. Jan. 1, 2002.
Bishop-Lilly et al., Whole genome sequencing of phage resistant Bacillus anthracis mutants reveals an essential role for cell surface anchoring protein CsaB in phage AP50c adsorption, Virology Journal 2012, 9:246. Jan. 1, 2012.
CDC, Anthraz FAQ: Diagnosis, http://www.bt.cdc.gov/agent/anthrax/faq/diagnosis.asp. Nov. 25, 2002.
Daugelavicius et al., Changes in Host Cell Energetics in Response to Bacteriophage PRD1 DNA Entry, J. Bacteriol. vol. 179 (1997), pp. 5203-5210. Aug. 1, 1997.
Gaidelyte et al., The Entry Mechanism of Membrane-Containing Phage Bam35 Infecting Bacillus thuringiensis, J. Bacteriol. Aug. 2006, vol. 188, No. 16, pp. 5925-5937. Aug. 1, 2006.
Gao et al., In Situ Synthesis of Oligonucleotide Microarrays, Biopolymers 73: 579-596 (2004). Mar. 10, 2004.
Grahn et al., Stable Packaging of Phage PRD1 DNA Requires Adsorption Protein P2, Which Binds to the IncP Plasmid-Encoded Conjugative Transfer Complex, J. Bacteriol., vol. 181, No. 21, Nov. 1999, pp. 6689-6696. Nov. 1, 1999.
Grahn et al., Sequential model of phage PRD1 DNA delivery: active involvement of the viral membrane, Molecular Microbiology (2002) 46(5), 1199-1209. Jan. 1, 2002.
Haywood, Virus Receptors: Binding, Adhesion Strengthening, and Changes in Viral Structure, J. Virology, Jan. 1994, vol. 68, No. 1, pp. 1-5. Jan. 1, 1994.
Huiskonen et al., Tale of two spikes in bacteriophage PRD1, PNAS, vol. 114, No. 16, pp. 6666-6671. Apr. 17, 2007.
Jacobson et al., Adsorption of Bacteriophages phi29 and 22a to Protoplasts of Bacillus subtilis 168, J. Virology, Mar. 1977, vol. 21, No. 3, pp. 1223-1227. Mar. 1, 1977.
Laurinmaki et al., Membrane Proteins Modulate the Bilayer Curvature in the Bacterial Virus Bam35, Structure, vol. 13, 1819-1828, Dec. 2005. Dec. 1, 2005.
Merckel et al., The Structure of the Bacteriophage PRD1 Spike Sheds Light on the Evolution of Viral Capsid Architecture, Molecular Cell., vol. 18, 161-170. Apr. 15, 2005.
Mignot et al., Development switch of S-layer protein synthesis in Bacillus anthracis, Molecular Microbiology (2002) 43(6), 1615-1627. Jan. 1, 2002.

(Continued)

*Primary Examiner* — Albert Navarro
(74) *Attorney, Agent, or Firm* — Hodgson Russ LLP

(57) ABSTRACT

The present disclosure provides recombinant phages, a Wip1 p23 receptor binding protein and a Wip1 p24 receptor binding protein that bind to *Bacillus anthracis*. The disclosure further provides methods and uses thereof.

4 Claims, 8 Drawing Sheets
(5 of 8 Drawing Sheet(s) Filed in Color)

(56) References Cited

OTHER PUBLICATIONS

Mindich et al., Assembly of Bacteriophage PRD1: Particle Formation with Wild-Type and Mutant Viruses, J. Virology, Dec. 1982, vol. 44, No. 3, pp. 1021-1030. Dec. 1, 1982.

Monteville et al., Lactococcal Bacteriophages Require a Host Cell Wall Carbohydrate and a Plasma Membrane Protein for Adsorption and Ejection of DNA, Applied and Environmental Microbiology, Sep. 1994, vol. 60, No. 9, pp. 3204-3211. Sep. 1, 1994.

Nagy et al., Characteristics of Phage AP50, an RNA Phage Containing Phospholipids, J. gen. Virol. (1976), 32, 129-132. Jan. 1, 1976.

Olsen et al., Characteristics of PRD1, a Plasmid-Dependent Broad Host Range DNA Bacteriophage, J. Virology, Sep. 1974, vol. 14, No. 3, pp. 689-699. Jan. 1, 1974.

Ravantti et al., Comparative analysis of bacterial viruses Bam35, infecting a gram-positive host, and PRD1, infecting gram-negative hosts, demonstrates a viral lineage, Virology 313 (2003) 401-414. Jan. 1, 2003.

Raz et al., Sortase A localizes to distinct foci on the *Streptococcus pyogenes* membrane, PNAS, Nov. 26, 2008, vol. 105, No. 47, pp. 18549-18554. Nov. 25, 2008.

Rydman et al., Bacteriophage PRD1 Contains a Labile Receptor binding Structure at Each Vertex, J. Mol. Biol. (1999) 291, 575-587, Jan. 1, 1999.

Rydman et al., A Minor Capsid Protein P30 is Essential for Bacteriophage PRD1 Capsid Assembly, J. Mol. Biol. (2001) 313, 785-795. Jan. 1, 2001.

Schuch et al., Prevalence of Bacillus anthracis-Like Organisms and Bacteriophages in the Intestinal Tract of the Earthworm *Eisenia fetida*, Applied and Environmental Microbiology, Apr. 2010, vol. 76, No. 7, pp. 2286-2294. Apr. 1, 2010.

Schuch et al., The Secret Life of the Anthrax Agent Bacillus anthracis: Bacteriophage-Mediated Ecological Adaptations, PLoS One, Aug. 2009, vol. 4, Issue 8, e6532 Aug. 12, 2009.

Schuch et al., Detailed Genomic Analysis of the W(beta) and lambda Phages Infecting Bacillus anthracis: Implications for Evolution of Environmental Fitness and Antibiotic Resistance, J. of Bacteriology, Apr. 2006, vol. 188, No. 8, pp. 3037-3051. Apr. 1, 2006.

Schuch et al., A bacteriolytic agent that detects and kills Bacillus anthracis, Nature, vol. 418, pp. 884-889. Aug. 22, 2002.

Sokolova et al., Solution Structure of Bacteriophage PRD1 Vertex Complex, J. Biological Chemistry, vol. 276, No. 49, pp. 46187-46195 (2001). Dec. 7, 2001.

Sozhamannan et al., Molecular Characterization of a Variant of Bacillus anthracis-Specific Phage AP50 with Improved Bacteriolytic Activity, Applied and Environmental Microbiology, No. 2008, vol. 74, No. 21, pp. 6792-6796. Nov. 1, 2008.

Stromsten et al., The Bacillus thuringiensis Linear Double-Stranded DNA Phage Bam35, Which Is Highly Similar to the Bacillus cereus Linear Plasmid pBClin15, Has a Prophage State, J. of Bacteriol., Dec. 2003, vol. 185, No. 23, pp. 6985-6989. Dec. 1, 2003.
Uniprot, P27587, www.uniprot.org/uniprot/P27587.txt Aug. 1, 1992.
Uniprot, P27388, www.uniprot.org/uniprott/P27388.txt Aug. 1, 1992.
Verheust et al., GIL16, a New Gram-Positive Tectiviral Phage Related to the Bacillus thuringiensis GIL01 and the Bacillus cereus pBClin15 Elements, J. Bacteriology, Mar. 2005, vol. 187, No. 6, pp. 1966-1973. Mar. 1, 2005.
Xu et al., The Receptor Binding Protein P2 of PRD1, a Virus Targeting Antibiotic-Resistant Bacteria, Has a Novel Fold Suggesting Multiple Functions, Structure, vol. 11, pp. 309-322. Mar. 1, 2003.

* cited by examiner

RECOMBINANT PHAGES AND PROTEINS

CROSS REFERENCE TO RELATED APPLICATIONS

This application claims priority to U.S. Provisional Application No. 61/846,287, filed on Jul. 15, 2013, the disclosure of which is incorporated herein by reference.

GOVERNMENT FUNDING

This invention was made with government support under Grant AI057472 awarded by USPHS. The government has certain rights in the invention.

FIELD OF THE INVENTION

The invention relates to bacteriophages that inhibit the growth of Gram positive and Gram negative bacterial cells. These bacteriophages are useful to identify and treat pathogenic bacteria.

BACKGROUND OF THE INVENTION

Bacteriophage-based diagnostics and therapeutics have been recognized as tools to combat bacterial infections for nearly a century. Wip1 (for worm intestinal phage 1) is a recently identified phage that infects the pathogen *Bacillus anthracis* and was isolated from the intestinal tract of *Eisenia fetida* worms [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94]. It is a tailless, double-stranded DNA phage possessing an internal lipid membrane beneath an icosahedral protein coat [Schuch, R. F. V. A., *The Secret Life of the Anthrax Agent Bacillus Anthracis: Bacteriophage-Mediated Ecological Adaptations*. PLos One, 2009. 4(8): p. e6532]. These features indicate that Wip1 belongs to the family Tectiviridae, a relatively rare phage group with surprising structural similarity to and a proposed evolutionary lineage with the mammalian adenovirus [Merckel, M. C. H., J. T.; Bamford, D. H.; Goldman, A.; Tuma, R., *The Structure of the Bacteriophage PRD1 Spike Sheds Light on the Evolution of Viral Capsid Architecture*. Molecular Cell, 2005. 18: p. 161-170, Bamford, D., *Evolution of Viral Structure*. Theoretical Population Biology, 2002. 61(4): p. 461-470.]. The Tectiviridae family consists of six isolates that infect gram-negative bacteria, including PRD1 [Olsen, R. H. S., J.; Gray, R. H., *Characteristics of PRD1, a Plasmid-Dependent Broad Host Range DNA Bacteriophage*. Journal of Virology, 1974. 14(3): p. 689-699], and six that infect gram-positive bacteria, including Bam35, Gil16, AP50, and Wip1 [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94; Ackermann, H. W. R., R.; Martin, M.; Murthy, M. R.; Smirnoff, W. A., *Partial Characterization of a Cubic Bacillus Phage*. Canadian Journal of Microbiology, 1978. 24: p. 986-993; Verheust, C., N. Fornelos, and J. Mahillon, *GIL16, a new gram positive tectiviral phage related to the Bacillus thuringiensis GIL01 and the Bacillus cereus pBClin15 elements*. Journal of bacteriology, 2005. 187(6): p. 1966-73; Nagy, E. P., B.; Ivanovics, G., *Characteristics of Phage AP50, an RNA Phage Containing Phospholipids*. Journal of General Virology, 1976. 32: p. 129-132]. While PRD1 has been studied in detail, tectiviruses that infect gram-positive bacteria are not as well characterized.

Wip1 phage exhibits a very narrow host range and is highly specific to *B. anthracis* [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94], the notorious biothreat agent and gram-positive bacterium that causes anthrax disease. The current gold standard for identifying suspected *B. anthracis* involves testing for γ phage sensitivity [Abshire, T. G., J. E. Brown, and J. W. Ezzell, *Production and validation of the use of gamma phage for identification of Bacillus anthracis*. Journal of clinical microbiology, 2005. 43(9): p. 4780-8; *Anthrax Q & A: diagnosis*. 2002; Available from: www.bt.cdc.gov/agent/anthrax/faq/diagnosis.asp]. However, using γ as a diagnostic tool can lead to false positives due to the susceptibility of several *Bacillus cereus* strains to infection by this phage [Schuch, R. and V. A. Fischetti, *Detailed genomic analysis of the Wbeta and gamma phages infecting Bacillus anthracis: implications for evolution of environmental fitness and antibiotic resistance*. Journal of bacteriology, 2006. 188(8): p. 3037-51; Schuch, R. N., D.; Fischetti, V. A., *A bacteriolytic agent that detects and kills Bacillus anthracis*. Nature, 2002. 418: p. 884-889]. Recent studies have shown that the host range of γ is less specific to *B. anthracis* than those of tectiviruses Wip1 and AP50 [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94; Sozhamannan, S., et al., *Molecular Characterization of a Variant of Bacillus anthracis-Specific Phage AP50 with Improved Bacteriolytic Activity*. Applied and environmental microbiology, 2008. 74(21): p. 6792-6796]. For example, *Bacillus cereus* ATCC 4342 is sensitive to infection by γ phage but not to infection by either Wip1 or AP50. Additionally, the γ diagnostic phage yields plaques on *B. anthracis* ΔSterne only after 5 days, whereas Wip1 plaques can be detected after just 12 hours post infection [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94].

Wip1's high specificity to *B. anthracis* is likely mediated by the initial recognition and binding of the virus to the host cell. Receptor binding proteins on the phage coat interact very specifically with receptors exposed on the surface of the bacterium [Haywood, A. M., *Virus receptors: binding, adhesion strengthening, and changes in viral structure*. Journal of virology, 1994. 68(1): p. 1-5]. For tectiviruses, the receptor binding protein assembles with other phage proteins into a protruding complex that extends from each particle vertex [Sokolova, A., et al., *Solution structure of bacteriophage PRD1 vertex complex*. The Journal of biological chemistry, 2001. 276(49): p. 46187-95]. In the PRD1 spike complex, two elongated proteins, monomeric receptor binding protein P2 and trimeric spike protein P5, form two separate spikes that each protrude from penton base protein P31 [Bamford, J. K. B., D. H., *A New Mutant Class, Made by Targeted Mutagenesis, of Phage PRD1 Reveals That Protein P5 Connects the Receptor Binding Protein to the Vertex*. Journal of virology, 2000. 74(17): p. 7781-7786; Huiskonen, J. T., V. Manole, and S. J. Butcher, *Tale of two spikes in bacteriophage PRD1*. Proceedings of the National Academy of Sciences of the United States of America, 2007. 104(16): p. 6666-71; Mindich, L. B., D.; McGraw, T.; Mackenzie, G, *Assembly of bacteriophage PRD1: particle formation with wild-type and

*mutant viruses.* Journal of virology, 1982. 44(3): p. 1021-1030; Xu, L. B., S. D.; Butcher, S. J.; Bamford, D. H.; Burnett, R. M., *The Receptor Binding Protein P2 of PRD1, a Virus Targeting Antibiotic-Resistant Bacteria, Has a Novel Fold Suggesting Multiple Functions.* Structure, 2003. 11: p. 309-322].

Spike complex protein components have also been identified for Bam35, a tectivirus that infects gram-positive *Bacillus thuringiensis* [Gaidelyte, A., et al., *The Entry Mechanism of Membrane-Containing Phage Bam35 Infecting Bacillus thuringiensis.* Journal of bacteriology, 2006. 188(16): p. 5925-5934]. By threading Bam35 gene products onto PRD1 X-ray structures, it was determined that gp28 is homologous to spike protein P5 and that gp29 is homologous to the C-terminal half of receptor binding protein P2 [Laurinmaki, P. A. H., J. T.; Bamford, D. H.; Butcher, S. J., *Membrane Proteins Modulate the Bilayer Curvature in the Bacterial Virus Bam35.* Structure, 2005. 13: p. 1819-1828; Ravantti, J. J. G., A.; Bamford, D. H.; Bamford, J. K., *Comparative analysis of bacterial viruses Bam35, infecting a gram positive host, and PRD1, infecting gram-negative hosts, demonstrates a viral lineage.* Virology, 2003. 313: p. 401-414. In addition, gp28 and gp29 were determined to reside on the surface of Bam35 from phage aggregation and neutralization assays using polyclonal antibodies [Gaidelyte, A., et al., *The Entry Mechanism of Membrane-Containing Phage Bam35 Infecting Bacillus thuringiensis.* Journal of bacteriology, 2006. 188(16): p. 5925-5934]. However, competitive binding assays using both recombinant and dissociated surface proteins were inconclusive, and a Bam35 receptor binding protein could not be identified.

The described invention addresses these problems, and provides recombinant phage proteins, and uses thereof, to identify and treat pathogenic bacteria.

SUMMARY OF THE INVENTION

The described invention provides a recombinant protein composition comprising Wip1 p23 receptor binding protein, variants or fragments thereof. The invention further provides a Wip1 p24 receptor binding protein, variants or fragments thereof. The invention further provides a Wip1 p23 receptor binding protein that further comprises a reporter molecule. The invention further provides a reporter molecule that is a fluorophore, a fluorophore/quencher pair, an antibody, a llama-body, an isotope, or combinations thereof. The invention further provides a Wip1 p23 receptor binding protein that is capable of binding *Bacillus anthracis*. The invention further provides a recombinant protein composition further comprising a substrate. The described invention further provides a native or recombinant Wip1 bacteriophage having affinity for and lytic activity against *Bacillus anthracis*. The invention further provides a bacteriophage that further comprises a recombinant detectable element, a regulatory element, reporter, or combinations thereof. Furthermore, the described invention provides a recombinant protein composition that comprises the native or recombinant Wip1 bacteriophage having affinity for and lytic activity against *Bacillus anthracis*.

The described invention further provides a system for detecting *Bacillus anthracis* comprising a recombinant protein composition where the recombinant protein combination contains at least one of a Wip1 p23 receptor binding protein, variants or fragments thereof, a Wip1 p24 receptor binding protein, variants or fragments thereof, a native or recombinant Wip1 bacteriophage having affinity for and activity against *Bacillus anthracis*, or combinations thereof, and a detector in communication with said recombinant protein composition, wherein the detector is capable of detecting a signal generated upon recognition of a *Bacillus anthracis* receptor by recombinant protein composition. The invention further provides the system further comprising a light source in optical communication with the recombinant protein composition. The invention further provides the system further comprising a processor for processing signals detected by the detector.

The described invention further provides a method of identifying or detecting *Bacillus anthracis* in a sample, the method comprising: (a) providing a sample suspected of containing *Bacillus anthracis*; (b) contacting the sample with a recombinant protein composition where the recombinant protein combination contains at least one of a Wip1 p23 receptor binding protein, variants or fragments thereof, a Wip1 p24 receptor binding protein, variants or fragments thereof, a Wip1 native or recombinant bacteriophage having affinity for and activity against *Bacillus anthracis*, or combinations thereof, wherein a change in a signal generated by a reporter molecule indicates the presence of *Bacillus anthracis* in the sample. The invention further provides the method wherein the sample is a biological sample or environmental sample. The invention further provides the method wherein the reporter molecule is a fluorophore or flurophore/quencher pair. The invention further provides the method wherein the recombinant protein composition changes conformation when contacting a *Bacillus anthracis* receptor thereby changing detectable properties of the recombinant protein composition.

The described invention further provides an isolated nucleic acid encoding a Wip1 p23 receptor binding protein, a Wip1 p24 receptor binding protein, a variant thereof, or combination thereof, wherein the Wip1 p23 receptor binding protein, Wip1 p24 receptor binding protein, variants or combinations thereof bind to *Bacillus anthracis*. The invention further provides the the isolated nucleic acid wherein the isolated nucleic acid is operably linked to a regulatory element, reporter, a detectable element, or combinations thereof. The invention further provides the isolated nucleic acid wherein the isolated nucleic acid is a cDNA.

The described invention further provides a recombinant expression vector comprising the inventive isolated nucleic acids.

The described invention further provides a recombinant expression composition comprising the inventive recombinant expression vector. The invention further provides the recombinant expression composition wherein the recombinant expression composition further comprises a detectable element.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

His-p22 (blue) and his-p24 (green) did not affect phage activity. Bars represent standard error for a minimum of 3 experiments. B) Anti-his-p23 antibody neutralization of Wip1 activity. Polyclonal antibodies were generated against his-p23 and tested for neutralization of Wip1 activity using methods described. After preincubation with phage, anti-his-p23 (closed circles) inhibited Wip1 adsorption to $B.$ $anthracis$ ΔSterne by up to 90% in a dose-dependent manner. Pre-bleed serum (open circles) did not affect Wip1 adsorption activity. Bars represent standard error of at least 3 experiments.

Figure 5:
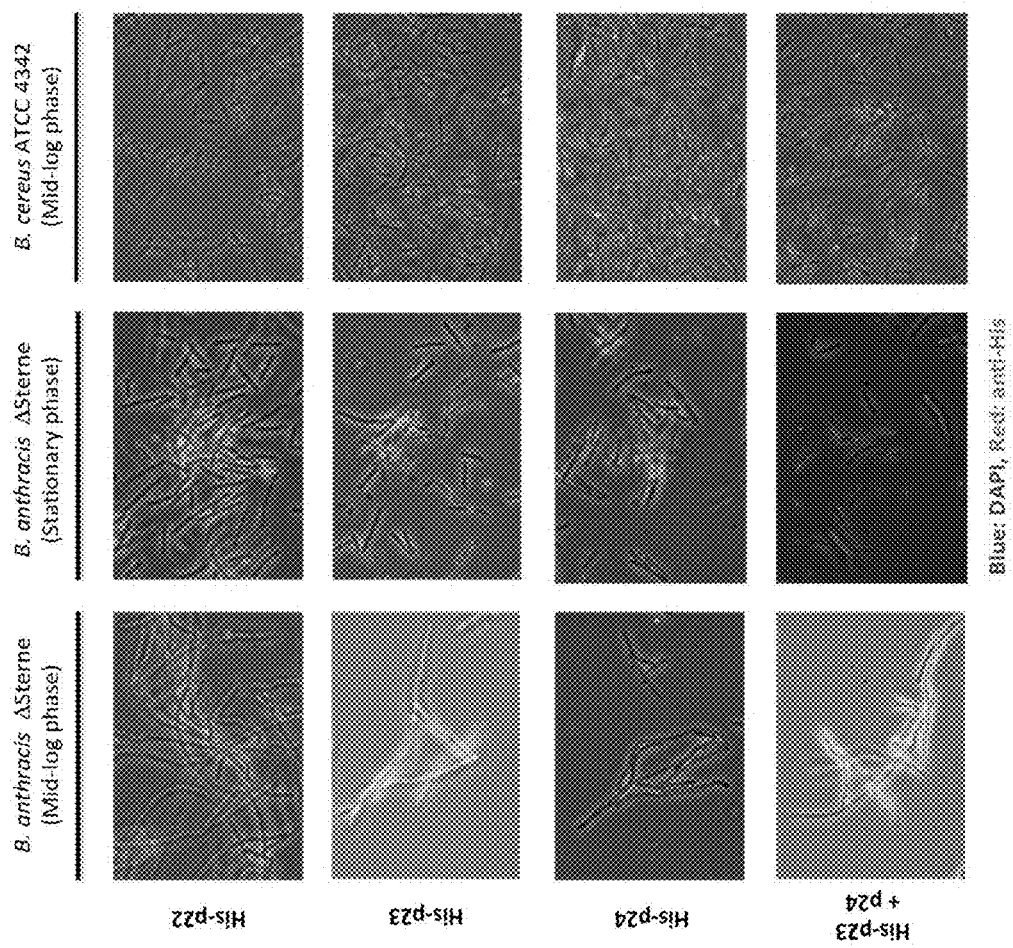

FIG. 5 shows indirect immunofluorescence microscopy using his-tagged Wip1 proteins. 1000× magnification.

Figure 6:
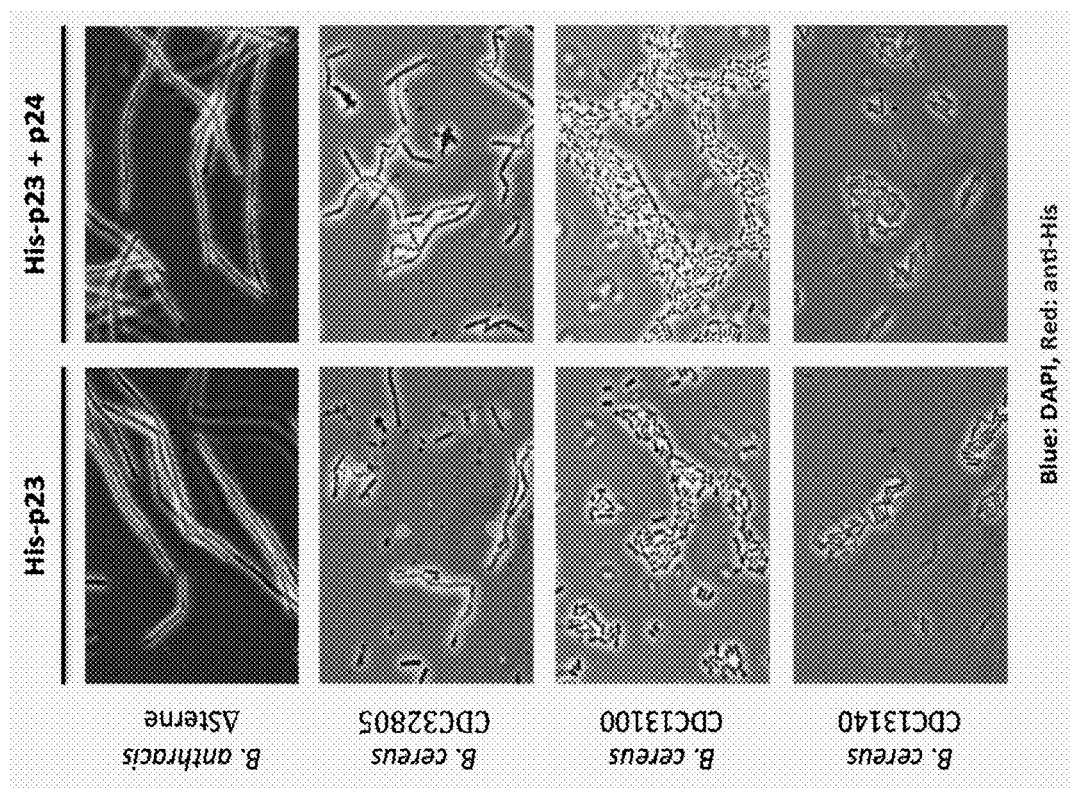

FIG. 6 shows indirect immunofluorescence microscopy using his-p23 and the his-p23+p24 complex. 1000× magnification.

Figure 7:
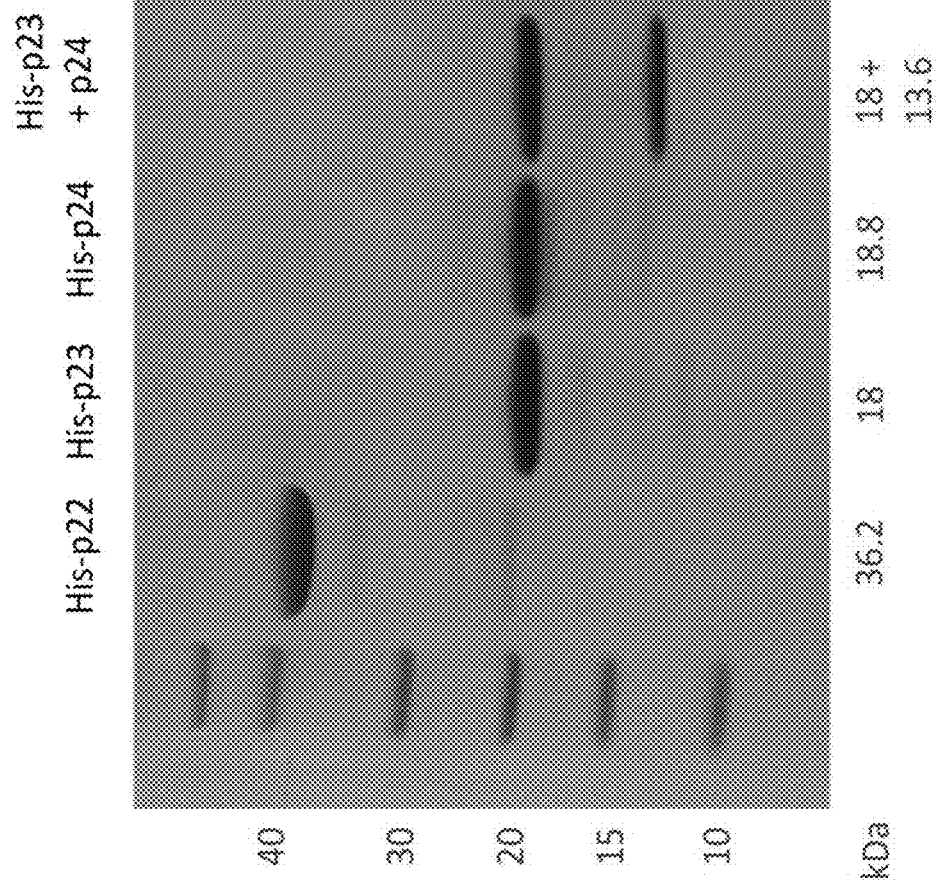

FIG. 7. Following expression and purification methods as described, the recombinant his-tagged Wip1 proteins were then measured using standard BSA assays. Protein solutions were diluted to concentrations of 250 µg/ml for single protein samples (his-p22; his-p23; his-p24) and 500 µg/ml for co-expressed protein samples (his-p23+p24). SDS-PAGE analysis of these protein samples revealed purification to near homogeneity. The samples shown here are the exact samples used in the following protein overlay-based inhibition assays.

DETAILED DESCRIPTION OF THE INVENTION

The described invention provides a better understanding of Wip1's highly specific tropism for $B.$ $anthracis$. We started by imaging the morphological changes of Wip1 phage upon adsorption, expanding its host range analysis with adsorption studies, and sequencing its viral genome. Based on genomic analysis with other gram-positive infecting tectiviruses, candidate gene products for the Wip1 spike complex were predicted and used to identify a Wip1 receptor binding protein that detects and exhibits specificity for $B.$ $anthracis$.

In the described invention, we characterized the Wip1 phage and its genome to develop the tools to identify the Wip1 gene product 23 as a receptor binding protein. Wip1 tropism was previously shown to be highly specific to $B.$ $anthracis$. Here, we determined with adsorption assays that specificity to $B.$ $anthracis$ is mediated by Wip1's receptor binding. Indeed, receptor binding protein p23 was demonstrated to bind very specifically to bacterial strains that correspond with Wip1's narrow host range.

The identification of Wip1 p23 as a receptor binding protein shows that it is a unique protein with no homology to any other known proteins. Additionally, ORF23 shares no sequence identity with AP50, a tectivirus with a similar host range that is also highly specific to $B.$ $anthracis$. Genomic analysis showed that the overall Wip1 genome shares significant similarities to the AP50 genome in ORF size, sequence, and organization. In fact, the genes neighboring ORF23 display this conservation. ORF22 (291 residues) shares 64% sequence identity with AP50 ORF27 (304 residues) and ORF24 (118 residues) shares 51% sequence identity with AP50 ORF29 (118 residues).

AP50 ORF28, which is located in the corresponding genomic position to Wip1 ORF23, is the gene that harbors one of two sequence mutations that differentiates isolate AP50t, which produces turbid plaques, from isolate AP50c, which produces clear plaques. Generally, clear plaques are formed when the host is completely susceptible to the phage while turbid plaques are formed if the host is partially resistant to the phage (for example, if 10% of the cells survive infection). Furthermore, AP50 ORF28 and Wip1 ORF23 are located at a highly variable region of their respective genomes. Although the Eip1 receptor-binding domain ORF23 exhibits sequence diversity, it was unexpected that two closely related tectiviruses with a similar host range have evolved uniquely different receptor binding proteins.

Additionally, it is shown that the his-p23 plus p24 complex exhibited higher competitive inhibition than his-p23 alone, suggesting that p24 complemented or enhanced his-p23 binding activity. This enhancement could result from simply protecting his-p23 proteins from degradation. However, we were careful to use fresh protein stocks in all assays. It also is possible that p24 could play a secondary but complementary role in Wip1 binding. The adsorption of phage to the gram-positive bacterial surface has been suggested to occur in two stages. The first step involves reversible binding to general recognition molecules in the cell wall and is followed by a subsequent irreversible step involving a more specific factor [Jacobson, E. D. L., O. E., $Adsorption$ $of$ $bacteriophages$ $phi$ $29$ $and$ $22a$ $to$ $protoplasts$ $of$ $Bacillus$ $substilis$. Journal of virology, 1977. 21(3): p. 1223-1227; Monteville, M. R. A., B.; Geller, B. L., $Lactococcal$ $Bacteriophages$ $Require$ $a$ $Host$ $Cell$ $Wall$ $Carbohydrate$ $and$ $a$ $Plasma$ $Membrane$ $Protein$ $for$ $Adsorption$ $and$ $Ejection$ $of$ $DNA$. Applied and environmental microbiology, 1994. 60(9): p. 3204-3211]. In fact, the seahorse-like structure for PRD1 receptor binding protein P2 consists of multiple domains with different purported functions. In one P2 model, the fin-shaped domain is proposed to make initial contacts by scanning the host surface in order to bring the head domain closer to its receptor [Xu, L. B., S. D.; Butcher, S. J.; Bamford, D. H.; Burnett, R. M., $The$ $Receptor$ $Binding$ $Protein$ $P2$ $of$ $PRD1$, $a$ $Virus$ $Targeting$ $Antibiotic$-$Resistant$ $Bacteria$, $Has$ $a$ $Novel$ $Fold$ $Suggesting$ $Multiple$ $Functions$. Structure, 2003. 11: p. 309-322]. It is possible that Wip1 p24 is such a spike complex domain with non-specific, reversible surface scanning properties.

Polyclonal antibodies against his-p23 also were able to inactivate Wip1 binding activity. It should be noted, however, that the neutralizing effect of anti-his-p23 serum on Wip1 activity was much weaker compared to that of anti-gp28 or anti-gp29 serum on Bam35 activity [Gaidelyte, A., et al., $The$ $Entry$ $Mechanism$ $of$ $Membrane$-$Containing$ $Phage$ $Bam35$ $Infecting$ $Bacillus$ $thuringiensis$. Journal of bacteriology, 2006. 188(16): p. 5925-5934]. At a mere 20× dilution, anti-his-p23 antibody inactivation measured below 20%. In contrast, anti-gp28 and anti-29 antibodies did not demonstrate inactivation rates below 20% until they reached dilutions of 5,000× and 100,000×, respectively. One explanation for this difference is the possibility that p23 is a poor antigen that generated a weak immunogenic response. However, an indirect ELISA assay determined that the polyclonal antisera against his-p23 exhibited reasonable immunogenic strength (reading of Abs=1 at 1:2000 dilution).

The narrow infectivity and adsorption host range of Wip1 indicates that its receptor is unique to the exposed surface of $B.$ $anthracis$ and $B.$ $cereus$ CDC32805 in a manner that is accessible to phage. Indirect immunofluorescence microscopy demonstrated that p23 and the p23+p24 complex detect and label *B. anthracis* with a specificity that seems to match its narrow host range. This activity makes both the Wip1 phage and its receptor molecules useful diagnostic tools for *B. anthracis* with better specificity than the reagents currently being used.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; I=Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another: 1) Alanine (A), Serine (S), Threonine (T); 2) Aspartic Acid (D), Glutamic Acid (E); 3) Asparagine (N), Glutamic Acid (Q); 4) Arginine (R), Lysine (K); 5) Isoleucine (I), Leucine (L), Methionine (M), Valine (V); and 6) Phenylalanine (F), Tyrosine (Y), Tryptophan (W).

Accordingly, the described invention provides a recombinant protein composition comprising Wip1 p23 receptor binding protein or fragments thereof. Further, the recombinant protein composition also can include Wip1 p24 receptor binding protein or fragments thereof. The Wip1 p23 receptor binding protein can further include a reporter molecule or other detectable label or agent. Such reporter molecules or other detectable labels or agents include, for example, but are not limited to, a fluorophore, a fluorophore/quencher pair, an antibody, a llama-body, an isotope, or combinations thereof. Furthermore, the described invention provides a recombinant protein composition comprising a native or recombinant Wip1 bacteriophage.

The described invention further provides a recombinant protein composition attached or associated with a substrate.

A substrate includes a microfabricated solid surface to which molecules may be attached through either covalent or non-covalent bonds. This includes, but is not limited to, Langmuir-Bodgett films, functionalized glass, membranes, charged paper, nylon, germanium, silicon, PTFE, polystyrene, gallium arsenide, gold, and silver. Any other material known in the art that is capable of having functional groups such as amino, carboxyl, thiol or hydroxyl incorporated on its surface, is contemplated. This includes surfaces with any topology, such as spherical surfaces and grooved surfaces. Such recombinant protein compositions and substrates can be incorporated into a kit. Further, the recombinant protein composition can be attached or associated with a lateral flow test.

The described invention further provides an isolated nucleic acid encoding a Wip1 p23 receptor binding protein, or variant, where the Wip1 p23 receptor binding protein, or variant, binds to *Bacillus anthracis*. The isolated nucleic acid can further be operably linked to a regulatory element, reporter, or detectable element. The term "operably linked" refers to a functional linkage between a promoter and a second sequence, wherein the promoter sequence initiates and mediates transcription of the DNA sequence corresponding to the second sequence. Generally, "operably linked" means that the nucleic acid sequences being linked are contiguous and, where necessary to join two protein coding regions, are contiguous and in the same reading frame. Additionally, the described invention provides an isolated nucleic acid encoding a Wip1 p24 receptor binding protein, or variant, where the Wip1 p24 receptor binding protein increases the binding affinity of a Wip1 p23 receptor binding protein or variant to *Bacillus anthracis*. Furthermore, the isolated nucleic acid can be a cDNA. Additionally, the isolated nucleic acids can be encoded within a recombinant expression cassette. The described invention further provides a recombinant expression vector encoding at least one of a Wip1 p23 receptor binding protein, a Wip1 p24 receptor binding protein, or variants thereof. Such recombinant expression vectors can further encode a reporter or a detectable element, a regulatory sequence, a controllable regulatory element, or combinations thereof. The recombinant expression vectors can be included in recombinant expression compositions. Such recombinant expression compositions can include, but are not limited to, buffers, detectable reagents, and the like.

The inventive isolated nucleic acids, including cDNA, can be included in a microarray. Microarray preparation methods for making oligonucleotide probes for *Bacillus anthracis* identification include the following: (1) spotting a solution on a prepared surface using spotting robots; (2) in situ synthesis by printing reagents via ink jet or other computer printing technology and using phosphoramidite chemistry; (3) in situ parallel synthesis using electrochemically generated acid for removal of protecting groups and using standard phosphoramidite chemistry; (4) in situ synthesis using maskless photogenerated acid for removal of protecting groups and using regular phosphoramidite chemistry; (5) mask-directed in situ parallel synthesis using photo-cleavage of photolabile protecting groups (PLPG) and phosphoramidite chemistry; (6) maskless in situ parallel synthesis using PLPG and digital photolithography and standard phosphoramidite chemistry; and (7) electric field attraction/repulsion for depositing fully formed oligonucleotides onto known locations.

An electrode microarray for in situ oligo synthesis using electrochemical deblocking is disclosed in Montgomery U.S. Pat. Nos. 6,093,302; 6,280,595, and 6,444,111 (Montgomery I, II, and III respectively), all of which are incorporated by reference herein. Another and materially different electrode array (not a microarray) for in situ oligo synthesis on surfaces separate and apart from electrodes using electrochemical deblocking is disclosed in Southern U.S. Pat. No. 5,667,667, which is incorporated by reference herein. Photolithographic techniques for in situ oligo synthesis are disclosed in Fodor et al. U.S. Pat. No. 5,445,934 and the additional patents claiming priority thereto, all of which are incorporated by reference herein. Electric field attraction/repulsion microarrays are disclosed in Hollis et al. U.S. Pat. No. 5,653,939 and Heller et al. U.S. Pat. No. 5,929,208, both of which are incorporated by reference herein. A review of oligo microarray synthesis is provided by: Gao et al., *Biopolymers* 2004, 73:579.

The described invention further provides a system for detecting *Bacillus anthracis* comprising a recombinant protein composition and a detector in communication with the recombinant protein composition. The detector is capable of detecting a signal generated upon recognition of a *Bacillus anthracis* receptor by the recombinant protein composition. The system can further include a light source in optical communication with the recombinant protein composition. The system also can include a processor for processing signals detected by the detector.

The described invention further provides a method of identifying or detecting *Bacillus anthracis* in a sample, the method comprising: (a) providing a sample suspected of containing *Bacillus anthracis*; (b) contacting the sample with the recombinant protein composition, wherein a change in a signal generated by a reporter molecule indicates the presence of *Bacillus anthracis* in the sample. Such samples include, but are not limited to, a biological sample or environmental sample. The reporter molecule can be a detectable label or agent such as, but not limited to a fluorophore or flurophore/quencher pair. The recombinant protein composition can change conformation when contacting a *Bacillus anthracis* receptor thereby changing detectable properties of the recombinant protein composition.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Wip-1 Characterization

Bacterial Strains and Phages.

The majority of bacterial strains in the present study were previously described [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94; Schuch, R. F. V. A., *The Secret Life of the Anthrax Agent Bacillus Anthracis: Bacteriophage-Mediated Ecological Adaptations*. PLos One, 2009. 4(8): p. e6532; Schuch, R. N., D.; Fischetti, V. A., *A bacteriolytic agent that detects and kills Bacillus anthracis*. Nature, 2002. 418: p. 884-889]. All bacterial strains were grown in brain heart infusion (BHI) broth or agar plates at 30° C. according to standard protocols. The bacteriophage Wip1 was isolated from the intestinal tract of *Eisenia fetida* worms from Pennsylvania, USA. Phage propagation was performed on the *B. anthracis* ΔSterne strain.

Phage Propagation.

High titer phage stocks were obtained by infecting stationary cell cultures (100 ul) with 100 ul of a series of diluted (1:100 to 1:1000) Wip1 phage stocks. The phage-bacterium mixtures were incubated in a 37° C. water bath for 15 min and then plated with molten top agar (0.8%) onto BHI plates and incubated overnight at 30° C. When the viral plaques reached near confluency, the soft agar overlays were collected in conical tubes, incubated with 2 ml 10 mM K phosphate per plate for 15 min at room temperature, and centrifuged at 4,000 rpm for 20 min at 4° C. The resulting supernatants were filtered (0.45-um-pore-size-filter) and stored at 4° C.

Transmission Electron Microscopy.

Wip1 phages were incubated with overnight cultures of *B. anthracis* ΔSterne at a MOI of 10 for 5 minutes at 37° C. After incubation, the mixtures were transferred to a new Eppendorf tube with solidified agar on the bottom to act as a cushion during the subsequent centrifugation at 6000 rpm for 3 minutes. Supernatant was removed and the pellet was resuspended in 1× glutaraldehyde fixative. The TEM analyses were then performed at The Rockefeller University Bio-Imaging Resource Center as previously described [Schuch, R. N., D.; Fischetti, V. A., *A bacteriolytic agent that detects and kills Bacillus anthracis*. Nature, 2002. 418: p. 884-889].

Chloroform Sensitivity Assay.

Wip1 phage samples (2 ml) were incubated with and without various volumes of chloroform (up to 80 ul) in capped glass tubes with gentle mixing at room temperature for 15 min. The mixtures were then titered on *B. anthracis* ΔSterne. W2 phage with and without chloroform plated on *B. cereus* ATCC 4342 was used as a control.

Phage Adsorption Assay.

Various bacterial strains were grown to stationary phase (approximately $2 \times 10^8$ CFU/ml) and 100 ul of bacteria was mixed with 100 ul of Wip1 at $2 \times 10^7$ PFU/ml. The phage-bacterium mixtures were incubated in a 37° C. water bath for 20 min and then pelleted at 7,000 rpm for 3 min. The resulting supernatants were subsequently spin-filtered (Millipore; 0.22 um) and titered on plates of *B. anthracis* ΔSterne.

DNA Manipulation and Sequencing.

To obtain Wip1 DNA, Wip1 phage stocks ($1 \times 10^8$ CFU/ml) were lysed as follows: 25 μl of phage stock was suspended in 25 μl of 0.5M NaOH (Sigma-Aldrich), incubated for 5 minutes at room temperature, neutralized with 50 μl of Tris pH 8.0 (Life Technologies), and diluted in 450 μl dH$_2$0. Wip1 DNA was processed as described [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94] digested for 5 min at 65° C. with 0.1 units of Tsp509I (New England Biolabs), ligated to EcoRI adaptors (GeneLink), PCR amplified using adaptor-specific primers and cloned into the pBAD TOPO® TA expression vector (Life Technologies). The resulting plasmid library was transformed into One Shot TOP1O *E. coli* (Life Technologies), and random plasmid preparations were sequenced. Sequences derived from these transformed cells were confirmed by sequencing PCR products generated directly from Wip1 phage DNA. Primers were designed to sequence specific regions on the PCR products and unknown sequence regions were determined using primer walking on the purified Wip1 genome. GenBank Acession number KF188458.

Cloning of his-Tagged Wip1 ORFs 22, 23, and 24.

The PCR products containing the coding sequences for the Wip1 gene products 22, 23, and 24 were separately amplified using specific primers. Each DNA fragment was inserted into a modified CDFDuet-1 plasmid between the SalI-NotI sites preceded by a T7lac promoter and ribosome binding site as well as 2×His-tag sequences. Clones were confirmed by sequencing using primers that flank the insert.

Purification of his-Tagged Wip1 p22, p23, and p24.

Overnight cultures of *E. coli* DH5 alpha cells carrying the cloned constructs were diluted 1:100 and grown in LB medium with spectinomycin (20 ug/ml) for 4 h while shaking at 37° C. After being moved to 16° C., the cultures were induced with isopropyl-b-D-thiogalactopyranoside (IPTG) at a final concentration of 0.25 mM and shaken for an additional 18 h. Bacterial pellets were collected by centrifugation (Sorvall SLC-6000 rotor; 7200 rpm; 30 min; 4° C.) and resuspended in a cold buffer (50 mM Tris, pH 8.0+200 mM NaCl+5 mM imidazole) at 1/100 of the original culture volume. Bacterial lysis was conducted by multiple passages through a French pressure cell (at ~105 MPa) at 4° C. The cell debris was removed by centrifugation (Sorvall SS-34 rotor; 8,000 rpm; 20 min; 4° C.) followed by filtration (Nalgene; 0.45 um).

The following purification steps were conducted at room temperature using buffers kept at 4° C. 25 mL columns were loaded with 1.25 ml bed volume of Ni-NTA Agarose (Qiagen) and equilibrated with 2× column volumes of buffer (50 mM Tris, pH 8.0+200 mM NaCl+5 mM imidazole). The cell lysate from induced cultures was passed through the columns 2× using gravity flow. The Ni-NTA Agarose was then washed with 1× column volume of wash buffer A (50 mM Tris, pH 8.0+500 mM NaCl+30 mM imidazole) and 0.5× column volume of wash buffer B (50 mM Tris, pH 8.0+500 mM NaCl+60 mM imidazole). Finally, the eluate was collected by passing 5× bed volume of elution buffer (50 mM Tris, pH 8.0+500 mM NaCl+250 mM imidazole) through the column.

In preparation for the next step of the purification process, the eluted proteins were dialyzed against buffer A (20 mM phosphate buffer; pH 7.4) at 4° C. Ion exchange chromatography was then conducted using a 5 mL HiTrap Q HF column at a linear gradient from 100% Buffer A targeting 50% Buffer B (20 mM phosphate buffer+1M NaCl; pH 7.4). Fractions containing the purified proteins of interest were collected, analyzed by SDS-PAGE, pooled, and dialyzed against 1×PBS at 4° C. (FIG. 7).

Cloning and Purification of Co-Expressed his-p23 and p24.

The cloning and purification schematic of his-p23 and p24 is exactly the same as described for the individual recombinant proteins. The only difference is that the PCR insert at the multiple cloning site began with the start codon for ORF23 and ended with the last codon for ORF24. It should be noted that ORF24 was not cloned into a separate site with its own promoter and tag.

Inhibition of Phage Infection.

Overnight cultures of *B. anthracis* ΔSterne (12 ul) were mixed with molten soft agar (0.8%; 400 ul) and overlayed onto BHI agar plates measuring 35×10 mm. After allowing the bacterial soft agar to sit for 15 min, various dilutions of the purified his-tagged phage protein stocks (PBS dilutions; 100 ul) were evenly placed on top. The protein overlay was incubated atop the bacterial agar for 15 min before a final overlay of Wip1 phage (~100 PFU) was evenly added. Resulting plaques were counted at 48 hrs post infection. All steps were conducted at room temperature.

Inhibition of Phage Adsorption Using Polyclonal Antisera Against his-Tagged Wip1 p23.

To generate polyclonal antisera against his-tagged Wip1 p23, 500 ug of the purified protein was run on an SDS-PAGE gel and excised bands were used as antigen to immunize two New Zealand white rabbits. Pre-immune serum was collected before the first immunization in complete Freund's adjuvant and for the second, third, and fourth immunizations in incomplete Freund's adjuvant. Immunizations and production bleeds were collected at 3 week intervals for a total of 21 weeks. An indirect ELISA assay was used to determine the titer of the polyclonal antisera against his-p23. The titer was found to be 2,000 (the highest dilution to yield an absorbance=1 in 15 minutes).

The antisera were then tested for ability to inhibit Wip1 phage binding activity. Various dilutions of serum (in BHI media) were mixed with Wip1 phage stock (~800 PFU) and incubated in a 37° C. water bath for 30 min. After adding 100 ul of overnight cultures of *B. anthracis* ΔSterne, the serum-phage-bacterium mixtures were incubated at room temperature for 30 min. Bacterial pellets were collected via centrifugation at 12,500 rpm for 30 seconds, washed, and resuspended in 10 mM K phosphate buffer. Bacteria-bound phage were plated onto BHI and proceeded to form plaques overnight. The inhibition rate was measured as the percentage reduction of Wip1 PFUs as compared to a no-serum, PBS control.

Fluorescence Microscopy.

The following protocol is a modified version of one previously described [Raz, A. and V. A. Fischetti, *Sortase A localizes to distinct foci on the Streptococcus pyogenes membrane*. Proceedings of the National Academy of Sciences of the United States of America, 2008. 105(47): p. 18549-54]. Overnight cultures of various bacterial strains were inoculated at a 1:100 dilution in BHI media and grown to mid-exponential phase (unless otherwise noted) by shaking for 3 h at 30° C. The cell cultures were then pelleted by centrifugation (Eppendorf 5810 R; 4,000 rpm; 5 min; 4 C), washed, and then resuspended in PBS. To fix the cells, paraformaldehyde and NaPO4, pH 7.4 were added to the suspension at final concentrations of 2.6% and 30 mM, respectively. The cells were incubated for 15 min at room temperature, followed by 30 min on ice, washed with PBS, and then attached to polylysine-coated glass cover slips. The fixed cells attached onto glass were then washed with PBS and blocked with PBS containing 1% BSA for 15 min. The cells subsequently underwent a series of three labeling steps: first with purified his-tagged Wip1 protein, then with anti-His mouse antibodies, and finally with anti-mouse rhodamine dye and 4',6-diamidino-2-phenylindole (DAPI) stain. Each labeling step consisted of incubating the cells with the labeling mixture for 45 min in a moist chamber and was followed by thorough washes with PBS. To reduce bleaching, the slides were mounted with 50% glycerol and 0.1% p-phenylenediamine in PBS pH 8.0. Images were captured using a Delta-Vision image restoration microscope (Applied Precision/Olympus) equipped with CoolSnap QE cooled CCD camera (Photometrics). An Olympus 100× oil immersion objective was used in conjunction with a 1.5× optovar.

Wip1 is Morphologically Similar to Other Tectiviruses.

Wip1 phage is able to produce clear plaques on *B. anthracis* Sterne and ΔSterne strains. Samples of the viral particles with and without the bacterium *B. anthracis* ΔSterne were analyzed by transmission electron microscopy. Wip1 phage alone are tailless, bilayer, icosahedral particles with a vertex to vertex diameter of approximately 60 nm, similar in morphology to other tectiviral phages [Schuch, R. F. V. A., *The Secret Life of the Anthrax Agent Bacillus Anthracis: Bacteriophage-Mediated Ecological Adaptations*. PLos One, 2009. 4(8): p. e6532]. Treatment with chloroform inhibited Wip1 activity, which is consistent with Wip1 possessing an inner lipid membrane (data not shown).

Upon incubation with its host *B. anthracis* ΔSterne, Wip1 displayed a tube-like structure (FIG. 1) that has been described in other tectiviruses such as Bam35 and PRD1 [Ackermann, H. W. R., R.; Martin, M.; Murthy, M. R.; Smirnoff, W. A., *Partial Characterization of a Cubic Bacillus Phage*. Canadian Journal of Microbiology, 1978. 24: p. 986-993; Laurinmaki, P. A. H., J. T.; Bamford, D. H.; Butcher, S. J., *Membrane Proteins Modulate the Bilayer Curvature in the Bacterial Virus Bam*35. Structure, 2005. 13: p. 1819-1828; Rydman, P. S. C., J.; Butcher, S. J.; Fuller, S. D.; Rutten, T.; Bamford, D. H., *Bacteriophage PRD*1 *contains a labile receptor-binding structure at each vertex*. J. Mol. Biol., 1999. 291: p. 575-587]. In PRD1, interaction of protein P2 with the host receptor leads to a conformational change that results in the dissociation of the spike complex proteins from the virion [Grahn, A. M. C., J.; Bamford, J. K.; Bamford, D. H., *Stable Packaging of Phage PRD*1 DNA Requires Adsorption Protein P2*, Which Binds to the IncP Plasmid-Encoded Conjugative Transfer Complex*. Journal of bacteriology, 1999. 181(21): p. 6689-6696]. This is followed by the transformation of the spherical internal membrane into a tubular channel structure for the delivery of viral DNA into the host [Daugelavicius, R.

Figure 1:
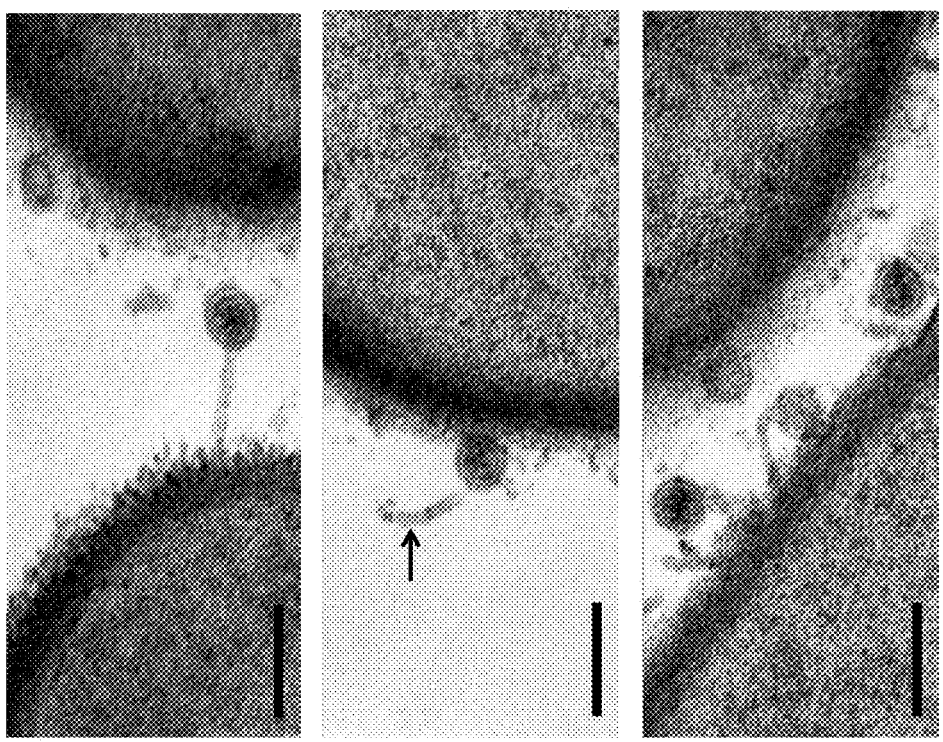
FIG. 1 shows TEM of the Wip1 phage on *B. anthracis*. Wip1 was incubated with *B. anthracis* ΔSterne for 5 minutes at a MOI of 10 before being fixed for TEM imaging. Scale bar=0.1μ.

B., J. K.; Bamford, D. H., *Changes in host cell energetics in response to bacteriophage PRD1 DNA entry*. Journal of bacteriology, 1997. 179: p. 5203-5210; Grahn, A. M. D., R.; Bamford, D. H., *Sequential model of phage PRD1 DNA delivery: active involvement of the viral membrane*. Mol. Microbiol., 2002. 46: p. 1199-1209]. In some cases, the phage tails were seen to interact in a conventional way with the bacterial cell surface. However, TEM images also captured several Wip1 phages with tube-like structures facing away from the bacterial surface (FIG. 1) instead of directly towards the host, a phenomenon not reported in other tectiviruses [Bamford, D. H., *Personal communication*, 2006: New York]. This could indicate that the labile vertex undergoing tubular transformation may not be the same as the vertex that initially binds the receptor. This could also be explained by reversible binding between the Wip1 tube-like structure and its host.

Wip1 Infection and Adsorption are Highly Specific to *B. anthracis*.

Previous studies determined that Wip1 infectivity is more specific to *B. anthracis* than the standard diagnostic tool γ phage [Schuch, R., et al., *Prevalence of Bacillus anthracis-like organisms and bacteriophages in the intestinal tract of the earthworm Eisenia fetida*. Applied and environmental microbiology, 2010. 76(7): p. 2286-94]. We decided to expand the host range study to include adsorption and infection of Wip1 virions to the surface of different bacteria. Adsorption assays showed that Wip1 binding also exhibited a high specificity to *B. anthracis* that corresponded with its narrow infectivity host range (Table 1). This observation further supported the model of Wip1 tropism being mediated by the receptor binding proteins on its surface.

TABLE 1

Wip1 infectivity and adsorption range.

| Strain | Infectivity (PFU/ml) protein | | Adsorption (%) |
|---|---|---|---|
| | Wgamma | Wip1 | Wip1 |
| *B. anthracis* | | | |
| deltaSterne | 3.0E+09 | 6.0E+9 | 100 |
| *Bacillus cereus* | | | |
| ATCC 4342 | 1.0E+05 | <10 | <5 |
| CDC32805 | 4.0E+07 | 3.0E+07 | 94 |
| CDC13100 | <10 | <10 | <5 |
| CDC13140 | <10 | <10 | <5 |
| ATCC 10987 | <10 | <10 | <5 |
| NRL 569 | <10 | <10 | <5 |
| ATCC 14579 | <10 | <10 | <5 |
| ATCC 13472 | <10 | <10 | <5 |
| ATCC 11980 | <10 | <10 | <5 |
| RTS 100 | <10 | <10 | <5 |
| *B. thuringiensis* | | | |
| HD1 | <10 | <10 | <5 |
| HD73 | <10 | <10 | <5 |
| *B. subtilis* SL4 | <10 | <10 | <5 |
| *B. pumilis* SL4680 | <10 | <10 | <5 |
| *Sporosarcina ureae* | <10 | <10 | <5 |
| *B. megaterium* WH32 | <10 | <10 | <5 |
| *Brevibacillus laterosporus* | <10 | <10 | <5 |

Wip1 is Related to Other Tectiviruses with Notable Differences.

Figure 2:
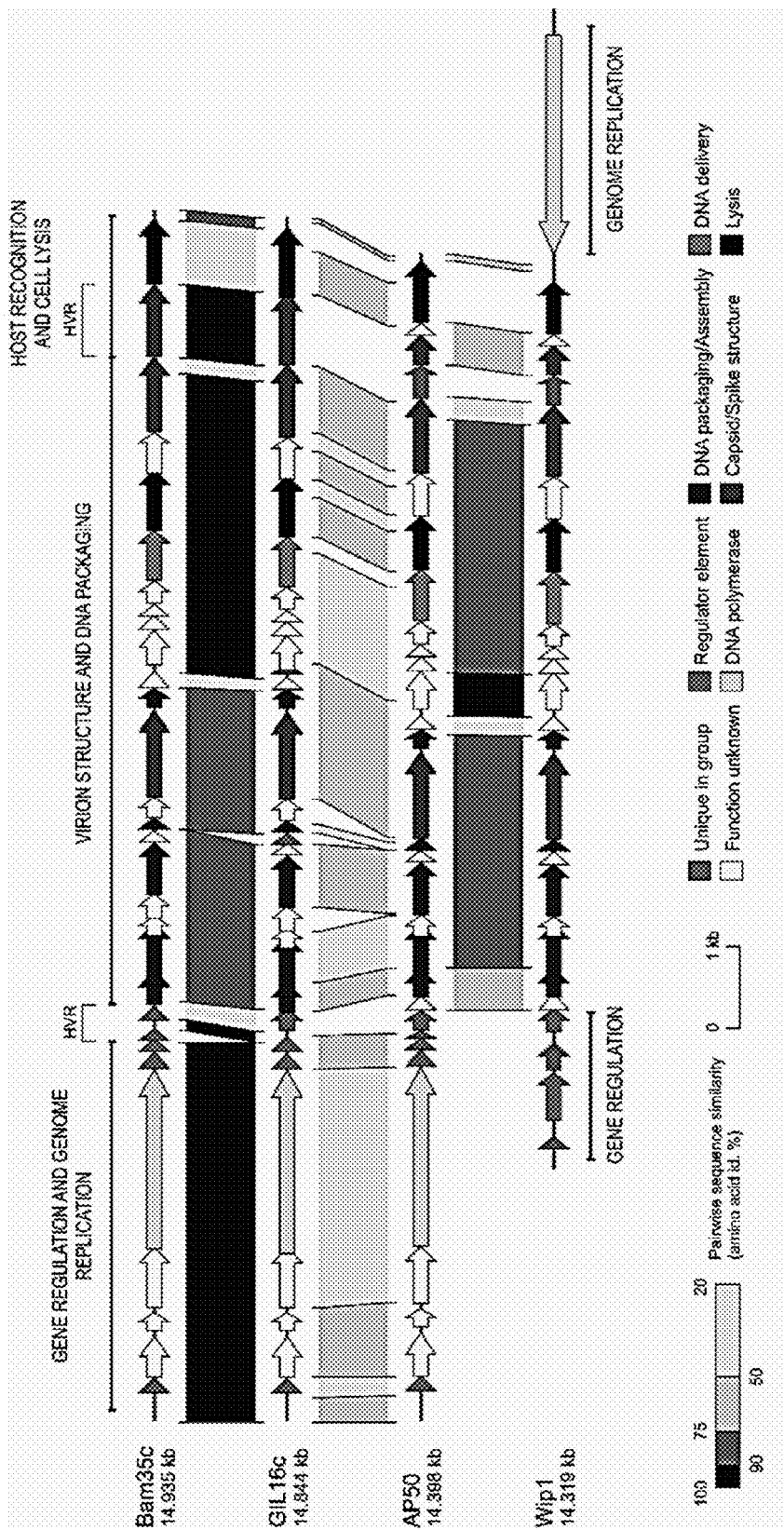
FIG. 2 shows alignment of Bam35c, Gil16c, AP50 and Wip1 genome maps. Predicted genes are represented as block arrows and the color key in the bottom right indicates postulated functions. Shaded regions pair conserved sequence segments between phages and amino acid identity, percentage ranges are shown in the lower left corner.

The Wip1 genome was determined to be a linear molecule of DNA measuring 14,319 bp. Detailed analysis of the Wip1 sequence revealed the existence of 27 putative open reading frames (ORFs), as shown in FIG. 2. Wip1 exhibits sequence similarities to gram-positive infecting tectiviruses Bam35c and Gil16c. Wip1 is most closely related to AP50, which also has a narrow host range highly specific to *B. anthracis* [Sozhamannan, S., et al., *Molecular Characterization of a Variant of Bacillus anthracis-Specific Phage AP50 with Improved Bacteriolytic Activity*. Applied and environmental microbiology, 2008. 74(21): p. 6792-6796]. The genome of Wip1 from ORF5 through ORF25 is strikingly similar to the section of AP50 from ORF10 through ORF30 in ORF size, sequence, and organization (Tables 2a, 2b, 2c, and FIG. 2). Among the 27 total putative Wip1 ORFs, 19 share sequence identity of at least 50% to other tectiviral proteins and 14 share high sequence identity of at least 75% to AP50 proteins. We noted that the Wip1 genome GC content at both extremities is lower than the percentage observed in the central section of the genome. The GC content is approximately the same in all the Wip1 ORFs as compared to their corresponding AP50 homologs [Sozhamannan, S., et al., *Molecular Characterization of a Variant of Bacillus anthracis-Specific Phage AP50 with Improved Bacteriolytic Activity*. Applied and environmental microbiology, 2008. 74(21): p. 6792-6796].

TABLE 2a

Comparison of genes in Wip1 with other Tectiviridae

| Wip1 ORF | No. of residues (genome coordinates) | Strand | G + C content (%) |
|---|---|---|---|
| 1 | 57 (396-569) | + | 29.5 |
| 2 | 196 (598-1188) | + | 30.7 |
| 3 | 112 (1219-1557) | + | 25.7 |
| 4 | 91 (1690-1965) | + | 25.7 |
| 5 | 67 (1958-2161) | + | 27.9 |
| 6 | 116 (2121-2471) | + | 43.9 |
| 7 | 236 (2309-3019) | + | 46.8 |
| 8 | 83 (2865-3116) | + | 46.4 |
| 9 | 212 (3125-3763) | + | 42.4 |
| 10 | 54 (3760-3924) | + | 36.4 |
| 11 | 47 (3938-4081) | + | 33.6 |
| 12 | 353 (4081-5142) | + | 40.7 |
| 13 | 74 (5191-5415) | + | 38.2 |
| 14 | 59 (5421-5600) | + | 32.8 |
| 15 | 157 (5677-6150) | + | 38.8 |
| 16 | 61 (6138-6323) | + | 36.0 |
| 17 | 48 (6323-6469) | + | 36.1 |
| 18 | 91 (6482-6757) | + | 43.1 |
| 19 | 213 (6761-7402) | + | 44.8 |
| 20 | 218 (7402-8058) | + | 44.1 |
| 21 | 175 (8055-8582) | + | 46.4 |
| 22 | 291 (8593-9468) | + | 44.7 |
| 23 | 117 (9472-9825) | + | 39.8 |
| 24 | 118 (9838-10194) | + | 36.7 |
| 25 | 48 (10196-10342) | + | 33.3 |
| 26 | 213 (10344-10985) | + | 42.3 |
| 27 | 898 (11342-14038) | − | 29.7 |

TABLE 2b

Comparison of genes in Wip1 with other Tectiviridae

| Wip1 ORF | Identity (%) | | | ORF (# residues) | | |
|---|---|---|---|---|---|---|
| | AP50 | GIL16c | Bam35c | AP50 | GIL16c | Bam35c |
| 1 | | | | | | |
| 2 | | | | | | |
| 3 | | | | | | |
| 4 | | | | | | |
| 5 | 55.1 | | | 10 (57) | | |
| 6 | 69.6 | 62.5 | 45.7 | 11 (114) | 9 (125) | 10 (145) |

TABLE 2b-continued

Comparison of genes in Wip1 with other Tectiviridae

| Wip1 ORF | Identity (%) | | | ORF (# residues) | | |
|---|---|---|---|---|---|---|
| | AP50 | GIL16c | Bam35c | AP50 | GIL16c | Bam35c |
| 7 | 78.4 | 42.2 | 44.0 | 12 (235) | 10 (248) | 11 (252) |
| 8 | 94.0 | 53.2 | 53.2 | 13 (83) | 11 (80) | 12 (80) |
| 9 | 93.9 | 59.9 | 63.7 | 14 (212) | 13 (212) | 14 (212) |
| 10 | 89.1 | 60.9 | 60.9 | 15 (46) | 14 (46) | 15 (46) |
| 11 | 80.9 | 48.8 | 48.8 | 16 (49) | 16 (46) | 16 (46) |
| 12 | 83.8 | 63.1 | 63.9 | 17 (354) | 18 (356) | 18 (356) |
| 13 | 78.4 | 35.7 | 34.3 | 18 (74) | 19 (76) | 19 (76) |
| 14 | 34.4 | 46.8 | 39.4 | 19 (56) | 20 (52) | 20 (68) |
| 15 | 86.6 | 37.2 | 37.8 | 20 (157) | 22 (143) | 21 (143) |
| 16 | 79.3 | 60.7 | 60.7 | 21 (58) | 23 (58) | 22 (58) |
| 17 | 77.1 | 54.2 | 54.2 | 22 (48) | 24 (48) | 23 (48) |
| 18 | 82.4 | 35.6 | 33.3 | 23 (91) | 25 (91) | 24 (91) |
| 19 | 85.1 | 23.5 | 25.9 | 24 (210) | 26 (204) | 25 (204) |
| 20 | 91.7 | 66.4 | 65.4 | 25 (218) | 27 (250) | 26 (250) |
| 21 | 84.6 | 62.2 | 63.4 | 26 (175) | 28 (170) | 27 (170) |
| 22 | 63.9 | 43.1 | 40.3 | 27 (304) | 29 (297) | 28 (304) |
| 23 | | | | | | |
| 24 | 50.8 | | | 29 (118) | | |
| 25 | 71.7 | | | 30 (49) | | |
| 26 | | | | | | |
| 27 | | | | | | |

TABLE 2c

PRD1 protein and postulated function of Wip1 ORFs.

| Wip1 ORF | PRD1 protein (no. of residues) Ref] | Postulated function |
|---|---|---|
| 1 | | |
| 2 | | Transcription factor |
| 3 | | LexA-type repressor |
| 4 | | |
| 5 | | |
| 6 | P6 (166) [32 [1]] | DNA packaging/unique vertex |
| 7 | P10 (203) [33[2], 34[3]] | Assembly |
| 8 | | |
| 9 | P9 (227) [d[4]] | DNA packaging ATPase |
| 10 | | |
| 11 | P20 (42) [e] | DNA packaging/unique vertex |
| 12 | P3 (395) [f[5]] | Major capsid protein |
| 13 | P22 (47) [g] | DNA packaging/unique vertex |
| 14 | | |
| 15 | | |
| 16 | | |
| 17 | | |
| 18 | | |
| 19 | P11 (207) [h[6]] | DNA delivery |
| 20 | P7 (265) | Lysin |
| 21 | | |
| 22 | P5 (340) [i[7]] | Trimeric spike protein |
| 23 | | |
| 24 | | |
| 25 | | |
| 26 | | Lysin |
| 27 | | DNA polymerase |

ORFs were predicted using GeneMark (exon.biology.gatech.edu/heuristic_hmm2.cgi) and G+C % were determined using the GC calculator at www.sciencebuddies.org. Protein identities were determined with the Pairwise Sequence Alignment program Water available from EMBOSS at the EMBL-EBI node (www.ebi.ac.uk/Tools/psa/emboss_water!). A summary of PRD1 gene functions can be found in [j[8]] and PRD1 homologs in Bam35c were determined in [22]. Relevant references are indicated in brackets: [a] Stromsten, N. J., Benson, S. D., Burnett, R. M., Bamford, D. H., Bamford, J. K., The *Bacillus thuringiensis* linear double-stranded DNA phage Bam35, which is highly similar to the *Bacillus cereus* linear plasmid pBClin15, has a prophage state. Journal of Bacteriology, 2003. 185(23): p. 6985-6989; [b] Mindich, L., Bamford, D., McGraw, T., Mackenzie, G., Assembly of bacteriophage PRD1: particle formation with wild-type and mutant viruses. Journal of Virology, 1982. 44(3): p. 1021-1030; [c] Rydman, P. S., Bamford, J. K., Bamford, D. H., A minor capsid protein P30 is essential for bacteriophage PRD1 capsid assembly. J Mol Biol, 2001. 313(4): p. 785-795; [d] Bamford, J. K., Hanninen, A. L., Pakula, T. M., Ojala, P. M., Kalkkinen, N., Frilander, M., Bamford, D. H., Genome organization of membrane-containing bacteriophage PRD1. Virology, 1991. 183(2): p. 658-676; [e] uniprot.org/uniprot/P27587; [f] Benson S. D., Bamford, J. K., Bamford, D. H., Burnett, R. M., The X-ray crystal structure of P3, the major coat protein of the lipid-containing bacteriophage PRD1, at 1.65 A resolution. Acta Crystallogr D Biol Crystallogr., 2002. 58: p. 39-59; [g] uniprot.org/uniprot/P27388; and [h] Bamford, J. K. and Bamford, D. H., Large-scale purification of membrane-containing bacteriophage PRD1 and its subviral particles. Virology, 1991. 181(1): p. 348-352.

A distinction of the Wip1 genome is the placement of the putative DNA polymerase, ORF27, at the 3' end of the genome on the negative strand. All other tectiviral DNA polymerases are encoded in the first 5,000 base pairs of their genomes on the positive strand. While several polymerase motifs were identified in the Wip1 ORF27 sequence, the unusual Wip1 ORF27 gene product does not share any significant homology with any other proteins in the NCBI database.

Another notable section of the genome includes Wip1 ORF22, ORF23, and ORF24. Wip1 ORF22 is predicted to be a putative spike complex protein as it shares 40.3% sequence identity with Bam35 gp28, a homolog for PRD1 trimeric spike protein P5. Bam35 gp28 is followed by gp29, a 293 amino acid protein that also resides on the phage surface [Ravantti, J. J., et al., *Comparative analysis of bacterial viruses Bam35, infecting a gram positive host, and PRD1, infecting gram-negative hosts, demonstrates a viral lineage.* Virology, 2003. 313(2): p. 401-14]. If Wip1 and AP50 genomic organization both align with that of Bam35c, then a putative spike complex protein should follow. Interestingly, in Wip1 and AP50, the genes downstream the P5 homolog are located in a highly variable region and do not share sequence identity with any Bam35 ORFs (FIG. 2). Despite the lack of homology, we predicted that Wip1 gene products 23 and 24 (totaling 235 amino acids together) were putative spike complex proteins based on strikingly similar gene cassette alignment both upstream and downstream of this region. Finally, we were intrigued by the observation that while Wip1 ORF24 shares 51% sequence identity with AP50 ORF29, Wip1 ORF23 is a unique gene that does not share sequence homology to any other known genes, tectiviral or otherwise.

Wip1 p23 and p24 Form a Stable Complex.

Figure 3:
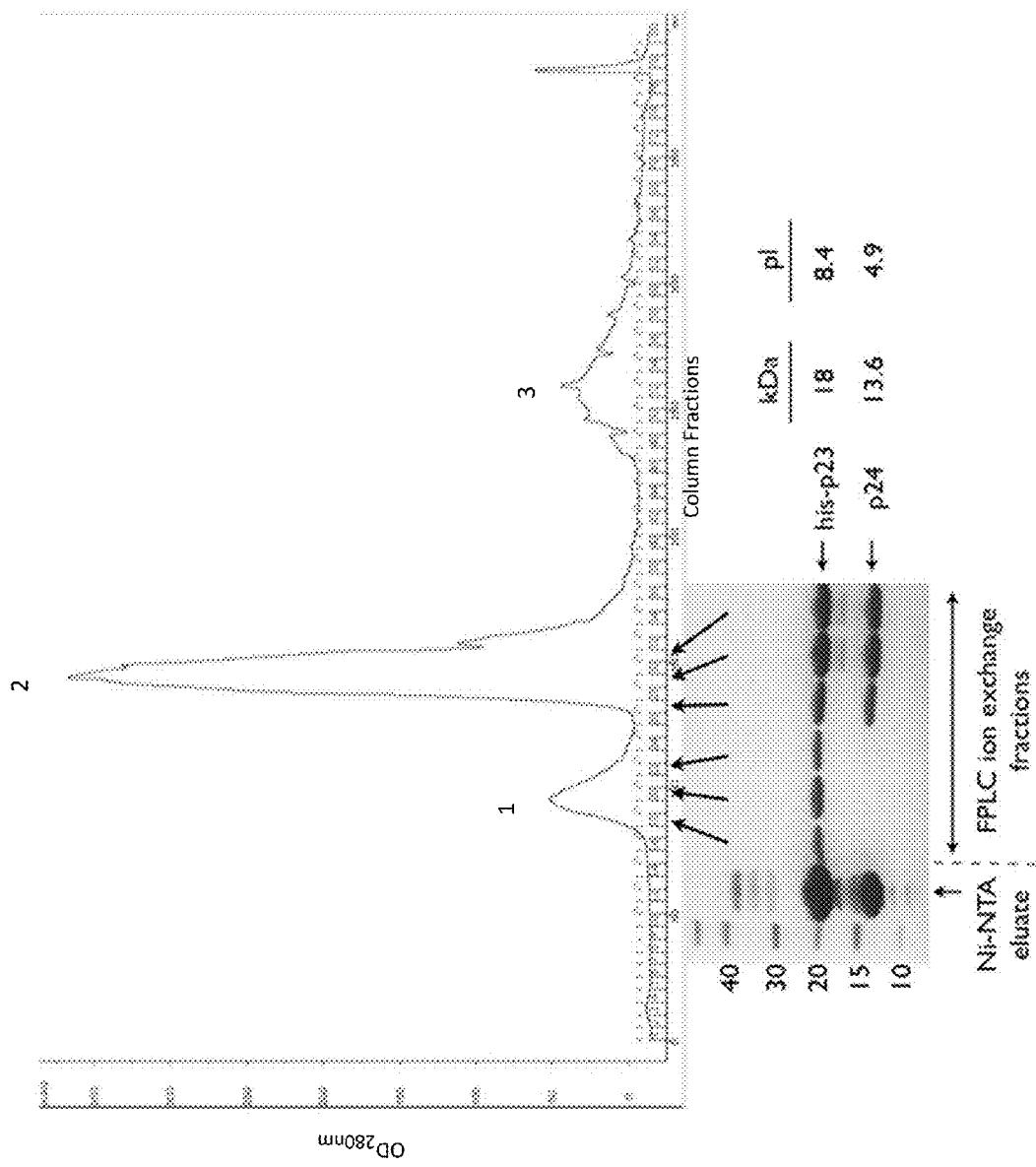
FIG. 3 shows purified proteins. The Ni-NTA eluate containing both his-p23 and p24 (Lane 1) was further purified by charge using ion exchange chromatography. The distinct peaks were evaluated with SDS-PAGE, which revealed the presence of his-p23 alone in Peak 1 and the presence of his-p23 and p24 together in Peak 2.

Genomic analysis predicted three Wip1 proteins, p22, p23, and p24 to be possible candidates for the Wip1 spike complex. We developed expression and purification schemes for the his-tagged constructs of all three viral proteins. However, the separately expressed his-p23 and his-p24 constructs resulted in extremely low yields of soluble protein due to the formation of inclusion bodies (data not shown). Curiously, when his-p23 and p24 were co-expressed, significantly higher yields of soluble protein were generated, suggesting that his-p23 and p24 assist each other in proper folding when expressed together. We used this co-expressed complex to purify the two molecules away each other. However, when the his-p23 and p24 complex were eluted from a stringentlywashed Ni-NTA column, both eluted together despite the fact that p24 was not his-tagged (FIG. 3). When we used this Ni-NTA eluate to separate the two proteins by ion exchange chromatography, the two proteins were again observed together in the same fractions despite the fact that his-p23 and p24 exhibit drastically different pIs of 8.4 and 4.9, respectively (FIG. 3). This observation strongly suggests that p23 and p24 form a stable complex.

Wip1 p23 is a Receptor-Binding Protein.

Figure 4A:
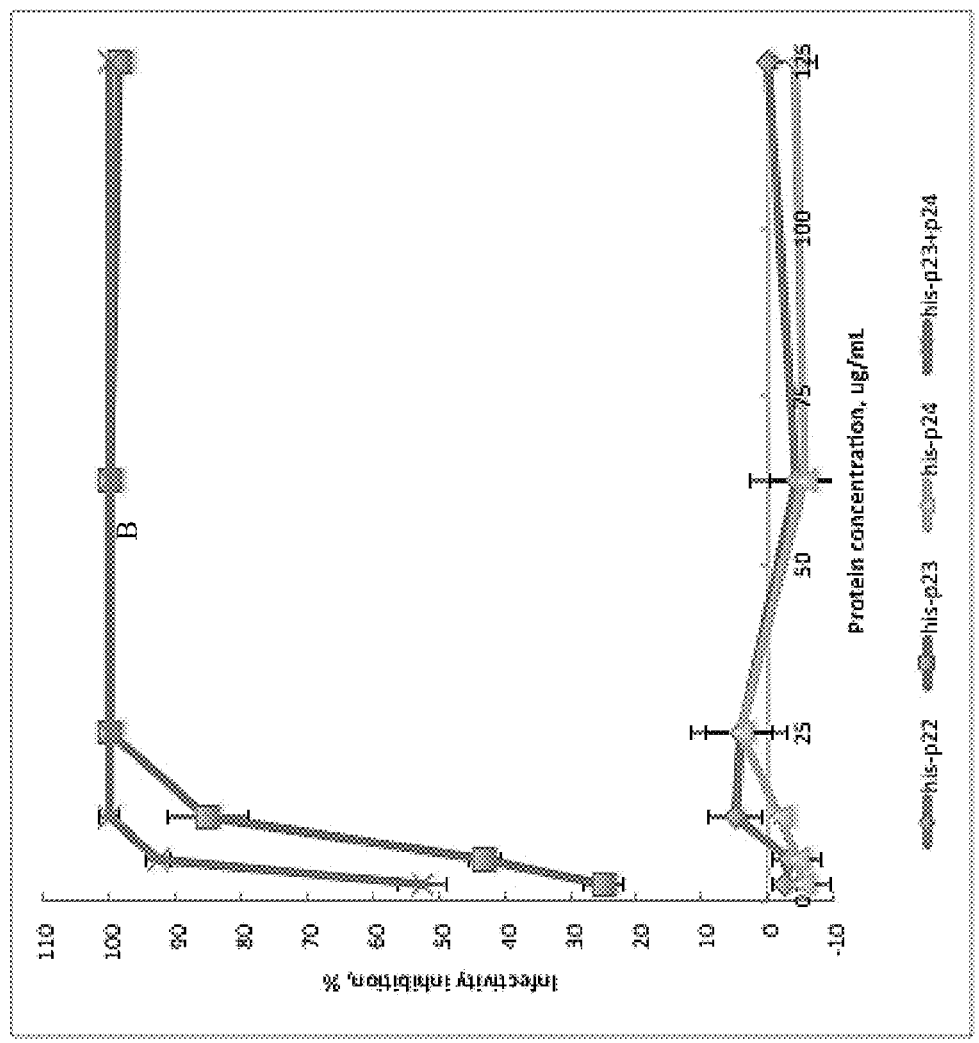
FIG. 4 shows Wip1 inhibition of infectivity by recombinant Wip1 proteins. A) Wip1 phage was assayed for inactivation by recombinant viral proteins at various concentrations. Protein concentrations are indicated per protein. His-p23 (red) and the his-p23+p24 complex (purple) inactivated Wip1 infectivity by up to 100% in a dose-dependent manner.

The purified recombinant proteins were subsequently used in the Wip1 activity inhibition assay, which consisted of overlaying the viral proteins on top of *B. anthracis* ΔSterne growing in soft agar before adding a final overlay of infectious Wip1 phage. His-p23 was shown to competitively inhibit Wip1 infectivity up to 100% in a dose-dependent manner while his-p22 and his-p24 had no effect on phage infectivity (FIG. 4A). This finding suggests that Wip1 p23 is a receptor binding protein. We also tested the his-p23 and p24 complex in this assay at a 2× total concentration to account for the presence of two proteins that make up each protein complex. The his-23 plus p24 complex exhibited higher inhibition levels than his-p23 alone, a finding that may be explained by either increased protein stability or enhanced activity of the receptor binding complex. The possibility that recombinant his-p22 and his-p24 may not possess their full biological activity because of the linked histidine should be noted. However, the issues of potential misfolding or activity interference caused by a histidine tag are partially addressed for p24 with the co-expressed his-p23 plus p24 complex.

Figure 4B:
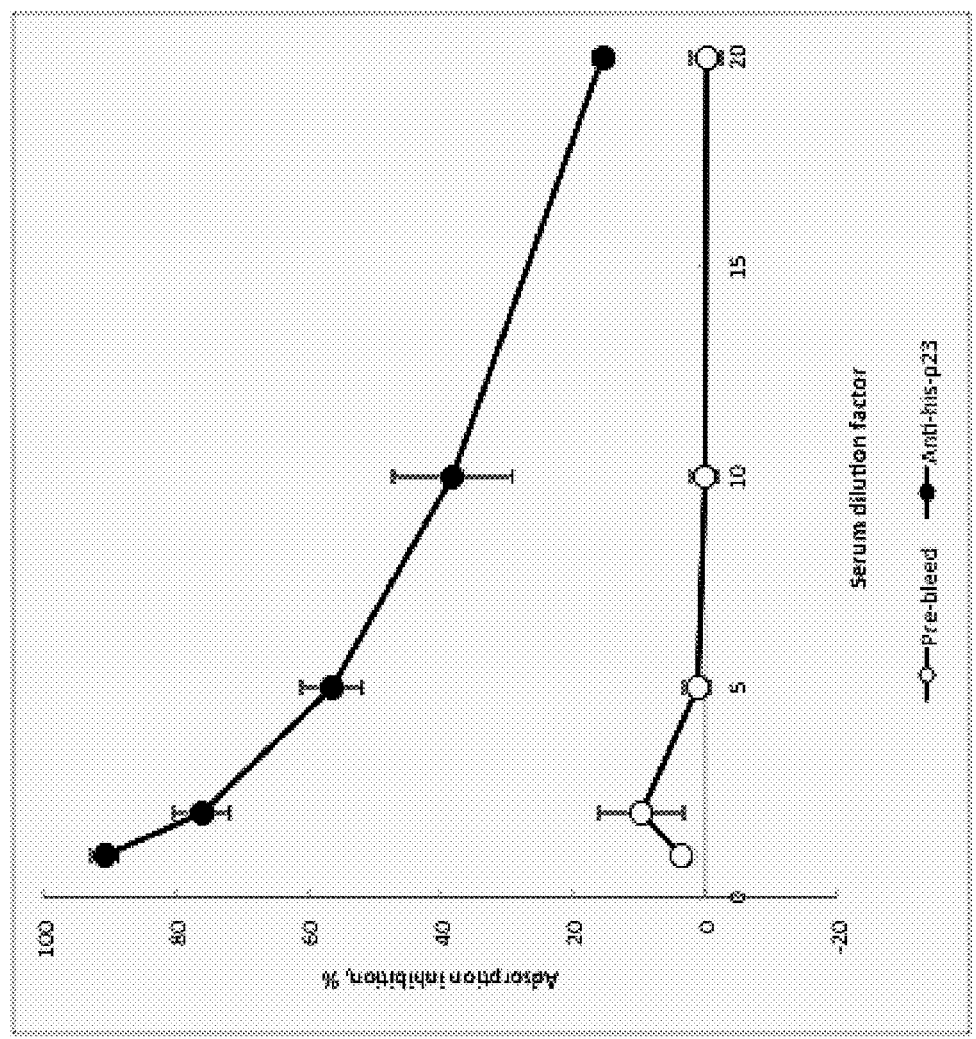

In a second phage inhibition assay, we used polyclonal antisera against Wip1 his-p23 to inhibit phage binding activity. *B. anthracis* ΔSterne bacteria was added to pre-incubated mixtures of Wip1 phage and antiserum at multiple dilutions. The cells were pelleted and the supernatant plated to reveal the titer of unbound phage. The results revealed that anti-his-p23 antibodies reduced Wip1 adsorption by up to 90% in a dose-dependent manner. Pre-bleed serum did not have an effect on Wip1 activity (FIG. 4B). This suggests that Wip1 p23 protein resides on the phage surface and is consistent with the finding that it is a receptor-binding molecule.

Wip1 p23 Binding is Specific to *B. anthracis*.

To further understand the interaction between Wip1 proteins and bacterial surfaces, the purified his-tagged viral proteins were tested for surface labeling of select bacterial strains using indirect immunofluorescence microscopy. FIG. 5 shows that both his-p23 and the his-p23 plus p24 complex bind specifically to the surface of *B. anthracis* ΔSterne. Surprisingly, the Wip1 proteins bound all mid-log phase ΔSterne uniformly but bound only a subpopulation of stationary phase ΔSterne. His-p22 and his-p24 were unable to bind either growth phase of ΔSterne, further suggesting that Wip1 p22 and p24 are not involved with phage adsorption. The lesser ability of Wip1 to bind to stationary phase bacteria is probably due to the replacement of surface array protein (Sap) with EA1 protein as the bacteria transition from log phase to stationary phase [Mignot, T., et al., *Developmental switch of S-layer protein synthesis in Bacillus anthracis*. Mol Microbiol, 2002. 43(6): p. 1615-27]; Sap is believed to be the AP50 tectivirus receptor [Bishop-Lilly, K. A., et al., *Whole genome sequencing of phage resistant Bacillus anthracis mutants reveals an essential role for cell surface anchoring protein CsaB in phage AP50c adsorption*. Virol J, 2012. 9: p. 246.] and may be important for Wip1 attachment as well.

In FIG. 6, the specificity of the binding of his-p23 and the his-p23 plus p24 complex to *B. anthracis* is shown by indirect immunofluorescence microscopy. Neither of the protein constructs were able to bind the surface of *B. cereus* ATCC 4342, CDC13100, and CDC13140; the three strains that are susceptible to γ infection but not to Wip1 infection. As expected, they were also unable to bind *B. cereus* strains ATCC 10987 and NRL 569, as well as *B. thuringiensis* strains HD1 and HD73, none of which can be infected by either γ or Wip1 phage. His-p23 and the his-p23 plus p24 complex bound positively to only *B. anthracis* Sterne, ΔSterne, and *B. cereus* CDC32805, the only *B. cereus* strain in our host range analysis that supported Wip1 replication (Table S1). These findings suggest that his-p23 does not bind to just any gram-positive bacterial surface, but binds very specifically to the bacterial hosts that support Wip1 infection, including *B. anthracis* ΔSterne.

TABLE S1

Comparative table of Wip1 host range and his-p23 binding.

| Strain | Infectivity (PFU/ml) | | Adsorption (%) protein | Immunofluorescence | |
|---|---|---|---|---|---|
| | Wgamma | Wip1 | Wip1 | his-p23 | his-p23+24 |
| *B. anthracis* | | | | | |
| deltaSterne | 3.0E+09 | 6.0E+9 | 100 | + | + |
| *Bacillus cereus* | | | | | |
| ATCC 4342 | 1.0E+05 | <10 | <5 | − | − |
| CDC32805 | 4.0E+07 | 3.0E+07 | 94 | + | + |
| CDC13100 | <10 | <10 | <5 | − | − |
| CDC13140 | <10 | <10 | <5 | − | − |
| ATCC 10987 | <10 | <10 | <5 | − | − |
| NRL 569 | <10 | <10 | <5 | − | − |
| *B. thuringiensis* | | | | | |
| HD1 | <10 | <10 | <5 | − | − |
| HD73 | <10 | <10 | <5 | − | − |

Bacterial strains that support Wip1 infectivity and adsorption showed positive labeling by immunofluorescent his-p23 and his-p23+p24 complex. Bacterial strains resistant to Wip1 activity were not labeled by his-p23 or his-p23+p24 complex. The lower limit of detection of infectivity is indicated by "<10", while the lower limit of detection of adsorption is indicated by "<5."

The polynucleotide sequences presented in the Sequence Listing that is part of this specification comprise the polynucleotide sequence of the genome of *Bacillus* phage Wip1 (the genome is designated as ORIGIN) and 26 open reading frames (ORFs) encoded by the genomic sequence, the ORFs constituting polypeptide sequences. For convenience in this specification, the polypeptides encoded by the ORFs are referred to as, for example, ORF1, ORF2, etc., and p1, p2, etc., and these polypeptide sequences are part of this description, as are the names and descriptions of the putative functions of the proteins as presented in the Sequence Listing below. In the Sequence Listing, nucleotide triplets with paired colors designate start and stop codons for the ORFs in the 5'-3' direction.

While the present invention has been described with reference to the specific embodiments thereof, it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include plural references unless the context clearly dictates otherwise. All technical and scientific terms used herein have the same meaning.

Publications disclosed herein are incorporated in their entirety. Nothing herein is to be construed as an admission that the present invention is not entitled to antedate such publications by virtue of prior invention. Further, the dates of publication provided may be different from the actual publication dates which may need to be independently confirmed.

```
SEQUENCE LISTING:
    14319 bp  DNA linear
    Source    Bacillus phage Wip1
    Organism  Bacillus phage Wip1
              Viruses; dsDNA viruses, no RNA stage;
Tectiviridae; Tectivirus.
    FEATURES     Location/Qualifiers
        source   1 . . . 14319
                 /organism="Bacillus phage Wip1"
                 /mol_type="genomic DNA"
                 /host="Bacillus anthracis"
        CDS      396 . . . 569
                 /note="ORF1"
                 /codon_start=1
                 /trans_table=11
                 /product="hypothetical protein"
        /translation="MAKIHPYPQYVRKIICTDCGCIIEKNINYKPPKNNYFQKCNEXQSPNTIVS
YKEKKR"
        CDS      598 . . . 1188
                 /note="ORF2"
                 /codon_start=1
                 /trans_table=11
                 /product="hypothetical protein"
        /translation="LKKKKTLYKEIRELGFDVNFSRKVSRRKDGAFDKVRLEELLFKYKGDASLVEKVFH
GNQSLTKKEISKFINAERRERKFFKGRYAGEFSTKERSILEKTLSSSGLKEVNRLLKNNTIDILSRTEEFKQFIGRG
KKPPKHMIKDIKRINKFMGASPNGQPGLFVVREMYINGLTELEAIELIKDRQSPVDKDTVFYS"
        CDS      1219 . . . 1557
                 /note="ORF3"
                 /codon_start=1
                 /trans_table=11
                 /product="putative LexA-like repressor"
        /translation="MMNDTEKTIFNAIENFQTEHGYSPSLTELEEETFYSRSTVRHCIKTLEEKGYLELD
RQVRRNIRLRNMSAIIKDVKENINDDSKVISVDVIIDILNILHNELSNDNRTKRII"
        CDS      1690 . . . 1965
                 /note="ORF4"
                 /codon_start=1
                 /trans_table=11
                 /product="hypothetical protein"
        /translation="MKIHDKKFEIDKELSDAICWELSEYQTIITLALTNCSKDEVLKISQLVDRNERFSE
TTKEWLKETINKFHKPIWEMELKNNKTELKIAQNV"
        CDS      1958 . . . 2161
                 /note="ORF5"
                 /codon_start=1
                 /trans_table=11
                 /product="hypothetical protein"
        /translation="MFKSVSKIYRDSLKQNIKLNDENAELREQNILLKRKLAKSESLLYQLQNDRSVTNG
LIKSSRRKTEI"
        CDS      2121 . . . 2471
                 /note="ORF6"
                 /codon_start=1
                 /trans_table=11
                 /product="putative capsid protein"
```

```
          /translation="MDSLKVVEEKPKFRLGDFQFFAKKKEEGEEEDLEDVEEEYEEGEDVPKPKRKPKSK
SEEEAPAWAQKIIDLVTPKAEEQNQKQKVPVPEAPVVEEEEEEQPQQEGAVKRFLRQLW"
     CDS       2309 . . . 3019
               /note="ORF7"
               /codon_start=1
               /trans_table=11
               /product="putative virion assembly protein"
          /translation="MGAKDNRLSNPESGGTEPKTESTSTRSTSSGGRGRRGAAATGGSSEKIPKATLVEV
PGQEKSPEDAKKEEQRKAAAARKRKSRAAANTKKKASASVGDATQLTALVLTTSNIIAAREGMAMWAMSQQEVDQII
TPLYSILSRNDGLGEVMGEYADHIALIVAAFTIFVPKFMMWKASRPKKEGTHYARPNQSTKREQGKQTGEVAAGSGP
SGGQSTNNGTTFGRELSQLIPPSAGI"
     CDS       2865 . . . 3116
               /note="ORF8"
               /codon_start=1
               /trans_table=11
               /product="hypothetical protein"
          /translation="MLDQIKVPNENKGSKQERLQLVVDQVVDSLPTTVRLLAGSYLNSFRQVLESEQQDIDG
NIDNALSRLREYIDYIQYGHDQENE"
     CDS       3125 . . . 3763
               /note="ORF9"
               /codon_start=1
               /trans_table=11
               /product="putative DNA packaging ATPase"
          /translation="MERIPTDQHVFITGQTGTGKSFLAETYLAGYEHVVKLDTKGEVFERRKKKQPVWRG
LREGKDFTVIERLADIDDVETKKIIYAPVFQEQEMEYYDALMQWVYRRENTQLWVDELMEVCPSPFKYPPYLKGLMT
RGRSKEATVWACTQRPSDIPSIVMGNSDHFFVFDQNLPSDRKKLCETTGSSEFMELPGYRNFWYFKRGWSDPVLATL
KV"
     CDS       3760 . . . 3924
               /note="ORF10"
               /codon_start=1
               /trans_table=11
               /product="hypothetical protein"
          /translation="VTLKGGAIVEGKFAGIGLKNILAIFFLFIVFIVMAKVVLTKYPIKGISEVIQTV"
     CDS       3938 . . . 4081
               /note="ORF11"
               /codon_start=1
               /trans_table=11
               /product="putative DNA packaging protein"
          /translation="MNLFSPKWWISSLIAAFMAMFMIYLVKQIASKANIPFVSKVTEEAYK"
     CDS       4081 . . . 5142
               /note="ORF12"
               /codon_start=1
               /trans_table=11
               /product="putative major capsid protein"
          /translation="MAEQQISAQARAANFATATRQNYQMLPSQQVREESSTIEFTLPKARLLSKIILNVE
AVATLKSKGTAIQTHDFTPYPILRRVSLDLNNGFSPFIVSGRDLVQYNMLRLNPNVLFPSTNPRAMNYVENGASPEG
KDAKIKFSVELPITLNPRDPVGLILLQNPETSVTLTVDVETLAKAYSLNASNADQVLFKSMKVTPMLEAFNIPPVPQ
AFPDISTLKLVSSKSDTFSGNGQNILKLNTGTIYRKLILFIEDKNGNPLADEDFQGNLELVFNQADIPYSIKPEILA
HINHSQLGYALPKGMYAFDFTNQGIPNLGGSRDFIDTERLTEFWLRFSTQKEGKVTVVSENLSRLR"
     CDS       5191 . . . 5415
               /note="ORF13"
               /codon_start=1
               /trans_table=11
               /product="hypothetical protein"
          /translation="MAGELSHFKKDLYPNLGFENTSYLSIPEAEDQQAMVDDQKVAEETARTSNKAGHKN
IMLGIVLLIIIMFVLGKV"
     CDS       5421 . . . 5600
               /note="ORF14"
               /codon_start=1
               /trans_table=11
               /product="hypothetical protein"
          /translation="MDVAQMTQLIGNMGFPIFTAIYFMTYMKKTLDTCTQSMVANTQIMIRIEKFLDDKE
KKS"
     CDS       5677 . . . 6150
               /note="ORF15"
               /codon_start=1
               /trans_table=11
               /product="putative DNA delivery protein"
          /translation="MDRGLTFFTLALLLIWLVFDDLFGEKKYLSKLAGAMTPNLSLPDPARDAVDKVVED
TKENAKKDVTDIKKDTKDAVKDTKKSFDDFINGGFEKEMKKDVNDFKDWTKDLPNPDKMKEKANNDFKAIWDEVSKA
LEDTKKSANDMWDDVTSSVKGWFK"
     CDS       6138 . . . 6323
               /note="ORF16"
               /codon_start=1
```

```
                /trans_table=11
                /product="putative DNA delivery protein"
    /translation="MVQMKNFTESLGFIVAFMVMTIFISMFTNESVTNGFLLLVLASMMVVNADKFTKFL
DGVMK"
    CDS        6323 . . . 6469
                /note="ORF17"
                /codon_start=1
                /trans_table=11
                /product="hypothetical protein"
    /translation="MGRILGIISGIGLLIALYLFLSNARQTTQIIDSMAGNAVSGIKVLQGR"
    CDS        6482 . . . 6757
                /note="ORF18"
                /codon_start=1
                /trans_table=11
                /product="putative minor capsid protein"
    /translation="MLDGTYRYQVQNRQALQALDKRVEIPDARLGVGAAEHLEAMGIRVVYENKVPKLVL
PSVHRLPFEQVQPKNVEPDMFVTDDFHVGDAIMGV"
    CDS        6761 . . . 7402
                /note="ORF19"
                /codon_start=1
                /trans_table=11
                /product="putative DNA delivery protein"
    /translation="MADIVPVVGGGGGGHGSS PSKKTNNKMLFMVGGVVVVVLLVFLQRSKSSGGNVDT
LQNTIPISDSQRLDNFQSIVSGETSAQINGMMKDAQDGWSGMFKDFSEKMTNQMKEMDDRNKEYNKQQQDWVKDSFT
NIKDSLGVGAIRNDDNATFTIGNGTTGAAKTYDQQLNDFRNDRQKLAEEIKRTQSVITFRKNNGLDVSNQVQHYKNL
GAL"
    CDS        7402 . . . 8058
                /note="ORF20"
                /codon_start=1
                /trans_table=11
                /product="lysin"
    /translation="MAADITPFIADAQRIQKQTGIPASIILGQIIFESSGKFPGGLSGLAYNNKNLFGIK
GKGTAGTANMWSKEYDAGGNRVSGFRSYNSWTESLNDHARLLQTDRYAKYLKNATSVEDYANGIIKGGYATDPAYAK
QLLGIIKSNGLTKYDDGKYTFTGGDVSGGSAGGGGSGGSFFAPLFNAIIRALLFVLCVVAALLLFANAFPSVEQTVK
SVAKKVKS"
    CDS        8055 . . . 8582
                /note="ORF21"
                /codon_start=1
                /trans_table=11
                /product="putative pentameric base spike protein"
    /translation="MSGTNGLKLNSKLQEAYNKAIASGLRFTSGFRSGSTGPSGRPDSHSQGMAMDFAGS
KAQMKQFSEWAKMTGLFTEVLYETAGHYDHVHVGWQTGKHPDGKTYVGDHKLIDRVGSGTLGDLQTVGDTVAPAGGG
DKAGFMSSLFTGIFRVVMIVICLIGGVYFIMNAFPQMKQLIK"
    CDS        8593 . . . 9468
                /note="ORF22"
                /codon_start=1
                /trans_table=11
                /product="putative trimeric spike protein"
    /translation="MDRKTNSTWREQTPTIPSKTVFDVVFPDTKPNHYHINNLSAAPIYLGTTTLASPKT
YDIVVNGNGDNMHARDLGVTRITLYNDSPDKARIVLTTFEDKFNPAVLAGRGGSVTVTGGGGGAGGVITGFNASLPS
GDNNIGRVKVTEMPAIDFVLGTLPAGTNNIGKVEVSKLPPLASVGGKIGDVGIQGGVTITSMPAVELEVSKDLNVKE
KSYNDFFYQEPNVEQTEVVFTTDLSRIIFISNDGQNPLKVTLNNRTITLLQNEVIEELPLLTKTIKLVRPSGSGSAR
IMGV"
    CDS        9472 . . . 9825
                /note="ORF23"
                /codon_start=1
                /trans_table=11
                /product="hypothetical protein"
    /translation="MGLKKPAVGGKRVAKGIGKPFQPQGSASWVVEVRGLSFKPSVVATKPKKSQIDADY
PYRVGTVGIARTAFEPPLDEDLLNMINNDGDYSVGRVVTFYDDGFKIYLDKGNEQPWVAYE"
    CDS        9838 . . . 10194
                /note="ORF24"
                /codon_start=1
                /trans_table=11
                /product="hypothetical protein"
    /translation="MYVNKRVYFEKDTGIVVMVTGGFRDDWLHSHPTVQEDMAKYSVLAERVPDTLSMLE
LKEGTYDEEFSKARSFKVDVKTNTIVFDFTPEDKKEVEEKKTPEHRVTMVESAINDILLGGM"
    CDS        10196 . . . 10342
                /note="ORF25"
                /codon_start=1
                /trans_table=11
                /product="hypothetical protein"
    /translation="MTLSGLAAYILNQWLLGKFTNSDLNTLVDRGRITEEHRVYFLSMKEEK"
    CDS        10344 . . . 10985
                /note="ORF26"
                /codon_start=1
```

```
                    /trans_table=11
                    /product="putative lysin"
         /translation="MYYHNRNLANLEKLAPHTRQKAKQWYQYCVENGIEVLIYETTRTIEQQRENVRKGA
         SQTMKSYHLVGQALDFVPAREAEVYWDGYYRNDIQKAIGYAKSIGFEWGGDWKGFVDSPPLHYNYNGYGTDKGNVSD
         EPVHVTGNTGVVRVVVDSALVRREPTTQSPINTDAGENGRLYRGTEWQAWGSTIGEGGYTWYPLGNEMWVRGDLVSW
         RNA"
    CDS       11342 . . . 14038
                    /note="ORF27"
                    /codon_start=1
                    /trans_table=11
                    /product="putative DNA polymerase"
         /translation="MKKINPSFLGVEGLDKLEYSEMEVHLSNVHTFSSPKPTEYLYSDKPKGLYGFKFEI
         DEVTGEIMLFGFCSYNPVTKKNGYHYIYRENEKDMDLSVIYMLKNIIKDCHFNNKIICHFNEIESILILKLLMKRKY
         LEQDEQVKIFQRVLKGINGKFHKKSGSWTEPPIIELDIGNGESIGVSKVLNGNLELFVIKNKKMSKCNTFRSKPFWQ
         KTPIECARNANLKYAEEIKESKINWDLFLNGYNKKVDKNNHKLQDNTYVKKILRENMYNSFLSKDLIYVVMNMFKES
         FGCFPNSFYSAGTLSEAAIAKVLDENELKTFSIDSTMNDWQEKDIDVDIIAKAINLSFDANQGAIIEHEKVGYIARG
         ANTDIGASYPAIMRYCIPDLRNSRVQYFDNIKDFTEIPKPSLKRIVMLTCEFEIPPDVRHTIMIKQKGEEGTVNQIR
         RNVLGFGNFVTTVHYKEVEFLLSQIDKDKHNEVIKEIIEVVVIETDGKLHPISKVIDILWELRLKLRDIGNHSEYIV
         KLITNAIYGKFFQAFQQYACSENEDGEQEIYFAGFDVGYMFNPIVSSMITAFGRIRVQEGALNIERNGGKVISILTD
         CVKFEMPNTERPAYDYLDHCFDSVLSEFEMINTNGWSPKGYKVLGIFEEPEEFTEGLFLNTAVYEYKLSNDRWEVKT
         SGYQTFDKEFENEAYLMKKLDNFLKKPESHFFKYGKRAGEYGLKLGKEEIINYFHVVEDLADFRQLGIKKHKELPLI
         FDSFSLKPKRAYYTHLNEDIELSLNNIKDRLFETSPIDITMEYGCYNDDFEWQCFDNRKKTARELLTIPKISDIKKE
         KKEKRRKTQNDFIKNKREILSVLQKQIKENINLFPFDKFTMKEGSNGGHNARDYGIEKMRDLLNERGIKPAA"
ORIGIN
   1     CGAATCTCACTTTGTTCGATTAACCCCAATTCTTTTTATGAGTCGGGAAATATTTTTGTA

61     GCATAACTTCATTGTGACTTGTCACACTTTTCCTCAAATGTTAAAAATGACATATTGTGT

121     TGTTTTTTAATTGAAAATGATTTAAAATTAATTTATGTAATTCATCACAATATGGAAGGA

181     AGTTTTAAGTTTGAAAAAACTCACAACTATAACAGTTGATACTCGAGCCAAAAAAAAGA

241     TTTGATAGAGTGTCACATAGGTTGGGAACAAAAAACGCAACTGAAACACTTACAAAACTA

301     ATTGATTACTTTGAAAAAGCTGATGATAAGCTATTCATTGAGTTGCATGATTTCTTTTAT

361     GAAACGATGAAAAGCAAATACGAGGATAGTTAGGTATGGCTAAAATCCACCCTTACCCTC

421     AATACGTTAGGAAAATTATTTGTACAGATTGTGGATGTATAATAGAAAAAAACATTAATT

481     ATAAACCGCCTAAAAATAATTATTTTCAGAAGTGCAATGAAYGCCAAAGTCCAAACACTA

541     TTGTTTCTTACAAAGAGAAAAGAGATAAAAAGAAACATAATATGGAGTGATTTAATTTG

601     AAGAAGAAGAAGACACTTTATAAAGAGATAAGAGAATTAGGTTTTGATGTTAATTTTTCA

661     AGGAAAGTCTCACGAAGAAAGATGGTGCATTTGATAAAGTTCGTTTGGAAGAGCTTTTA

721     TTTAAATATAAAGGTGATGCATCTTTGGTAGAAAAAGTATTCMATGGTAATCAAAGTCTT

781     ACTAAAAAAGAGATCAGTAAATTTATTAACGCCGAARGAAGAGAAAGGAAATTTTTTAAA

841     GGAAGATACGCTGGTGAGTTCTCCACGAAAGAAAGAAGCATTTTAGAAAAAACATTAAGT

901     TCAAGCGGATTAAAAGAAGTTAATCGTTTATTGAAAAACAATACTATAGATATATTAAGT

961     AGAACAGAAGAGTTCAAACAATTTATTGGTAGAGGTAAAAAAACCACCAAAGCATATGATT

1021     AAAGATATTAAACGAATAAATAAATTCATGGGAGCAAGTCCGAACGGACAGCCAGGTTTA

1081     TTTGTTGTAAGGGAAATGTACATCAATGGTTTGACTGAATTAGAAGCTATTGAACTTATA

1141     AAGGACAGGCAAAGTCCAGTTGATAAAGATACGGTTTTTTATAGTTGATTAAAAATCACA

1201     GTGAAGGTGGAATAAAATATGATGAATGATACAGAGAAAACTATTTTTAATGCTATTGAA

1261     AATTTTCAAACTGAACATGGTTATAGTCCTTCCTTAACAGAACTAGAAGAAGAAACATTT

1321     TATTCACGTAGCACTGTGAGGCATTGCATAAAAACTTTAGAAGAAAAGGATATTTAGAA

1381     TTGGATAGACAAGTAAGAAGGAATATCCGTTTGCGTAATATGTCAGCTATTATAAAAGAT

1441     GTTAAAGAAAATATTAATGATGATAGTAAGGTTATAAGTGTAGATGTAATTATAGATATT

1501     TTAAATATTTTACATAACGAATTATCTAATGACAATAGAACAAAAAGAATAATTTAATTC
```

```
1561  TAAAGACTAACTTTCAGGTTAGTCTTTTTATTTACCTAAAAATGTCACATTGTGTCACA
1621  GTACACTATATATTGTGTTTTATTTTTTAGTTATATACTAAATGTAGAAAAACAAAAGGG
1681  GTGTAACAAATGAAAATCCATGATAAGAAATTTGAAATTGATAAAGAATTATCGGATGCA

1741  ATTTGTTGGGAGTTGTCGGAATATCAAACAATAATAaCTTTAGCTTTGACTaATTGTAGC
1801  AAAGATGAAGTTTTGAAAATATCACAATTGGTTGATAGAAATGAACGTTTTTCTGAAACA
1861  ACTAAAGAATGGTTGAAAGAAACTATAAATAAATTCCATAAACCTATATGGGAGATGGAA
1921  TTAAAAAATAATAAAACAGAATTAAAAATAGCACAAAATGTTTAAATCAGTATCAAAAAT

1981  ATATCGTGATTCACTAAAGCAAAACATTAAACTTAATGACGAAAATGCAGAATTAAGAGA
2041  ACAAAACATTTTGTTGAAAAGAAAGTTAGCGAAAAGTGAATCACTTTTATATCAACTACA
2101  AAATGATAGGAGTGTCACGAATGGACTCATTAAAAGTAGTAGAAGAAAAACCGAAATTTA

2161  GATTAGGAGATTTCCAATTCTTTGCAAAGAAGAAAGAAGAGGGAGAAGAGGAAGACCTAG

2221  AAGACGTTGAGGAAGAGTATGAAGAAGGTGAAGACGTACCGAAACCTAAACGTAAACCAA
2281  AATCAAAAGCGAGGAGGAAGCACCAGCATGGGCGCAAAAGATAATCGACTTAGTAACCC

2341  CGAAAGCGGAGGAACAGAACCAAAAACAGAAAGTACCAGTACCCGAAGCACCAGTAGTGG
2401  AGGAAGAGGAAGAAGAGGAGCAGCCGCAACAGGAGGGAGCAGTGAAAAGATTCCTAAGGC
2461  AACTTTGGTAGAAGTGCCGGGTCAAGAAAAATCTCCCGAGGATGCAAAAAAGGAAGAACA

2521  ACGTAAGGCAGCAGCCGCACGAAAACGAAAATCACGTGCAGCAGCCAATACGAAAAAGAA
2581  AGCAAGTGCATCCGTTGGCGATGCAACGCAATTAARAGYGTTGGTGCTTACAACTTCAAA
2641  TATCATCGCTGCAAGAGAAGGTATGGCGATGTGGGCAATGAGTSAGCAAGAAGTGGACCA
2701  AATTATAACACCTCTTTACAGCATCCTGTCACGTAATGACGGGTTGGGAGAAGTCATGGG
2761  TGAATATGCCGACCACATTGCTTTAATCGTGGCAGCATTTACTATATTTGTACCAAAATT
2821  CATGATGTGGAAAGCATCAAGACCGAAGAAGGAGGGAACGCATTATGCTAGACCAAATCA

2881  AAGTACCAAACGAGAACAAGGGAAGCAAACAGGAGAGGTTGCAGCTGGTAGTGGACCAAG
2941  TGGTGGACAGTCTACCAACAACGGTACGACTTTTGGCAGGGAGCTATCTCAACTCATTCC
3001  GCCAAGTGCTGGAATCTGAGCAGCAGGACATTGACGGAAACATTGATAACGCTTTGTCAC
3061  GCCTACGTGAGTACATCGACTATATTCAATATGGTCACGATCAAGAAAATGAGTAGGTGA

3121  TTTCATGGAACGTATCCCTACAGACCAACATGTATTTATCACAGGACAAACGGGGACAGG

3181  AAAATCTTTTCTTGCTGAAACGTATTTAGCGGGCTATGAACATGTAGTCAAGCTGGACAC
3241  AAAAGGTGAAGTGTTTGAAAGACGAAAAAGAAACAACCTGTATGGCGTGGGTTACGGGA
3301  AGGAAAGGACTTTACGGTCATAGAGCGTTTAGCGGACATTGATGATGTAGAAACAAAGAA
3361  AATCATTTATGCTCCTGTTTTCCAAGAACAAGAAATGGAATACTATGACGCGTTGATGCA
3421  ATGGGTGTACAGGAGAGAAAACACACAATTATGGGTTGATGAACTCATGGAGGTATGCCC
3481  GAGTCCTTTCAAATACCCTCCTTACTTAAAAGGTTTAATGACTAGGGGCGTTCAAAAGA
3541  AGCTACTGTATGGGCTTGTACGCAACGCCCAAGTGACATTCCTTCTATTGTAATGGGGAA
3601  CAGTGACCACTTTTTCGTCTTTGACCAAAACTTGCCTAGTGACCGTAAGAAGTTATGTGA
```

```
3661 AACAACGGGTAGTTCTGAATTTATGGAATTACCGGGCTATCGTAACTTCTGGTATTTCAA

3721 GCGTGGATGGAGTGACCCCGTACTTGCGACATTGAAAGTG TGA CCTTGAAAGGGGTGCT

3781 ATAGTGGAGGGGAAATTTGCAGGGATTGGACTCAAAAATATACTCGCTATCTTTTTCTTA

3841 TTCATTGTTTTCATTGTGATGGCTAAAGTTGTTTTGACGAAATATCCCATCAAAGGAATT

3901 TCAGAAGTAATTCAAACAGTAT*AGGAGGGAA*TAGGCTA TGA ATCTATTTAGCCCTAAATG

3961 GTGGATTTCAAGTTTAATTGCCGCTTTCATGGCAATGTTCATGATTTAYCTAGTAAAACA

4021 AATTGCATCAAAAGCAAACATTCCGTTTGTATCAAAAGTAACTGAGG*AGGCTT*ACAAGT A

4081 A TGGCAGAACAACAAATTTCAGCACAAGCACGTGCGGCGAACTTTGCAACCGCAACACGA

4141 CAAAACTATCAAATGTTACCATCACAACAAGTCAGGGAAGAAAGCAGCACAATCGAATTT

4201 ACATTACCAAAAGCACGTCTATTATCAAAGATTATTTTAAATGTGGAAGCCGTAGCGACT

4261 CTAAAGAGTAAAGGGACTGCCATCCAAACGCACGACTTCACACCTTATCCTATTTTACGA

4321 CGTGTATCACTAGACCTCAATAACGGATTTAGTCCATTTATTGTGAGTGGTCGTGACCTT

4381 GTACAATACAACATGCTGCGTTTAAATCCAAACGTATTATTCCCAAGTACAAATCCACGT

4441 GCGATGAACTATGTGGAAAACGGGGCTAGTCCTGAGGGTAAAGATGCAAAGATTAAGTTT

4501 TCAGTAGAGTTACCTATCACATTGAATCCACGTGACCCTGTAGGTCTTATCTTGCTGCAA

4561 AACCCTGAGACAAGCGTGACATTAACAGTGGATGTCGAAACATTAGCAAAAGCGTATAGC

4621 TTGAATGCATCGAATGCCGACCAAGTTTTATTTAAATCGATGAAAGTTACACCGATGTTA

4681 GAAGCGTTTAACATTCCACCTGTTCCGCAAGCGTTCCCTGATATTTCTACACTGAAACTC

4741 GTTTCTAGTAAATCAGATACATTCTCGGGTAATGGTCAAAACATCTTGAAATTAAACACA

4801 GGTACAATCTATCGTAAGTTAATTTTATTCATTGAAGATAAAAACGGAAACCCGCTTGCG

4861 GATGAAGATTTCCAAGGCAACTTAGAACTCGTGTTTAACCAAGCGGACATCCCGTATAGC

4921 ATCAAGCCCGAAATATTGGCTCATATCAATCACAGTCAATTAGGGTACGCACTTCCAAAA

4981 GGTATGTACGCCTTTGACTTTACAAATCAAGGGATTCCGAATTTAGGCGGTAGCCGTGAC

5041 TTTATCGATACGGAACGTTTAACAGAATTCTGGCTACGATTCAGTACGCAAAAAGAGGGT

5101 AAAGTGACGGTTGTTTCTGAGAACTTGTCACGCTTACGT TAA AAAGAAG<u>AGGGGATTTCC</u>

5161 <u>CCTTTTCTT</u>CTATATAAG*GAGGGATA*GTGCA TGG CAGGTGAATTAAGTCATTTCAAAAAA

5221 GACCTGTATCCAAATTTAGGTTTTGAAAATACATCTTACTTATCAATTCCCGAAGCCGAA

5281 GACCAACAAGCAATGGTAGATGACCAAAAGGTTGCTGAGGAAACCGCAAGGACATCAAAC

5341 AAAGCGGGTCACAAAAACATCATGCTCGGGATTGTCTTGTTAATTATTATCATGTTCGTA

5401 TT*AGGAAAGGTGTG*ATAACGAT***ACGTAGCACAAATGACACAGTTAATAGGAAACATGG

5461 GTTTCCCTATTTTTACTGCTATTTATTTTATGACGTACATGAAAAAGACGCTTGATACAT

5521 GTACACAATCAATGGTAGCGAATACACAAATCATGATTCGTATTGAAAAGTTTTTAGATG

5581 ATAAGGAGAAGAAATCA XXX GTAAAACATTAATTCTCGTGGTTGCGATTTTCTGTTTATG

5641 GTTTTTCGTAATCAAGAAAAAGA*AAGCGTGA*TGTAAA TGG ATAGAGGGTTAACCTTTTTC

5701 ACATTAGCTTTGCTTCTCATATGGTTAGTCTTTGACGATCTATTCGGTGAAAAGAAATAC

5761 TTGTCTAAATTAGCGGGAGCTATGACACCGAACTTGTCTCTACCTGACCCCGCACGTGAT
```

```
5821  GCGGTAGACAAGGTTGTAGAAGATACAAAGGAAAACGCAAAGAAAGATGTGACAGACATC
5881  AAAAAGGATACAAAGGATGCCGTGAAAGATACAAAGAAATCGTTTGATGATTTCATAAAC
5941  GGTGGTTTTGAAAAGGAAATGAAGAAGGACGTTAACGATTTTAAAGATTGGACAAAAGAC
6001  CTTCCTAATCCTGACAAGATGAAAGAGAAAGCCAATAACGATTTTAAAGCAATATGGGAT
6061  GAAGTCTCCAAAGCGTTAGAGGATACAAAAAAGTCAGCTAACGATATGTGGGATGATGTG
6121  ACATCCTCGGTGAAAGCATGGTTCAAATGAAAAATTTTACGGAGTCCCTCGGTTTTATTG
6181  TAGCGTTTATGGTTATGACAATTTTCATTAGCATGTTTACAAATGAGTCTGTGACAAACG
6241  GATTCTTGCTGCTCGTGCTTGCGTCAATGATGGTCGTAAACGCTGATAAGTTTACAAAAT
6301  TTTTAGATGGGGTGATGAAATAATGGGACGTATTTTAGGTATTATTTCGGGTATTGGTTT
6361  GCTAATTGCTTTGTACTTATTTTTAAGTAACGCACGACAAACAACGCAAATCATTGATAG
6421  CATGGCTGGAAATGCCGTGAGTGGTATTAAAGTATTACAAGGTCGATAAGGAGGGTGTGA
6481  CATGTTAGATGGTACGTATCGCTATCAAGTACAAAATAGACAAGCCTTGCAAGCACTTGA
6541  TAAACGTGTTGAGATTCCCGATGCACGTTTAGGAGTCGGTGCTGCGGAACACTTAGAAGC
6601  AATGGGTATCCGTGTTGTCTATGAAAACAAAGTACCAAAACTGGTTTTACCATCTGTACA
6661  TCGTTTGCCATTCGAGCAAGTTCAACCTAAAAATGTAGAGCCTGACATGTTTGTCACAGA
6721  TGACTTCCATGTCGGCGATGCAATTATGGGGGTGTAGCGAATGGCTGATATTGTACCAGT
6781  AGTTGGCGGGGCGGGGCGGCGGGCATGGCTCGTCCCCTTCTAAAAAGARAAACAACAA
6841  AATGTTATTTATGGTTGGTGGTGTGGTCGTAGTTGTGCTGCTCGTATTCTTGCAACGCTC
6901  GAAGTCATCGGGCGGCAATGTGGACACGCTGCAAAACACGATTCCGATTTCGGATTCGCA
6961  AAGGCTCGACAATTTTCAATCCATTGTGTCAGGTGAGACATCGGCACAAATCAACGGGAT
7021  GATGAAAGATGCACAGGACGGTTGGTCGGGAATGTTCAAGGATTTCAGTGAAAAGATGAC
7081  CAATCAAATGAAAGAAATGGATGACCGCAACAAGGAATACAACAAGCAACAACAGGACTG
7141  GGTGAAGGATTCCTTTACAAATATCAAGGACTCGCTAGGTGTGGGAGCGATTAGAAATGA
7201  CGATAACGCTACCTTCACAATCGGTAACGGGACAACAGGTGCGGCGAAAACATATGACCA
7261  ACAACTGAATGATTTCCGCAATGATCGTCAAAAGTTGGCTGAGGAAATTAAACGTACACA
7321  ATCCGTTATTACATTCCGTAAAAACAACGGATTAGACGTTTCTAATCAAGTCCAACACTA
7381  TAAGAATTTAGGAGCATTGTAAATGCCTGCGGATATTACCCCTTTCATTGCGGATGCGCAA
7441  CGAATTCAAAAACAAACAGGAATCCCAGCTTCTATTATATTAGGTCAAATCATTTTCGAA
7501  TCAAGCGGGAAGTTTCCTGGCGGTTTGTCAGGACTCGCTTATAACAACAAAAACCTTTTC
7561  GGGATTAAAGGAAAGGGGACGGCTGGAACGGCTAATATGTGGTCAAAAGAATATGATCG
7621  GGAGGGAATCGGGTTTCTGGTTTCCGCTCGTACAATTCATGGACAGAATCGCTCAATGAC
7681  CATGCACGGTTGTTGCAAACAGACCGTTACGCAAAGTATTTAAAGAATGCAACATCTGTT
7741  GAAGATTATGCAAATGGATTATAAAAGGCGGTTATGCCACTGACCCAGCTTATGCAAAA
7801  CAACTGTTAGGCATTATTAAATCAAATGGGCTTACAAAATACGATGATGGGAAATACACC
7861  TTTACAGGCGGTGACGTGTCGGGCGGTTCTGCTGGTGGTGGGGGTAGTGGCGGTTCATTC
7921  TTTGCACCGTTATTCAATGCCATTATTCGGGCTTTGCTATTTGTTCTATGTGTCGTGGCT
7981  GCGTTGCTGCTATTCGCAAATGCTTTCCCGAGTGTGGAACAAACAGTGAAATCAGTTGCG
```

```
8041  AAGAAGGTGAAATCA[GAG]TGGTACAAACGGTTTGAAACTCAATAGCAAATTGCAAGAAG
8101  CTTACAACAAAGCTATTGCTAGTGGGTTGCGGTTCACATCGGGATTCCGTTCGGGGTCAA
8161  CTGGTCCGAGTGGGAGACCTGATAGCCATTCCCAAGGCATGGCTATGGATTTTGCGGGAA
8221  GTAAAGCACAAATGAAACAATTTTCCGAGTGGGCGAAAATGACAGGACTCTTTACAGAAG
8281  TGTTGTATGAGACGGCGGGTCATTACGATCATGTCCATGTCGGATGGCAAACTGGAAAAC
8341  ACCCTGACGGAAAAACATATGTaGGCGAcCaCaAACTCATTGATAGAGTAGGTAGCGGGA
8401  CGCTCGGTGACTTGCAAACGGTTGGTGACACGGTTGCTCCTGCTGGTGGCGGAGACAAGG
8461  CGGGGTTTATGTCTTCCCTATTTACTGGCATATTTCGAGTTGTAATGATTGTCATATGTC
8521  TGATTGGCGGGGTCTACTTCATTATGAATGCTTTCCCGCAAATGAAACAATTAATCAAGT

8581  GAGGTGGAAAGAATGGATAGAAAGACAAATAGTACATGGCGGGAGCAAACGCYCACCATA
8641  CCGTCGAAAACAGTATTTGACGTGGTATTCCCTGATACAAAGCCGAACCATTACCACATC
8701  AATAACTTATCGGCTGCACCTATTTATTTAGGGACAACTACACTCGCATCACCAAAGACG
8761  TATGACATTGTTGTAAACGGGAACGGGACAACATGCACGCTCGTGACCTCGGTGTGACT
8821  CGCATAACGCTATATAATGACAGTCCTGATAAGGCTCGAATTGTTTTAACTACGTTCGAA
8881  GACAAGTTTAACCCTGCGGTGCTTGCTGGTCGTGGTGGTAGCGTTACGGTGACAGGTGGT
8941  GGCGGTGGTGCTGGTGGCGTCATTACAGGTTTCAACGCTTCCCTTCCTAGTGGTGACAAT
9001  AATATTGGTCGAGTAAAAGTGACCGAAATGCCTGCAATTGATTTTGTACTCGGTACATTA
9061  CCTGCTGGTACAAACAATATAGGGAAAGTAGAAGTTAGCAAATTACCACCGCTTGCTAGT
9121  GTTGGCGGGAAAATTGGAGATGTCGGAATACAGGGAGGCGTGACGATTACGTCCATGCCC
9181  GCCGTAGAGTTAGAGGTAAGTAAGGACTTGAATGTAAAAGAGAAGTCGTACAACGATTTC
9241  TTCTATCAAGAACCAAATGTAGAGCAAACAGAAGTTGTATTCACAACAGACCTGTCACGT
9301  ATCATTTTTATTTCGAATGATGGACAGAACCCGTTAAAGGTCACGCTTAATAACCGTACC
9361  ATTACATTGCTGCAAAACGAGGTAATAGAAGAACTACCACTACTCACAAAAACAATTAAA
9421  CTAGTGCGACCTAGTGGAAGTGGAAGCGCACGGATCATGGGGGTG[TAG]GTT[ATG]GGACTT

9481  AAGAAACCTGCGGTTGGTGGGAAGAGGGTTGCTAAAGGAATAGGGAAGCCTTTTCAACCT
9541  CAAGGGTCTGCAAGTGGGTTGTTGAAGTGAGAGGACTTTCTTTTAAACCTAGTGTCGTA
9601  GCAACAAAACCTAAAAAATCGCAAATAGATGCGGATTATCCATACAGGGtGGTACAGTT
9661  GGTATAGCAAGAACCGCATTTGAACCACCTTTAGATGAAGACCTTTTAAACATGATTAAC
9721  AATGATGGTGACTATTCTGTAGGTCGTGTTGTTACGTTTTATGATGATGGATTCAAAATA
9781  TATCTTGACAAAGGAAATGAACAACCGTGGGTTGCTTATGAAT*AGGAGAGG*TAAATCA[TG]

9841  TATGTAAATAAAAGAGTTTATTTCGAAAAAGATACAGGTATTGTCGTAATGGTTACGGGT
9901  GGATTTCGTGATGATTGGTTACATTCCCACCCGACAGTGCAAGAGGACATGGCAAAGTAT
9961  TCAGTGCTTGCTGAACGTGTTCCAGATACTTTAAGCATGTTGGAATTAAAAGAAGGAACG
10021 TATGATGAGGAATTTTCAAAGGCTCGTAGTTTCAAAGTAGATGTGAAAACAAATACGATT
10081 GTGTTTGATTTTACACCCGAAGATAAAAAGGAAGTAGAAGAGAAAAAGACACCGGAACAT
10141 CGTGTAACGATGGTTGAAAGTGCAATTAACGATATATTACT*AGGAGGAAT*GT[ATA]ATGAC
10201 TTTATCGGGATTAGCTGCTTATATTTTAAATCAATGGTTATTAGGTAAATTTACAAATAG
```

```
10261 TGATTTAAATACGCTCGTGGATCGTGGACGTATTACAGAAGAACACCGTGTCTACTTCTT

10321 ATCAATGAAGGAGGAGAAATAATATGTATTATCACAATCGAAATCTAGCAAACCTAGAGA

10381 AGTTAGCACCGCATACAAGACAGAAAGCAAAACAGTGGTATCAATATTGTGTAGAAAACG

10441 GTATTGAGGTACTAATCTATGAAACAACTCGTACCATCGAACAACAACGTGAGAACGTAC

10501 GTAAAGGCGCGTCACAAACTATGAAGTCATACCACTTAGTAGGACAAGCTTTGGATTTCG

10561 TACCAGCAAGAGAAGCCGAGGTATATTGGGATGGATACTATAGAAACGACATTCAAAAGG

10621 CTATCGGGTATGCGAAGTCTATCGGTTTTGAATGGGGTGGTGACTGGAAAGGGTTTGTTG

10681 ATAGTCCACRCTTACARTACAACTATAACGGTTACGGGACGGACAAAGGAAACGTGTCAG

10741 ATGAGCCTGTACACGTGACAGGGAATACAGGGGTTGTAAGAGTTGTTGTTGATAGCGCAC

10801 TTGTCAGAAGAGAGCCTACAACACAATCACCTATCAATACGGATGCTGGAGAAAATGGTC

10861 GCTTATATCGTGGTACTGAATGGCAAGCGTGGGGAAGTACAATTGGTGAAGGTGGTTATA

10921 CATGGTATCCATTAGGAAATGAAATGTGGGTACGTGGTGATTTAGTAAGTTGGAGAAATG

10981 CATAAAATGAAAAAAGAGTCGTGATGAATCACGGCTCTTTTAACGTAATTTGTAAAAA

11041 AGAAAAAATTGATAACAAAATTGACACATGATATAATCAAGTTGTTCCATTACTTAATAT

11101 AAACAAGATAAACCGTTCTGATTTTGTTTATGTTAAGTAATCATTTCAAAGTAAATATTT

11161 CGTGGATATTTATTTTGTGACTTTCATTGTGAACTTATCAAATGGAAATAAATTTATGTT

11221 TTCTTTTATTTGTTTTTGTCGCTTTATAAAGTGACTTCTTCTTCTTCGACTCGCTAATAG

11281 CGGGTCTTTTTTTTGTTCATAAAAAAGAGAGTAGACATTCGTGGTATCTACTCTCTTTGC

11341 ATCAAGCTGCTGGTTTTATTCCCCTTTCATTTAATAGGTCACGCATTTTTTCGATTCCGT

11401 AATCCCTTGCGTTGTGACCTCCATTGCTGCCTTCCTTCATTGTGAATTTATCAAATGGAA

11461 ATAAATTTATATTTTCTTTATTTGTTTTTGTAAGACTGATAATATTTCACGTTTATTTT

11521 TTATGAAATCATTTTGTGTTTTTCTTCTTTTTTCTTTCTTCTCTTTTTTAATATCAGAAA

11581 TCTTTGGTATTGTTAATAATTCTCTTGCTGTTTTTTTTCTGTTATCAAAACATTGCCATT

11641 CGAAATCATCATTATAGCAACCGTATTCCATTGTTATATCTATTGGTGATGTTTCAAATA

11701 ATCTATCTTTAATATTATTTAAACTTAATTCTATGTCTTCGTTTAAATGTGTATAATACG

11761 CTCGTTTAGGTTTCAAAGAGAAACTATCAAATATAAGGGGTAATTCCTTATGTTTTTTA

11821 TTCCTAGTTGCCTAAAATCAGCTAAATCTTCAACAACATGAAAATAATTTATAATTTCTT

11881 CTTTACCTAATTTTAAACCGTATTCCCCTGCACGTTTTCATATTTAAAGAAATGGGATT

11941 CTGGTTTCTTCAAGAAGTTATCTAATTTCTTCATTAGGTAAGCTTCGTTTTCAAATTCCT

12001 TATCAAATGTTTGATAACCCGATGTTTAACTTCCCATCTGTCATTAGATAATTTGTATT

12061 CATACACTGCCGTATTTAAAAATAAACCCTCTGTAAATTCTTCTGGTTCTTCAAAGATAC

12121 CTAGAACTTTATACCCTTTAGGACTCCACCCATTTGTGTTTATCATTTCAAATTCGGATA

12181 ATACACTATCAAAACAATGATCCAAATAATCATATGCTGGTCTTTCTGTGTTAGGCATTT

12241 CGAACTTAACACAATCTGTTAAAATGGAAATTACCTTACCGCCATTTCTTTCTATGTTTA

12301 ACGCTCCTTCTTGCACTCTTATTCTACCGAATGCGGTTATCATAGACGATACAATCGGAT

12361 TAAACATATAACCTACATCGAATCCAGCGAAATATATTTCCTGCTCACCATCTTCATTTT

12421 CTGAACAAGCATACTGTTGAAAGGCTTGAAAGAACTTTCCGTATATAGCATTCGTAATTA

12481 ATTTAACAATATACTCGGAATGATTTCCTATATCTCTTAGTTTCAAACGTAGTTCCCAAA

12541 GTATATCAATTACTTTACTAATTGGATGTAATTTTCCGTCGGTTTCGATAACAACAACTT
```

```
12601 CAATGATTTCTTTAATAACTTCATTGTGTTTATCTTTATCAATTTGTGACAAAAGAAACT

12661 CTACTTCTTTGTAATGAACTGTAGTCACAAAATTACCAAAACCTAAAACGTTACGCCTTA

12721 TTTGATTTACAGTTCCTTCTTCTCCCTTTTGTTTAATCATAATTGTATGTCTAACATCAG

12781 GAGGTATTTCGAATTCACAAGTTAACATAACGATACGTTTTAAACTAGGTTTAGGAATTT

12841 CAGTAAAATCTTTTATGTTATCAAAGTATTGAACCCTGCTATTTCTCAAATCAGGAATAC

12901 AATAACGCATAATTGCGGGATAACTAGCACCTATATCAGTGTTTGCTCCCCTTGCTATAT

12961 AACCAACTTTTTCATGCTCAATTATAGCTCCTTGGTTAGCATCAAAACTTAAATTGATAG

13021 CCTTCGCTATGATATCAACATCAATATCTTTTTCTTGCCAATCATTCATAGTTGAATCAA

13081 TTGAAAAAGTTTTCAACTCATTTTCATCTAAAACTTTAGCAATAGCCGCTTCGGATAATG

13141 TACCCGCCGAATAAAAGAATTAGGAAAACAACCGAAACTTTCTTTAAACATATTCATCA

13201 CGACATAAATTAAATCCTTAGATAAAAAGAATTATACATGTTTTCCCTTAAAATCTTTT

13261 TAACATAAGTATTATCTTGTAACTTATGATTATTTTTATCTACCTTTTGTTATATCCAT

13321 TCAAAATAAATCCCAATTAATTTTACTTTCTTTTATTTCTTCGGCATATTTAAGGTTTG

13381 CATTTCTAGCACATTCGATAGGAGTCTTTTGCCAAAATGGTTTAGAACGAAAAGTATTAC

13441 ATTTACTCATCTTTTTGTTTTTTATAACAAATAATTCTAGATTGCCATTTAAAACTTTAG

13501 ATACCCCTATACTTTCACCATTGCCGATATCTAATTCTATAATGGGAGGTTCTGTCCACG

13561 AACCACTTTTCTTATGAAATTTTCCGTTTATACCTTTAAAACTCTTTGGAATATTTTCA

13621 CCTGTTCATCTTGTTCTAAGTATTTTCTTTTCATTAATAACTTTAAAATAAGGATTGATT

13681 CAATTTCATTAAAGTGACAAATAATTTTATTATTAAAATGACAATCTTTAATGATATTTT

13741 TCAGCATGTAAATAACCGATAAATCCATATCCTTTTCGTTTTCCCGATAAATATAGTGAT

13801 ATCCGTTTTTCTTTGTCACAGGATTGTACGAGCAAAAACCAAATAACATAATTTCTCCAG

13861 TCACTTCATCAATTTCAAATTTAAATCCATATAACCCTTTAGGTTTATCTGAATATAAAT

13921 ATTCCGTTGGCTTCGGACTTGAAAAGTATGTACATTAGATAGATGAACTTCCATCTCTG

13981 AATATTCTAGCTTGTCCAATCCTTCGACACCTAAAAACGAAGGATTTATTTTTTTCATTT

14041 ACATAACTTACCTCCTTTTCAAAAAACATAACTTACAAGCACAATTATAGCACATAAAAA

14101 ATGWAATCACGTCATATAATTCTATATTAAGAGAAAAAATAAaTTGAAATCAGTTAAATA

14161 ATAATTAAATCAGTAAAACTGAATATGATTTTATGTCACAAATAATAAGATTAAGAGAGT

14221 GTGACAAGTCACAATGAAGTTATGCTACAAAAATATTTCCCGACTCATAAAAAGAATTGG

14281 GGTTAATCGAACAAAGTGAGATTCGTAATTCGGCTCGAG
```

We claim:

1. A method of identifying or detecting *Bacillus anthracis* in a sample, the method comprising: (a) providing a sample suspected of containing *Bacillus anthracis*; (b) contacting the sample with a recombinant, Wip1 p23 receptor binding protein comprising the sequence of SEQ ID NO:23, wherein the recombinant Wip1 p23 receptor binding protein comprises a reporter molecule, the method comprising mixing the recombinant Wip1 p23 receptor binding protein and the sample to form a complex comprising the Wip1 p23 receptor binding protein and the *Bacillus anthracis* if the *Bacillus anthracis* is present, and detecting a signal from the reporter molecule in the complex to detect the presence of *Bacillus anthracis* in the sample.

2. The method according to claim 1, wherein the sample is a biological sample or environmental sample.

3. The method according to claim 1, wherein the reporter molecule is a fluorophore or fluorophore/quencher pair.

4. The method according to claim 1, wherein the recombinant Wip1 p23 receptor binding protein changes conformation when contacting a *Bacillus anthracis* receptor in the complex, thereby changing detectable properties of the recombinant protein to produce the signal.

* * * * *

SEQUENCE LISTING

<160> NUMBER OF SEQ ID NOS: 28

<210> SEQ ID NO 1
<211> LENGTH: 51
<212> TYPE: PRT
<213> ORGANISM: Bacillus phage Wip1
<220> FEATURE:
<221> NAME/KEY: misc_feature
<222> LOCATION: (43)..(43)
<223> OTHER INFORMATION: Xaa can be any naturally occurring amino acid

<400> SEQUENCE: 1

Met Ala Lys Ile His Pro Tyr Pro Gln Tyr Val Arg Lys Ile Ile Cys

```
                1               5                  10                 15
              Thr Asp Cys Gly Cys Ile Ile Glu Lys Asn Ile Asn Tyr Lys Pro Pro
                              20                 25                 30

Lys Asn Asn Tyr Phe Gln Lys Cys Asn Glu Xaa Gln Ser Pro Asn Thr
                      35                 40                 45

Ile Val Ser
                      50

<210> SEQ ID NO 2
<211> LENGTH: 196
<212> TYPE: PRT
<213> ORGANISM: Bacillus phage Wip1

<400> SEQUENCE: 2

Leu Lys Lys Lys Lys Thr Leu Tyr Lys Glu Ile Arg Glu Leu Gly Phe
1               5                  10                 15

Asp Val Asn Phe Ser Arg Lys Val Ser Arg Arg Lys Asp Gly Ala Phe
                20                 25                 30

Asp Lys Val Arg Leu Glu Glu Leu Phe Lys Tyr Lys Gly Asp Ala
        35                 40                 45

Ser Leu Val Glu Lys Val Phe His Gly Asn Gln Ser Leu Thr Lys Lys
    50                 55                 60

Glu Ile Ser Lys Phe Ile Asn Ala Glu Arg Arg Glu Arg Lys Phe Phe
65                  70                 75                  80

Lys Gly Arg Tyr Ala Gly Glu Phe Ser Thr Lys Glu Arg Ser Ile Leu
                85                 90                 95

Glu Lys Thr Leu Ser Ser Ser Gly Leu Lys Glu Val Asn Arg Leu Leu
            100                105                110

Lys Asn Asn Thr Ile Asp Ile Leu Ser Arg Thr Glu Glu Phe Lys Gln
        115                120                125

Phe Ile Gly Arg Gly Lys Lys Pro Lys His Met Ile Lys Asp Ile
    130                135                140

Lys Arg Ile Asn Lys Phe Met Gly Ala Ser Pro Asn Gly Gln Pro Gly
145                 150                155                 160

Leu Phe Val Val Arg Glu Met Tyr Ile Asn Gly Leu Thr Glu Leu Glu
                165                170                175

Ala Ile Glu Leu Ile Lys Asp Arg Gln Ser Pro Val Asp Lys Asp Thr
            180                185                190

Val Phe Tyr Ser
            195

<210> SEQ ID NO 3
<211> LENGTH: 112
<212> TYPE: PRT
<213> ORGANISM: Bacillus phage Wip1

<400> SEQUENCE: 3

Met Met Asn Asp Thr Glu Lys Thr Ile Phe Asn Ala Ile Glu Asn Phe
1               5                  10                 15

Gln Thr Glu His Gly Tyr Ser Pro Ser Leu Thr Glu Leu Gly Glu Glu
                20                 25                 30

Thr Phe Tyr Ser Arg Ser Thr Val Arg His Cys Ile Lys Thr Leu Glu
        35                 40                 45

Glu Lys Gly Tyr Leu Glu Leu Asp Arg Gln Val Arg Arg Asn Ile Arg
    50                 55                 60

Leu Arg Asn Met Ser Ala Ile Ile Lys Asp Val Lys Glu Asn Ile Asn
```

```
                65                  70                  75                  80
Asp Asp Ser Lys Val Ile Ser Val Asp Val Ile Ile Asp Ile Leu Asn
                85                  90                  95

Ile Leu His Asn Glu Leu Ser Asn Asp Asn Arg Thr Lys Arg Ile Ile
            100                 105                 110
```

<210> SEQ ID NO 4
<211> LENGTH: 91
<212> TYPE: PRT
<213> ORGANISM: Bacillus phage Wip1

<400> SEQUENCE: 4

```
Met Lys Ile His Asp Lys Lys Phe Glu Ile Asp Lys Glu Leu Ser Asp
1               5                   10                  15

Ala Ile Cys Trp Glu Leu Ser Glu Tyr Gln Thr Ile Ile Thr Leu Ala
                20                  25                  30

Leu Thr Asn Cys Ser Lys Asp Glu Val Leu Lys Ile Ser Gln Leu Val
            35                  40                  45

Asp Arg Asn Glu Arg Phe Ser Glu Thr Thr Lys Glu Trp Leu Lys Glu
        50                  55                  60

Thr Ile Asn Lys Phe His Lys Pro Ile Trp Glu Met Glu Leu Lys Asn
65                  70                  75                  80

Asn Lys Thr Glu Leu Lys Ile Ala Gln Asn Val
                85                  90
```

<210> SEQ ID NO 5
<211> LENGTH: 67
<212> TYPE: PRT
<213> ORGANISM: Bacillus phage Wip1

<400> SEQUENCE: 5

```
Met Phe Lys Ser Val Ser Lys Ile Tyr Arg Asp Ser Leu Lys Gln Asn
1               5                   10                  15

Ile Lys Leu Asn Asp Glu Asn Ala Glu Leu Arg Glu Gln Asn Ile Leu
                20                  25                  30

Leu Lys Arg Lys Leu Ala Lys Ser Glu Ser Leu Leu Tyr Gln Leu Gln
            35                  40                  45

Asn Asp Arg Ser Val Thr Asn Gly Leu Ile Lys Ser Ser Arg Arg Lys
        50                  55                  60

Thr Glu Ile
65
```

<210> SEQ ID NO 6
<211> LENGTH: 116
<212> TYPE: PRT
<213> ORGANISM: Bacillus phage Wip1

<400> SEQUENCE: 6

```
Met Asp Ser Leu Lys Val Val Glu Glu Lys Pro Lys Phe Arg Leu Gly
1               5                   10                  15

Asp Phe Gln Phe Phe Ala Lys Lys Lys Glu Glu Gly Glu Glu Glu Asp
                20                  25                  30

Leu Glu Asp Val Glu Glu Glu Tyr Glu Glu Gly Glu Asp Val Pro Lys
            35                  40                  45

Pro Lys Arg Lys Pro Lys Ser Lys Ser Glu Glu Glu Ala Pro Ala Trp
        50                  55                  60

Ala Gln Lys Ile Ile Asp Leu Val Thr Pro Lys Ala Glu Glu Gln Asn
65                  70                  75                  80
```

```
Gln Lys Gln Lys Val Pro Val Pro Glu Ala Pro Val Glu Glu
            85                  90                  95

Glu Glu Glu Glu Gln Pro Gln Glu Gly Ala Val Lys Arg Phe Leu
            100                 105                 110

Arg Gln Leu Trp
        115

<210> SEQ ID NO 7
<211> LENGTH: 236
<212> TYPE: PRT
<213> ORGANISM: Bacillus phage Wip1

<400> SEQUENCE: 7

Met Gly Ala Lys Asp Asn Arg Leu Ser Asn Pro Glu Ser Gly Gly Thr
1               5                   10                  15

Glu Pro Lys Thr Glu Ser Thr Ser Thr Arg Ser Thr Ser Ser Gly Gly
            20                  25                  30

Arg Gly Arg Arg Gly Ala Ala Thr Gly Gly Ser Ser Glu Lys Ile
        35                  40                  45

Pro Lys Ala Thr Leu Val Glu Val Pro Gly Gln Glu Lys Ser Pro Glu
    50                  55                  60

Asp Ala Lys Lys Glu Glu Gln Arg Lys Ala Ala Ala Arg Lys Arg
65                  70                  75                  80

Lys Ser Arg Ala Ala Ala Asn Thr Lys Lys Ala Ser Ala Ser Val
            85                  90                  95

Gly Asp Ala Thr Gln Leu Thr Ala Leu Val Leu Thr Thr Ser Asn Ile
            100                 105                 110

Ile Ala Ala Arg Glu Gly Met Ala Met Trp Ala Met Ser Gln Gln Glu
        115                 120                 125

Val Asp Gln Ile Ile Thr Pro Leu Tyr Ser Ile Leu Ser Arg Asn Asp
    130                 135                 140

Gly Leu Gly Glu Val Met Gly Glu Tyr Ala Asp His Ile Ala Leu Ile
145                 150                 155                 160

Val Ala Ala Phe Thr Ile Phe Val Pro Lys Phe Met Met Trp Lys Ala
                165                 170                 175

Ser Arg Pro Lys Lys Glu Gly Thr His Tyr Ala Arg Pro Asn Gln Ser
            180                 185                 190

Thr Lys Arg Glu Gln Gly Lys Gln Thr Gly Glu Val Ala Ala Gly Ser
        195                 200                 205

Gly Pro Ser Gly Gly Gln Ser Thr Asn Asn Gly Thr Thr Phe Gly Arg
    210                 215                 220

Glu Leu Ser Gln Leu Ile Pro Pro Ser Ala Gly Ile
225                 230                 235

<210> SEQ ID NO 8
<211> LENGTH: 83
<212> TYPE: PRT
<213> ORGANISM: Bacillus phage Wip1

<400> SEQUENCE: 8

Met Leu Asp Gln Ile Lys Val Pro Asn Glu Asn Lys Gly Ser Lys Gln
1               5                   10                  15

Glu Arg Leu Gln Leu Val Val Asp Gln Val Val Asp Ser Leu Pro Thr
            20                  25                  30

Thr Val Arg Leu Leu Ala Gly Ser Tyr Leu Asn Ser Phe Arg Gln Val
        35                  40                  45
```

Leu Glu Ser Glu Gln Gln Asp Ile Asp Gly Asn Ile Asp Asn Ala Leu
            50                  55                  60

Ser Arg Leu Arg Glu Tyr Ile Asp Tyr Ile Gln Tyr Gly His Asp Gln
65                  70                  75                  80

Glu Asn Glu

<210> SEQ ID NO 9
<211> LENGTH: 212
<212> TYPE: PRT
<213> ORGANISM: Bacillus phage Wip1

<400> SEQUENCE: 9

Met Glu Arg Ile Pro Thr Asp Gln His Val Phe Ile Thr Gly Gln Thr
1               5                   10                  15

Gly Thr Gly Lys Ser Phe Leu Ala Glu Thr Tyr Leu Ala Gly Tyr Glu
            20                  25                  30

His Val Val Lys Leu Asp Thr Lys Gly Glu Val Phe Glu Arg Arg Lys
        35                  40                  45

Lys Lys Gln Pro Val Trp Arg Gly Leu Arg Glu Gly Lys Asp Phe Thr
    50                  55                  60

Val Ile Glu Arg Leu Ala Asp Ile Asp Asp Val Glu Thr Lys Lys Ile
65                  70                  75                  80

Ile Tyr Ala Pro Val Phe Gln Glu Gln Glu Met Glu Tyr Tyr Asp Ala
                85                  90                  95

Leu Met Gln Trp Val Tyr Arg Arg Glu Asn Thr Gln Leu Trp Val Asp
            100                 105                 110

Glu Leu Met Glu Val Cys Pro Ser Pro Phe Lys Tyr Pro Pro Tyr Leu
        115                 120                 125

Lys Gly Leu Met Thr Arg Gly Arg Ser Lys Glu Ala Thr Val Trp Ala
    130                 135                 140

Cys Thr Gln Arg Pro Ser Asp Ile Pro Ser Ile Val Met Gly Asn Ser
145                 150                 155                 160

Asp His Phe Phe Val Phe Asp Gln Asn Leu Pro Ser Asp Arg Lys Lys
                165                 170                 175

Leu Cys Glu Thr Thr Gly Ser Ser Glu Phe Met Glu Leu Pro Gly Tyr
            180                 185                 190

Arg Asn Phe Trp Tyr Phe Lys Arg Gly Trp Ser Asp Pro Val Leu Ala
        195                 200                 205

Thr Leu Lys Val
    210

<210> SEQ ID NO 10
<211> LENGTH: 54
<212> TYPE: PRT
<213> ORGANISM: Bacillus phage Wip1

<400> SEQUENCE: 10

Val Thr Leu Lys Gly Gly Ala Ile Val Glu Gly Lys Phe Ala Gly Ile
1               5                   10                  15

Gly Leu Lys Asn Ile Leu Ala Ile Phe Phe Leu Phe Ile Val Phe Ile
            20                  25                  30

Val Met Ala Lys Val Val Leu Thr Lys Tyr Pro Ile Lys Gly Ile Ser
        35                  40                  45

Glu Val Ile Gln Thr Val
    50

<210> SEQ ID NO 11
<211> LENGTH: 47
<212> TYPE: PRT
<213> ORGANISM: Bacillus phage Wip1

<400> SEQUENCE: 11

Met Asn Leu Phe Ser Pro Lys Trp Trp Ile Ser Ser Leu Ile Ala Ala
1               5                   10                  15

Phe Met Ala Met Phe Met Ile Tyr Leu Val Lys Gln Ile Ala Ser Lys
            20                  25                  30

Ala Asn Ile Pro Phe Val Ser Lys Val Thr Glu Glu Ala Tyr Lys
        35                  40                  45

<210> SEQ ID NO 12
<211> LENGTH: 353
<212> TYPE: PRT
<213> ORGANISM: Bacillus phage Wip1

<400> SEQUENCE: 12

Met Ala Glu Gln Gln Ile Ser Ala Gln Ala Arg Ala Ala Asn Phe Ala
1               5                   10                  15

Thr Ala Thr Arg Gln Asn Tyr Gln Met Leu Pro Ser Gln Val Arg
            20                  25                  30

Glu Glu Ser Ser Thr Ile Glu Phe Thr Leu Pro Lys Ala Arg Leu Leu
            35                  40                  45

Ser Lys Ile Ile Leu Asn Val Glu Ala Val Ala Thr Leu Lys Ser Lys
    50                  55                  60

Gly Thr Ala Ile Gln Thr His Asp Phe Thr Pro Tyr Pro Ile Leu Arg
65                  70                  75                  80

Arg Val Ser Leu Asp Leu Asn Asn Gly Phe Ser Pro Phe Ile Val Ser
                85                  90                  95

Gly Arg Asp Leu Val Gln Tyr Asn Met Leu Arg Leu Asn Pro Asn Val
            100                 105                 110

Leu Phe Pro Ser Thr Asn Pro Arg Ala Met Asn Tyr Val Glu Asn Gly
        115                 120                 125

Ala Ser Pro Glu Gly Lys Asp Ala Lys Ile Lys Phe Ser Val Glu Leu
    130                 135                 140

Pro Ile Thr Leu Asn Pro Arg Asp Pro Val Gly Leu Ile Leu Leu Gln
145                 150                 155                 160

Asn Pro Glu Thr Ser Val Thr Leu Thr Val Asp Val Glu Thr Leu Ala
                165                 170                 175

Lys Ala Tyr Ser Leu Asn Ala Ser Asn Ala Asp Gln Val Leu Phe Lys
            180                 185                 190

Ser Met Lys Val Thr Pro Met Leu Glu Ala Phe Asn Ile Pro Pro Val
        195                 200                 205

Pro Gln Ala Phe Pro Asp Ile Ser Thr Leu Lys Leu Val Ser Ser Lys
    210                 215                 220

Ser Asp Thr Phe Ser Gly Asn Gly Gln Asn Ile Leu Lys Leu Asn Thr
225                 230                 235                 240

Gly Thr Ile Tyr Arg Lys Leu Ile Leu Phe Ile Glu Asp Lys Asn Gly
                245                 250                 255

Asn Pro Leu Ala Asp Glu Asp Phe Gln Gly Asn Leu Glu Leu Val Phe
            260                 265                 270

Asn Gln Ala Asp Ile Pro Tyr Ser Ile Lys Pro Glu Ile Leu Ala His
        275                 280                 285

```
Ile Asn His Ser Gln Leu Gly Tyr Ala Leu Pro Lys Gly Met Tyr Ala
    290                 295                 300

Phe Asp Phe Thr Asn Gln Gly Ile Pro Asn Leu Gly Gly Ser Arg Asp
305                 310                 315                 320

Phe Ile Asp Thr Glu Arg Leu Thr Glu Phe Trp Leu Arg Phe Ser Thr
                325                 330                 335

Gln Lys Glu Gly Lys Val Thr Val Val Ser Glu Asn Leu Ser Arg Leu
                340                 345                 350

Arg

<210> SEQ ID NO 13
<211> LENGTH: 74
<212> TYPE: PRT
<213> ORGANISM: Bacillus phage Wip1

<400> SEQUENCE: 13

Met Ala Gly Glu Leu Ser His Phe Lys Lys Asp Leu Tyr Pro Asn Leu
1               5                   10                  15

Gly Phe Glu Asn Thr Ser Tyr Leu Ser Ile Pro Glu Ala Glu Asp Gln
                20                  25                  30

Gln Ala Met Val Asp Asp Gln Lys Val Ala Glu Glu Thr Ala Arg Thr
            35                  40                  45

Ser Asn Lys Ala Gly His Lys Asn Ile Met Leu Gly Ile Val Leu Leu
    50                  55                  60

Ile Ile Ile Met Phe Val Leu Gly Lys Val
65                  70

<210> SEQ ID NO 14
<211> LENGTH: 59
<212> TYPE: PRT
<213> ORGANISM: Bacillus phage Wip1

<400> SEQUENCE: 14

Met Asp Val Ala Gln Met Thr Gln Leu Ile Gly Asn Met Gly Phe Pro
1               5                   10                  15

Ile Phe Thr Ala Ile Tyr Phe Met Thr Tyr Met Lys Lys Thr Leu Asp
                20                  25                  30

Thr Cys Thr Gln Ser Met Val Ala Asn Thr Gln Ile Met Ile Arg Ile
            35                  40                  45

Glu Lys Phe Leu Asp Asp Lys Glu Lys Lys Ser
    50                  55

<210> SEQ ID NO 15
<211> LENGTH: 157
<212> TYPE: PRT
<213> ORGANISM: Bacillus phage Wip1

<400> SEQUENCE: 15

Met Asp Arg Gly Leu Thr Phe Phe Thr Leu Ala Leu Leu Leu Ile Trp
1               5                   10                  15

Leu Val Phe Asp Asp Leu Phe Gly Glu Lys Lys Tyr Leu Ser Lys Leu
                20                  25                  30

Ala Gly Ala Met Thr Pro Asn Leu Ser Leu Pro Asp Pro Ala Arg Asp
            35                  40                  45

Ala Val Asp Lys Val Val Glu Asp Thr Lys Glu Asn Ala Lys Lys Asp
    50                  55                  60

Val Thr Asp Ile Lys Lys Asp Thr Lys Asp Ala Val Lys Asp Thr Lys
65                  70                  75                  80
```

```
Lys Ser Phe Asp Asp Phe Ile Asn Gly Gly Phe Glu Lys Glu Met Lys
                85                  90                  95

Lys Asp Val Asn Asp Phe Lys Asp Trp Thr Lys Asp Leu Pro Asn Pro
            100                 105                 110

Asp Lys Met Lys Glu Lys Ala Asn Asn Asp Phe Lys Ala Ile Trp Asp
        115                 120                 125

Glu Val Ser Lys Ala Leu Glu Asp Thr Lys Lys Ser Ala Asn Asp Met
130                 135                 140

Trp Asp Asp Val Thr Ser Ser Val Lys Gly Trp Phe Lys
145                 150                 155

<210> SEQ ID NO 16
<211> LENGTH: 61
<212> TYPE: PRT
<213> ORGANISM: Bacillus phage Wip1

<400> SEQUENCE: 16

Met Val Gln Met Lys Asn Phe Thr Glu Ser Leu Gly Phe Ile Val Ala
1               5                   10                  15

Phe Met Val Met Thr Ile Phe Ile Ser Met Phe Thr Asn Glu Ser Val
                20                  25                  30

Thr Asn Gly Phe Leu Leu Val Leu Ala Ser Met Met Val Val Asn
            35                  40                  45

Ala Asp Lys Phe Thr Lys Phe Leu Asp Gly Val Met Lys
        50                  55                  60

<210> SEQ ID NO 17
<211> LENGTH: 48
<212> TYPE: PRT
<213> ORGANISM: Bacillus phage Wip1

<400> SEQUENCE: 17

Met Gly Arg Ile Leu Gly Ile Ile Ser Gly Ile Gly Leu Leu Ile Ala
1               5                   10                  15

Leu Tyr Leu Phe Leu Ser Asn Ala Arg Gln Thr Thr Gln Ile Ile Asp
                20                  25                  30

Ser Met Ala Gly Asn Ala Val Ser Gly Ile Lys Val Leu Gln Gly Arg
            35                  40                  45

<210> SEQ ID NO 18
<211> LENGTH: 91
<212> TYPE: PRT
<213> ORGANISM: Bacillus phage Wip1

<400> SEQUENCE: 18

Met Leu Asp Gly Thr Tyr Arg Tyr Gln Val Gln Asn Arg Gln Ala Leu
1               5                   10                  15

Gln Ala Leu Asp Lys Arg Val Glu Ile Pro Asp Ala Arg Leu Gly Val
                20                  25                  30

Gly Ala Ala Glu His Leu Glu Ala Met Gly Ile Arg Val Tyr Glu
            35                  40                  45

Asn Lys Val Pro Lys Leu Val Leu Pro Ser Val His Arg Leu Pro Phe
        50                  55                  60

Glu Gln Val Gln Pro Lys Asn Val Glu Pro Asp Met Phe Val Thr Asp
65                  70                  75                  80

Asp Phe His Val Gly Asp Ala Ile Met Gly Val
                85                  90
```

<210> SEQ ID NO 19
<211> LENGTH: 213
<212> TYPE: PRT
<213> ORGANISM: Bacillus phage Wip1

<400> SEQUENCE: 19

```
Met Ala Asp Ile Val Pro Val Gly Gly Gly Gly Gly Gly Gly His
1               5                  10                  15

Gly Ser Ser Pro Ser Lys Lys Thr Asn Asn Lys Met Leu Phe Met Val
            20                  25                  30

Gly Gly Val Val Val Val Leu Leu Val Phe Leu Gln Arg Ser Lys
        35                  40                  45

Ser Ser Gly Gly Asn Val Asp Thr Leu Gln Asn Thr Ile Pro Ile Ser
    50                  55                  60

Asp Ser Gln Arg Leu Asp Asn Phe Gln Ser Ile Val Ser Gly Glu Thr
65                  70                  75                  80

Ser Ala Gln Ile Asn Gly Met Met Lys Asp Ala Gln Asp Gly Trp Ser
                85                  90                  95

Gly Met Phe Lys Asp Phe Ser Glu Lys Met Thr Asn Gln Met Lys Glu
            100                 105                 110

Met Asp Asp Arg Asn Lys Glu Tyr Asn Lys Gln Gln Asp Trp Val
            115                 120                 125

Lys Asp Ser Phe Thr Asn Ile Lys Asp Ser Leu Gly Val Gly Ala Ile
130                 135                 140

Arg Asn Asp Asp Asn Ala Thr Phe Thr Ile Gly Asn Gly Thr Thr Gly
145                 150                 155                 160

Ala Ala Lys Thr Tyr Asp Gln Gln Leu Asn Asp Phe Arg Asn Asp Arg
                165                 170                 175

Gln Lys Leu Ala Glu Glu Ile Lys Arg Thr Gln Ser Val Ile Thr Phe
            180                 185                 190

Arg Lys Asn Asn Gly Leu Asp Val Ser Asn Gln Val Gln His Tyr Lys
            195                 200                 205

Asn Leu Gly Ala Leu
    210
```

<210> SEQ ID NO 20
<211> LENGTH: 218
<212> TYPE: PRT
<213> ORGANISM: Bacillus phage Wip1

<400> SEQUENCE: 20

```
Met Ala Ala Asp Ile Thr Pro Phe Ile Ala Asp Ala Gln Arg Ile Gln
1               5                   10                  15

Lys Gln Thr Gly Ile Pro Ala Ser Ile Ile Leu Gly Gln Ile Ile Phe
            20                  25                  30

Glu Ser Ser Gly Lys Phe Pro Gly Gly Leu Ser Gly Leu Ala Tyr Asn
        35                  40                  45

Asn Lys Asn Leu Phe Gly Ile Lys Gly Lys Gly Thr Ala Gly Thr Ala
    50                  55                  60

Asn Met Trp Ser Lys Glu Tyr Asp Ala Gly Gly Asn Arg Val Ser Gly
65                  70                  75                  80

Phe Arg Ser Tyr Asn Ser Trp Thr Glu Ser Leu Asn Asp His Ala Arg
                85                  90                  95

Leu Leu Gln Thr Asp Arg Tyr Ala Lys Tyr Leu Lys Asn Ala Thr Ser
            100                 105                 110
```

Val Glu Asp Tyr Ala Asn Gly Ile Ile Lys Gly Tyr Ala Thr Asp
            115                 120                 125

Pro Ala Tyr Ala Lys Gln Leu Leu Gly Ile Ile Lys Ser Asn Gly Leu
            130                 135                 140

Thr Lys Tyr Asp Asp Gly Lys Tyr Thr Phe Thr Gly Gly Asp Val Ser
145                 150                 155                 160

Gly Gly Ser Ala Gly Gly Gly Ser Gly Gly Ser Phe Phe Ala Pro
                165                 170                 175

Leu Phe Asn Ala Ile Ile Arg Ala Leu Leu Phe Val Leu Cys Val Val
            180                 185                 190

Ala Ala Leu Leu Leu Phe Ala Asn Ala Phe Pro Ser Val Glu Gln Thr
            195                 200                 205

Val Lys Ser Val Ala Lys Lys Val Lys Ser
            210                 215

<210> SEQ ID NO 21
<211> LENGTH: 175
<212> TYPE: PRT
<213> ORGANISM: Bacillus phage Wip1

<400> SEQUENCE: 21

Met Ser Gly Thr Asn Gly Leu Lys Leu Asn Ser Lys Leu Gln Glu Ala
1               5                   10                  15

Tyr Asn Lys Ala Ile Ala Ser Gly Leu Arg Phe Thr Ser Gly Phe Arg
            20                  25                  30

Ser Gly Ser Thr Gly Pro Ser Gly Arg Pro Asp Ser His Ser Gln Gly
        35                  40                  45

Met Ala Met Asp Phe Ala Gly Ser Lys Ala Gln Met Lys Gln Phe Ser
    50                  55                  60

Glu Trp Ala Lys Met Thr Gly Leu Phe Thr Glu Val Leu Tyr Glu Thr
65                  70                  75                  80

Ala Gly His Tyr Asp His Val His Val Gly Trp Gln Thr Gly Lys His
                85                  90                  95

Pro Asp Gly Lys Thr Tyr Val Gly Asp His Lys Leu Ile Asp Arg Val
            100                 105                 110

Gly Ser Gly Thr Leu Gly Asp Leu Gln Thr Val Gly Asp Thr Val Ala
            115                 120                 125

Pro Ala Gly Gly Gly Asp Lys Ala Gly Phe Met Ser Ser Leu Phe Thr
            130                 135                 140

Gly Ile Phe Arg Val Val Met Ile Val Ile Cys Leu Ile Gly Gly Val
145                 150                 155                 160

Tyr Phe Ile Met Asn Ala Phe Pro Gln Met Lys Gln Leu Ile Lys
                165                 170                 175

<210> SEQ ID NO 22
<211> LENGTH: 291
<212> TYPE: PRT
<213> ORGANISM: Bacillus phage Wip1

<400> SEQUENCE: 22

Met Asp Arg Lys Thr Asn Ser Thr Trp Arg Glu Gln Thr Pro Thr Ile
1               5                   10                  15

Pro Ser Lys Thr Val Phe Asp Val Val Phe Pro Asp Thr Lys Pro Asn
            20                  25                  30

His Tyr His Ile Asn Asn Leu Ser Ala Ala Pro Ile Tyr Leu Gly Thr
        35                  40                  45

```
Thr Thr Leu Ala Ser Pro Lys Thr Tyr Asp Ile Val Val Asn Gly Asn
 50                  55                  60

Gly Asp Asn Met His Ala Arg Asp Leu Gly Val Thr Arg Ile Thr Leu
 65                  70                  75                  80

Tyr Asn Asp Ser Pro Asp Lys Ala Arg Ile Val Leu Thr Thr Phe Glu
                 85                  90                  95

Asp Lys Phe Asn Pro Ala Val Leu Ala Gly Arg Gly Gly Ser Val Thr
            100                 105                 110

Val Thr Gly Gly Gly Gly Ala Gly Val Ile Thr Gly Phe Asn
        115                 120                 125

Ala Ser Leu Pro Ser Gly Asp Asn Asn Ile Gly Arg Val Lys Val Thr
130                 135                 140

Glu Met Pro Ala Ile Asp Phe Val Leu Gly Thr Leu Pro Ala Gly Thr
145                 150                 155                 160

Asn Asn Ile Gly Lys Val Glu Val Ser Lys Leu Pro Leu Ala Ser
                165                 170                 175

Val Gly Gly Lys Ile Gly Asp Val Gly Ile Gln Gly Val Thr Ile
                180                 185                 190

Thr Ser Met Pro Ala Val Glu Leu Glu Val Ser Lys Asp Leu Asn Val
        195                 200                 205

Lys Glu Lys Ser Tyr Asn Asp Phe Phe Tyr Gln Glu Pro Asn Val Glu
210                 215                 220

Gln Thr Glu Val Val Phe Thr Thr Asp Leu Ser Arg Ile Ile Phe Ile
225                 230                 235                 240

Ser Asn Asp Gly Gln Asn Pro Leu Lys Val Thr Leu Asn Asn Arg Thr
                245                 250                 255

Ile Thr Leu Leu Gln Asn Glu Val Ile Glu Leu Pro Leu Leu Thr
            260                 265                 270

Lys Thr Ile Lys Leu Val Arg Pro Ser Gly Ser Gly Ser Ala Arg Ile
        275                 280                 285

Met Gly Val
    290

<210> SEQ ID NO 23
<211> LENGTH: 117
<212> TYPE: PRT
<213> ORGANISM: Bacillus phage Wip1

<400> SEQUENCE: 23

Met Gly Leu Lys Lys Pro Ala Val Gly Gly Lys Arg Val Ala Lys Gly
 1               5                  10                  15

Ile Gly Lys Pro Phe Gln Pro Gln Gly Ser Ala Ser Trp Val Val Glu
             20                  25                  30

Val Arg Gly Leu Ser Phe Lys Pro Ser Val Val Ala Thr Lys Pro Lys
         35                  40                  45

Lys Ser Gln Ile Asp Ala Asp Tyr Pro Tyr Arg Val Gly Thr Val Gly
     50                  55                  60

Ile Ala Arg Thr Ala Phe Glu Pro Pro Leu Asp Glu Asp Leu Leu Asn
 65                  70                  75                  80

Met Ile Asn Asn Asp Gly Asp Tyr Ser Val Gly Arg Val Thr Phe
                 85                  90                  95

Tyr Asp Asp Gly Phe Lys Ile Tyr Leu Asp Lys Gly Asn Glu Gln Pro
            100                 105                 110

Trp Val Ala Tyr Glu
        115
```

<210> SEQ ID NO 24
<211> LENGTH: 118
<212> TYPE: PRT
<213> ORGANISM: Bacillus phage Wip1

<400> SEQUENCE: 24

Met Tyr Val Asn Lys Arg Val Tyr Phe Glu Lys Asp Thr Gly Ile Val
1               5                   10                  15

Val Met Val Thr Gly Gly Phe Arg Asp Asp Trp Leu His Ser His Pro
            20                  25                  30

Thr Val Gln Glu Asp Met Ala Lys Tyr Ser Val Leu Ala Glu Arg Val
        35                  40                  45

Pro Asp Thr Leu Ser Met Leu Glu Leu Lys Glu Gly Thr Tyr Asp Glu
    50                  55                  60

Glu Phe Ser Lys Ala Arg Ser Phe Lys Val Asp Val Lys Thr Asn Thr
65                  70                  75                  80

Ile Val Phe Asp Phe Thr Pro Glu Asp Lys Lys Glu Val Glu Glu Lys
                85                  90                  95

Lys Thr Pro Glu His Arg Val Thr Met Val Glu Ser Ala Ile Asn Asp
            100                 105                 110

Ile Leu Leu Gly Gly Met
        115

<210> SEQ ID NO 25
<211> LENGTH: 48
<212> TYPE: PRT
<213> ORGANISM: Bacillus phage Wip1

<400> SEQUENCE: 25

Met Thr Leu Ser Gly Leu Ala Ala Tyr Ile Leu Asn Gln Trp Leu Leu
1               5                   10                  15

Gly Lys Phe Thr Asn Ser Asp Leu Asn Thr Leu Val Asp Arg Gly Arg
            20                  25                  30

Ile Thr Glu Glu His Arg Val Tyr Phe Leu Ser Met Lys Glu Glu Lys
        35                  40                  45

<210> SEQ ID NO 26
<211> LENGTH: 213
<212> TYPE: PRT
<213> ORGANISM: Bacillus phage Wip1

<400> SEQUENCE: 26

Met Tyr Tyr His Asn Arg Asn Leu Ala Asn Leu Glu Lys Leu Ala Pro
1               5                   10                  15

His Thr Arg Gln Lys Ala Lys Gln Trp Tyr Gln Tyr Cys Val Glu Asn
            20                  25                  30

Gly Ile Glu Val Leu Ile Tyr Glu Thr Thr Arg Thr Ile Glu Gln Gln
        35                  40                  45

Arg Glu Asn Val Arg Lys Gly Ala Ser Gln Thr Met Lys Ser Tyr His
    50                  55                  60

Leu Val Gly Gln Ala Leu Asp Phe Val Pro Ala Arg Glu Ala Glu Val
65                  70                  75                  80

Tyr Trp Asp Gly Tyr Tyr Arg Asn Asp Ile Gln Lys Ala Ile Gly Tyr
                85                  90                  95

Ala Lys Ser Ile Gly Phe Glu Trp Gly Gly Asp Trp Lys Gly Phe Val
            100                 105                 110

```
Asp Ser Pro Pro Leu His Tyr Asn Tyr Asn Gly Tyr Gly Thr Asp Lys
            115                 120                 125

Gly Asn Val Ser Asp Glu Pro Val His Val Thr Gly Asn Thr Gly Val
        130                 135                 140

Val Arg Val Val Val Asp Ser Ala Leu Val Arg Arg Glu Pro Thr Thr
145                 150                 155                 160

Gln Ser Pro Ile Asn Thr Asp Ala Gly Glu Asn Gly Arg Leu Tyr Arg
                165                 170                 175

Gly Thr Glu Trp Gln Ala Trp Gly Ser Thr Ile Gly Glu Gly Gly Tyr
            180                 185                 190

Thr Trp Tyr Pro Leu Gly Asn Glu Met Trp Val Arg Gly Asp Leu Val
        195                 200                 205

Ser Trp Arg Asn Ala
    210

<210> SEQ ID NO 27
<211> LENGTH: 898
<212> TYPE: PRT
<213> ORGANISM: Bacillus phage Wip1

<400> SEQUENCE: 27

Met Lys Lys Ile Asn Pro Ser Phe Leu Gly Val Glu Gly Leu Asp Lys
1               5                   10                  15

Leu Glu Tyr Ser Glu Met Glu Val His Leu Ser Asn Val His Thr Phe
            20                  25                  30

Ser Ser Pro Lys Pro Thr Glu Tyr Leu Tyr Ser Asp Lys Pro Lys Gly
        35                  40                  45

Leu Tyr Gly Phe Lys Phe Glu Ile Asp Glu Val Thr Gly Glu Ile Met
    50                  55                  60

Leu Phe Gly Phe Cys Ser Tyr Asn Pro Val Thr Lys Lys Asn Gly Tyr
65                  70                  75                  80

His Tyr Ile Tyr Arg Glu Asn Glu Lys Asp Met Asp Leu Ser Val Ile
                85                  90                  95

Tyr Met Leu Lys Asn Ile Ile Lys Asp Cys His Phe Asn Asn Lys Ile
            100                 105                 110

Ile Cys His Phe Asn Glu Ile Glu Ser Ile Leu Ile Leu Lys Leu Leu
        115                 120                 125

Met Lys Arg Lys Tyr Leu Glu Gln Asp Glu Gln Val Lys Ile Phe Gln
    130                 135                 140

Arg Val Leu Lys Gly Ile Asn Gly Lys Phe His Lys Ser Gly Ser
145                 150                 155                 160

Trp Thr Glu Pro Pro Ile Ile Glu Leu Asp Ile Gly Asn Gly Glu Ser
                165                 170                 175

Ile Gly Val Ser Lys Val Leu Asn Gly Asn Leu Glu Leu Phe Val Ile
            180                 185                 190

Lys Asn Lys Lys Met Ser Lys Cys Asn Thr Phe Arg Ser Lys Pro Phe
        195                 200                 205

Trp Gln Lys Thr Pro Ile Glu Cys Ala Arg Asn Ala Asn Leu Lys Tyr
    210                 215                 220

Ala Glu Glu Ile Lys Glu Ser Lys Ile Asn Trp Asp Leu Phe Leu Asn
225                 230                 235                 240

Gly Tyr Asn Lys Lys Val Asp Lys Asn His Lys Leu Gln Asp Asn
                245                 250                 255

Thr Tyr Val Lys Lys Ile Leu Arg Glu Asn Met Tyr Asn Ser Phe Leu
            260                 265                 270
```

-continued

```
Ser Lys Asp Leu Ile Tyr Val Met Asn Met Phe Lys Glu Ser Phe
    275                 280                 285
Gly Cys Phe Pro Asn Ser Phe Tyr Ser Ala Gly Thr Leu Ser Glu Ala
290                 295                 300
Ala Ile Ala Lys Val Leu Asp Glu Asn Glu Leu Lys Thr Phe Ser Ile
305                 310                 315                 320
Asp Ser Thr Met Asn Asp Trp Gln Glu Lys Asp Ile Asp Val Asp Ile
            325                 330                 335
Ile Ala Lys Ala Ile Asn Leu Ser Phe Asp Ala Asn Gln Gly Ala Ile
            340                 345                 350
Ile Glu His Glu Lys Val Gly Tyr Ile Ala Arg Gly Ala Asn Thr Asp
        355                 360                 365
Ile Gly Ala Ser Tyr Pro Ala Ile Met Arg Tyr Cys Ile Pro Asp Leu
    370                 375                 380
Arg Asn Ser Arg Val Gln Tyr Phe Asp Asn Ile Lys Asp Phe Thr Glu
385                 390                 395                 400
Ile Pro Lys Pro Ser Leu Lys Arg Ile Val Met Leu Thr Cys Glu Phe
            405                 410                 415
Glu Ile Pro Pro Asp Val Arg His Thr Ile Met Ile Lys Gln Lys Gly
            420                 425                 430
Glu Glu Gly Thr Val Asn Gln Ile Arg Arg Asn Val Leu Gly Phe Gly
        435                 440                 445
Asn Phe Val Thr Thr Val His Tyr Lys Glu Val Glu Phe Leu Leu Ser
    450                 455                 460
Gln Ile Asp Lys Asp Lys His Asn Glu Val Ile Lys Glu Ile Ile Glu
465                 470                 475                 480
Val Val Val Ile Glu Thr Asp Gly Lys Leu His Pro Ile Ser Lys Val
            485                 490                 495
Ile Asp Ile Leu Trp Glu Leu Arg Leu Lys Leu Arg Asp Ile Gly Asn
            500                 505                 510
His Ser Glu Tyr Ile Val Lys Leu Ile Thr Asn Ala Ile Tyr Gly Lys
        515                 520                 525
Phe Phe Gln Ala Phe Gln Gln Tyr Ala Cys Ser Glu Asn Glu Asp Gly
    530                 535                 540
Glu Gln Glu Ile Tyr Phe Ala Gly Phe Asp Val Gly Tyr Met Phe Asn
545                 550                 555                 560
Pro Ile Val Ser Ser Met Ile Thr Ala Phe Gly Arg Ile Arg Val Gln
            565                 570                 575
Glu Gly Ala Leu Asn Ile Glu Arg Asn Gly Gly Lys Val Ile Ser Ile
            580                 585                 590
Leu Thr Asp Cys Val Lys Phe Glu Met Pro Asn Thr Glu Arg Pro Ala
        595                 600                 605
Tyr Asp Tyr Leu Asp His Cys Phe Asp Ser Val Leu Ser Glu Phe Glu
    610                 615                 620
Met Ile Asn Thr Asn Gly Trp Ser Pro Lys Gly Tyr Lys Val Leu Gly
625                 630                 635                 640
Ile Phe Glu Glu Pro Glu Glu Phe Thr Glu Gly Leu Phe Leu Asn Thr
            645                 650                 655
Ala Val Tyr Glu Tyr Lys Leu Ser Asn Asp Arg Trp Glu Val Lys Thr
            660                 665                 670
Ser Gly Tyr Gln Thr Phe Asp Lys Glu Phe Glu Asn Glu Ala Tyr Leu
        675                 680                 685
```

```
Met Lys Lys Leu Asp Asn Phe Leu Lys Lys Pro Glu Ser His Phe
    690                 695                 700
Lys Tyr Gly Lys Arg Ala Gly Glu Tyr Gly Leu Lys Leu Gly Lys Glu
705                 710                 715                 720
Glu Ile Ile Asn Tyr Phe His Val Val Glu Asp Leu Ala Asp Phe Arg
                725                 730                 735
Gln Leu Gly Ile Lys Lys His Lys Glu Leu Pro Leu Ile Phe Asp Ser
            740                 745                 750
Phe Ser Leu Lys Pro Lys Arg Ala Tyr Tyr Thr His Leu Asn Glu Asp
        755                 760                 765
Ile Glu Leu Ser Leu Asn Asn Ile Lys Asp Arg Leu Phe Glu Thr Ser
770                 775                 780
Pro Ile Asp Ile Thr Met Glu Tyr Gly Cys Tyr Asn Asp Asp Phe Glu
785                 790                 795                 800
Trp Gln Cys Phe Asp Asn Arg Lys Lys Thr Ala Arg Glu Leu Leu Thr
                805                 810                 815
Ile Pro Lys Ile Ser Asp Ile Lys Lys Glu Lys Lys Glu Lys Arg Arg
            820                 825                 830
Lys Thr Gln Asn Asp Phe Ile Lys Asn Lys Arg Glu Ile Leu Ser Val
        835                 840                 845
Leu Gln Lys Gln Ile Lys Glu Asn Ile Asn Leu Phe Pro Phe Asp Lys
850                 855                 860
Phe Thr Met Lys Glu Gly Ser Asn Gly Gly His Asn Ala Arg Asp Tyr
865                 870                 875                 880
Gly Ile Glu Lys Met Arg Asp Leu Leu Asn Glu Arg Gly Ile Lys Pro
                885                 890                 895
Ala Ala

<210> SEQ ID NO 28
<211> LENGTH: 14319
<212> TYPE: DNA
<213> ORGANISM: Bacillus phage Wip1

<400> SEQUENCE: 28
cgaatctcac tttgttcgat taaccccaat tcttttatg  agtcgggaaa tattttgta      60 gcataacttc attgtgactt gtcacacttt tcctcaaatg ttaaaaatga catattgtgt    120
tgttttttaa ttgaaaatga tttaaaatta atttatgtaa ttcatcacaa tatggaagga    180
agttttaagt ttgaaaaaac tcacaactat aacagttgat actcgagcca aaaaaaaaga    240
tttgatagag tgtcacatag gttgggaaca aaaaacgcaa ctgaaacact acaaaaacta    300
attgattact ttgaaaaagc tgatgataag ctattcattg agttgcatga tttctttat    360 gaaacgatga aaagcaaata cgaggatagt taggtatggc taaatccac cttaccctc    420 aatacgttag gaaaattatt tgtacagatt gtggatgtat aatagaaaaa aacattaatt    480
ataaaccgcc taaaataat tattttcaga agtgcaatga aygccaaagt ccaaacacta    540 tgtttctta caaagagaaa agagataaa aagaaacata atatggagtg atttaatttg    600
aagaagaaga agacacttta taaagagata agagaattag gttttgatgt taattttca    660 aggaaagtct cacgaagaaa agatggtgca tttgataaag ttcgtttgga agagcttta    720 tttaaatata aaggtgatgc atcttgggta gaaaaagat tcmatggtaa tcaaagtctt    780
actaaaaaag agatcagtaa attattaac gccgaargaa gagaaaggaa atttttaaa    840 ggaagatacg ctggtgagtt ctccacgaaa gaaagaagca tttagaaaaa aacattaagt    900
```

```
tcaagcggat taaaagaagt taatcgttta ttgaaaaaca atactataga tatattaagt        960
agaacagaag agttcaaaca atttattggt agaggtaaaa aaccaccaaa gcatatgatt       1020
aaagatatta aacgaataaa taaattcatg ggagcaagtc cgaacggaca gccaggttta       1080
tttgttgtaa gggaaatgta catcaatggt ttgactgaat tagaagctat tgaacttata       1140
aaggacaggc aaagtccagt tgataaagat acggtttttt atagttgatt aaaaatcaca       1200
gtgaaggtgg aataaaatat gatgaatgat acagagaaaa ctattttttaa tgctattgaa      1260 aattttcaaa ctgaacatgg ttatagtcct tccttaacag aactagaaga gaaacatttt       1320
tattcacgta gcactgtgag gcattgcata aaaactttag aagaaaaagg atatttagaa       1380
ttggatagac aagtaagaag gaatatccgt ttgcgtaata tgtcagctat tataaaagat       1440
gttaaagaaa atattaatga tgatagtaag gttataagtg tagatgtaat tatagatatt       1500
ttaaatattt tacataacga attatctaat gacaatagaa caaaagaat aatttaattc        1560 taaagactaa ctttcaggtt agtctttttt atttacctaa aaatgtcaca ttgtgtcaca       1620
gtacactata tattgtgttt tattttttag ttatatacta aatgtagaaa aacaaaaggg       1680
gtgtaacaaa tgaaaatcca tgataagaaa tttgaaattg ataaagaatt atcggatgca       1740
atttgttggg agttgtcgga atatcaaaca ataataactt tagcttttgac taattgtagc      1800 aaagatgaag ttttgaaaat atcacaattg gttgatagaa atgaacgttt ttctgaaaca       1860 actaagaat ggttgaaaga aactataaat aaattccata aacctatatg ggagatggaa        1920
ttaaaaaata ataaaacaga attaaaaata gcacaaaatg tttaaatcag tatcaaaaat       1980
atatcgtgat tcactaaagc aaaacattaa acttaatgac gaaaatgcag aattaagaga       2040
acaaaacatt ttgttgaaaa gaaagttagc gaaaagtgaa tcacttttat atcaactaca       2100
aaatgatagg agtgtcacga atggactcat taaaagtagt agaagaaaaa ccgaaattta       2160
gattaggaga tttccaattc tttgcaaaga agaaagaaga gggagaagag gaagacctag       2220
aagacgttga ggaagagtat gaagaaggtg aagacgtacc gaaacctaaa cgtaaaccaa       2280
aatcaaaaag cgaggaggaa gcaccagcat gggcgcaaaa gataatcgac ttagtaaccc       2340
cgaaagcgga ggaacagaac caaaaacaga aagtaccagt acccgaagca ccagtagtgg       2400
aggaagagga agaagaggag cagccgcaac aggagggagc agtgaaaaga ttcctaaggc       2460
aactttggta gaagtgccgg gtcaagaaaa atctcccgag gatgcaaaaa aggaagaaca       2520
acgtaaggca gcagccgcac gaaaacgaaa atcacgtgca gcagccaata cgaaaaagaa       2580
agcaagtgca tccgttggcg atgcaacgca attaaragyg ttggtgctta caacttcaaa       2640
tatcatcgct gcaagagaag gtatggcgat gtgggcaatg agtsagcaag aagtggacca       2700
aattataaca cctctcttaca gcatcctgtc acgtaatgac gggttgggag aagtcatggg      2760
tgaatatgcc gaccacattg ctttaatcgt ggcagcattt actatatttg taccaaaatt       2820
catgatgtgg aaagcatcaa gaccgaagaa ggagggaacg cattatgcta gaccaaatca      2880
aagtaccaaa cgagaacaag ggaagcaaac aggagaggtt gcagctggta gtggaccaag       2940
tggtggacag tctaccaaca acggtacgac ttttggcagg gagctatctc aactcattcc       3000
gccaagtgct ggaatctgag cagcaggaca ttgacgaaaa cattgataac gctttgtcac       3060
gcctacgtga gtacatcgac tatattcaat atggtcacga tcaagaaaat gagtaggtga       3120
tttcatggaa cgtatcccta cagaccaaca tgtatttatc acaggacaaa cggggacagg       3180
aaaatctttt cttgctgaaa cgtatttagc gggctatgaa catgtagtca agctggacac       3240
aaaaggtgaa gtgtttgaaa gacgaaaaaa gaaacaacct gtatggcgtg ggttacggga       3300
```

```
aggaaaggac tttacggtca tagagcgttt agcggacatt gatgatgtag aaacaaagaa    3360
aatcatttat gctcctgttt tccaagaaca agaaatggaa tactatgacg cgttgatgca    3420
atgggtgtac aggagagaaa acacacaatt atgggttgat gaactcatgg aggtatgccc    3480
gagtcctttc aaataccctc cttacttaaa aggtttaatg actaggggc gttcaaaaga    3540 agctactgta tgggcttgta cgcaacgccc aagtgacatt ccttctattg taatggggaa    3600
cagtgaccac ttttcgtct ttgaccaaaa cttgcctagt gaccgtaaga agttatgtga    3660
aacaacgggt agttctgaat ttatggaatt accgggctat cgtaacttct ggtatttcaa    3720
gcgtggatgg agtgaccccg tacttgcgac attgaaagtg tgaccttgaa aggggtgct    3780 atagtggagg ggaaatttgc agggattgga ctcaaaaata tactcgctat cttttctta    3840 ttcattgttt tcattgtgat ggctaaagtt gttttgacga atatcccat caaaggaatt    3900 tcagaagtaa ttcaaacagt ataggaggga ataggctatg aatctattta gccctaaatg    3960
gtggatttca agtttaattg ccgctttcat ggcaatgttc atgatttayc tagtaaaaca    4020
aattgcatca aaagcaaaca ttccgtttgt atcaaaagta actgaggagg cttacaagta    4080
atggcagaac aacaaatttc agcacaagca cgtgcggcga actttgcaac cgcaacacga    4140
caaaactatc aaatgttacc atcacaacaa gtcagggaag aaagcagcac aatcgaattt    4200
acattaccaa aagcacgtct attatcaaag attattttaa atgtggaagc cgtagcgact    4260
ctaaagagta aagggactgc catccaaacg cacgacttca caccttatcc tattttacga    4320
cgtgtatcac tagacctcaa taacggattt agtccattta ttgtgagtgg tcgtgaccct    4380
gtacaataca acatgctgcg tttaaatcca acgtattat tcccaagtac aaatccacgt    4440
gcgatgaact atgtggaaaa cggggctagt cctgagggta aagatgcaaa gattaagttt    4500
tcagtagagt tacctatcac attgaatcca cgtgaccctg taggtcttat cttgctgcaa    4560
aaccctgaga caagcgtgac attaacagtg gatgtcgaaa cattagcaaa agcgtatagc    4620
ttgaatgcat cgaatgccga ccaagtttta tttaaatcga tgaaagttac accgatgtta    4680
gaagcgttta acattccacc tgttccgcaa gcgttccctg atatttctac actgaaactc    4740
gtttctagta aatcagatac attctcgggt aatggtcaaa acatcttgaa attaaacaca    4800
ggtacaatct atcgtaagtt aattttattc attgaagata aaaacggaaa cccgcttgcg    4860
gatgaagatt tccaaggcaa cttagaactc gtgtttaacc aagcggacat cccgtatagc    4920
atcaagcccg aaatattggc tcatatcaat cacagtcaat tagggtacgc acttccaaaa    4980
ggtatgtacg cctttgactt tacaaatcaa gggattccga atttaggcgg tagccgtgac    5040
tttatcgata cggaacgttt aacagaattc tggctacgat tcagtacgca aaaagagggt    5100
aaagtgacgg ttgtttctga aacttgtca cgcttacgtt aaaagaaga ggggatttcc    5160 ccttttcttc tatataagga gggatagtgc atggcaggtg aattaagtca tttcaaaaaa    5220
gacctgtatc caaatttagg ttttgaaaat acatcttact tatcaattcc cgaagccgaa    5280
gaccaacaag caatggtaga tgaccaaaag gttgctgagg aaaccgcaag gacatcaaac    5340
aaagcgggtc acaaaaacat catgctcggg attgtcttgt taattattat catgttcgta    5400
ttaggaaagg tgtgataacg atggacgtag cacaaatgac acagttaata ggaaacatgg    5460
gtttccctat ttttactgct atttatttta tgacgtacat gaaaaagacg cttgatacat    5520
gtacacaatc aatggtagcg aatacacaaa tcatgattcg tattgaaaag ttttagatg    5580 ataaggagaa gaaatcatga gtaaaacatt aattctcgtg gttgcgattt tctgtttatg    5640
```

```
gtttttcgta atcaagaaaa agaaagcgtg atgtaaatgg atagagggtt aacctttttc   5700
acattagctt tgcttctcat atggttagtc tttgacgatc tattcggtga aaagaaatac   5760
ttgtctaaat tagcgggagc tatgacaccg aacttgtctc tacctgaccc cgcacgtgat   5820
gcggtagaca aggttgtaga agatacaaag gaaaacgcaa agaaagatgt gacagacatc   5880
aaaaaggata caaaggatgc cgtgaaagat acaagaaaat cgtttgatga tttcataaac   5940
ggtggttttg aaaaggaaat gaagaaggac gttaacgatt ttaaagattg acaaaagac    6000 cttcctaatc ctgacaagat gaaagagaaa gccaataacg attttaaagc aatatgggat   6060
gaagtctcca aagcgttaga ggatacaaaa aagtcagcta acgatatgtg ggatgatgtg   6120
acatcctcgg tgaaaggatg gttcaaatga aaaattttac ggagtccctc ggttttattg   6180
tagcgtttat ggttatgaca attttcatta gcatgtttac aaatgagtct gtgacaaacg   6240
gattcttgct gctcgtgctt gcgtcaatga tggtcgtaaa cgctgataag tttacaaaat   6300
ttttagatgg ggtgatgaaa taatgggacg tattttaggt attatttcgg gtattggttt   6360
gctaattgct ttgtacttat ttttaagtaa cgcacgacaa acaacgcaaa tcattgatag   6420
catggctgga aatgccgtga gtggtattaa agtattacaa ggtcgataag gagggtgtga   6480
catgttagat ggtacgtatc gctatcaagt acaaaataga caagccttgc aagcacttga   6540
taaacgtgtt gagattcccg atgcacgttt aggagtcggt gctgcggaac acttagaagc   6600
aatgggtatc cgtgttgtct atgaaaacaa agtaccaaaa ctggttttac catctgtaca   6660
tcgtttgcca ttcgagcaag ttcaacctaa aaatgtagag cctgacatgt tgtcacaga    6720 tgacttccat gtcggcgatg caattatggg ggtgtagcga atggctgata ttgtaccagt   6780
agttggcggg ggcggggggcg gcgggcatgg ctcgtcccct tctaaaaaga raaacaacaa   6840
aatgttattt atggttggtg gtgtggtcgt agttgtgctg ctcgtattct tgcaacgctc   6900
gaagtcatcg ggcggcaatg tggacacgct gcaaaacacg attccgattt cggattcgca   6960
aaggctcgac aattttcaat ccattgtgtc aggtgagaca tcggcacaaa tcaacgggat   7020
gatgaaagat gcacaggacg gttggtcggg aatgttcaag gatttcagtg aaaagatgac   7080
caatcaaatg aaagaaatgg atgaccgcaa caaggaatac aacaagcaac aacaggactg   7140
ggtgaaggat tcctttacaa atatcaagga ctcgctaggt gtgggagcga ttagaaatga   7200
cgataacgct accttcacaa tcggtaacgg acaacaggt gcggcgaaaa catatgacca    7260
acaactgaat gatttccgca atgatcgtca aaagttggct gaggaaatta acgtacaca    7320 atccgttatt acattccgta aaaacaacgg attagacgtt tctaatcaag tccaacacta   7380
taagaattta ggagcattgt aatggctgcg gatattaccc cttttcattgc ggatgcgcaa   7440 cgaattcaaa aacaaacagg aatcccagct tctattatat taggtcaaat cattttcgaa   7500
tcaagcggga gtttcctgg cggtttgtca ggactcgctt ataacaacaa aaacctttc    7560 gggattaaag gaaggggac ggctggaacg gctaatatgt ggtcaaaaga atatgatgcg   7620
ggagggaatc gggtttctgg tttccgctcg tacaattcat ggacagaatc gctcaatgac   7680
catgcacggt tgttgcaaac agaccgttac gcaaagtatt taagaatgc aacatctgtt    7740 gaagattatg caaatgggat tataaaaggc ggttatgcca ctgacccagc ttatgcaaaa   7800
caactgttag gcattattaa atcaaatggg cttacaaaat acgatgatgg gaaatacacc   7860
tttacaggcg gtgacgtgtc gggcggttct gctggtggtg ggggtagtgg cggttcattc   7920
tttgcaccgt tattcaatgc cattattcgg gctttgctat ttgttctatg tgtcgtggct   7980
gcgttgctgc tattcgcaaa tgcttttccccg agtgtggaac aaacagtgaa atcagttgcg   8040
```

```
aagaaggtga aatcatgagt ggtacaaacg gtttgaaact caatagcaaa ttgcaagaag    8100
cttacaacaa agctattgct agtgggttgc ggttcacatc gggattccgt tcggggtcaa    8160
ctggtccgag tgggagacct gatagccatt cccaaggcat ggctatggat tttgcgggaa    8220
gtaaagcaca aatgaaacaa ttttccgagt gggcgaaaat gacaggactc tttacagaag    8280
tgttgtatga cggcgggt cattacgatc atgtccatgt cggatggcaa actggaaaac      8340
accctgacgg aaaaacatat gtaggcgacc acaaactcat tgatagagta ggtagcggga    8400
cgctcggtga cttgcaaacg gttggtgaca cggttgctcc tgctggtggc ggagacaagg    8460
cggggtttat gtcttcccta tttactggca tatttcgagt tgtaatgatt gtcatatgtc    8520
tgattggcgg ggtctacttc attatgaatg cttttcccgca aatgaaacaa ttaatcaagt    8580
gaggtggaaa gaatggatag aaagacaaat agtacatggc gggagcaaac gcycaccata    8640
ccgtcgaaaa cagtatttga cgtggtattc cctgatacaa agccgaacca ttaccacatc    8700
aataacttat cggctgcacc tatttattta gggacaacta cactcgcatc accaaagacg    8760
tatgacattg ttgtaaacgg gaacggggac aacatgcacg ctcgtgacct cggtgtgact    8820
cgcataacgc tatataatga cagtcctgat aaggctcgaa ttgttttaac tacgttcgaa    8880
gacaagttta accctgcggt gcttgctggt cgtggtggta gcgttacggt gacaggtggt    8940
ggcggtggtg ctggtggcgt cattacaggt ttcaacgctt cccttcctag tggtgacaat    9000
aatattggtc gagtaaaagt gaccgaaatg cctgcaattg attttgtact cggtacatta    9060
cctgctggta caaacaatat agggaaagta gaagttagca aattaccacc gcttgctagt    9120
gttggcggga aaattggaga tgtcggaata cagggaggcg tgacgattac gtccatgccc    9180
gccgtagagt tagaggtaag taaggacttg aatgtaaaag agaagtcgta caacgatttc    9240
ttctatcaag aaccaaatgt agagcaaaca gaagttgtat tcacaacaga cctgtcacgt    9300 atcatttta tttcgaatga tggacagaac ccgttaaagg tcacgcttaa taaccgtacc      9360
attacattgc tgcaaaacga ggtaatagaa gaactaccac tactcacaaa aacaattaaa    9420
ctagtgcgac ctagtggaag tggaagcgca cggatcatgg gggtgtaggt tatgggactt    9480
aagaaacctg cggttggtgg gaagagggtt gctaaaggaa tagggaagcc ttttcaacct    9540
caagggtctg caagttgggt tgttgaagtg agaggacttt cttttaaacc tagtgtcgta    9600
gcaacaaaac ctaaaaaatc gcaaatagat gcggattatc catacagggt tggtacagtt    9660
ggtatagcaa gaaccgcatt tgaaccacct ttagatgaag acctttttaaa catgattaac    9720 aatgatggtg actattctgt aggtcgtgtt gttacgtttt atgatgatgg attcaaaata    9780
tatcttgaca aaggaaatga acaaccgtgg gttgcttatg aataggagag gtaaatcatg    9840
tatgtaaata aaagagttta tttcgaaaaa gatacaggta ttgtcgtaat ggttacgggt    9900
ggatttcgtg atgattggtt acattcccac ccgacagtgc aagaggacat ggcaaagtat    9960
tcagtgcttg ctgaacgtgt tccagatact ttaagcatgt tggaattaaa agaaggaacg   10020
tatgatgagg aattttcaaa ggctcgtagt ttcaaagtag atgtgaaaac aaatacgatt   10080
gtgtttgatt ttcacccga agataaaaag gaagtagaag agaaaaagac accggaacat    10140
cgtgtaacga tggttgaaag tgcaattaac gatatattac taggaggaat gtaaaatgac   10200
tttatcggga ttagctgctt atatttaaaa tcaatggtta ttaggtaaat ttacaaatag   10260
tgatttaaat acgctcgtgg atcgtggacg tattacagaa gaacaccgtg tctacttctt   10320
atcaatgaag gaggagaaat aatatgtatt atcacaatcg aaatctagca aacctagaga   10380
```

```
agttagcacc gcatacaaga cagaaagcaa aacagtggta tcaatattgt gtagaaaacg    10440
gtattgaggt actaatctat gaaacaactc gtaccatcga acaacaacgt gagaacgtac    10500
gtaaaggcgc gtcacaaact atgaagtcat accacttagt aggacaagct ttggatttcg    10560
taccagcaag agaagccgag gtatattggg atggatacta tagaaacgac attcaaaagg    10620
ctatcgggta tgcgaagtct atcggttttg aatgggtgg tgactggaaa gggtttgttg    10680
atagtccacr cttacartac aactataacg gttacgggac ggacaaagga aacgtgtcag    10740
atgagcctgt acacgtgaca gggaatacag gggttgtaag agttgttgtt gatagcgcac    10800
ttgtcagaag agagcctaca acacaatcac ctatcaatac ggatgctgga gaaaatggtc    10860
gcttatatcg tggtactgaa tggcaagcgt ggggaagtac aattggtgaa ggtggttata    10920
catggtatcc attaggaaat gaaatgtggg tacgtggtga tttagtaagt tggagaaatg    10980
cataaaatga aaaaagagt cgtgatgaat cacggctctt tttaacgtaa tttgtaaaaa    11040
agaaaaaatt gataacaaaa ttgacacatg atataatcaa gttgttccat tacttaatat    11100
aaacaagata aaccgttctg attttgttta tgttaagtaa tcatttcaaa gtaaatattt    11160
cgtggatatt tattttgtga ctttcattgt gaacttatca aatggaaata aatttatgtt    11220 ttctttttatt tgttttttgtc gctttataaa gtgacttctt cttcttcgac tcgctaatag    11280
cgggtctttt ttttgttcat aaaaaagaga gtagacattc gtggtatcta ctctctttgc    11340
atcaagctgc tggtttttatt cccctttcat ttaataggtc acgcatttt tcgattccgt    11400 aatcccttgc gttgtgacct ccattgctgc cttccttcat tgtgaattta tcaaatggaa    11460
ataaatttat attttctttt atttgttttt gtaagactga taatatttca cgtttatttt    11520
ttatgaaatc attttgtgtt tttcttcttt tttcttttctt ctcttttttta atatcagaaa    11580 tctttggtat tgttaataat tctcttgctg ttttttttct gttatcaaaa cattgccatt    11640
cgaaatcatc attatagcaa ccgtattcca ttgttatatc tattggtgat gtttcaaata    11700 atctatctttt aatattattt aaacttaatt ctatgtcttc gtttaaatgt gtaatacg    11760 ctcgtttagg tttcaaagag aaactatcaa atataagggg taattcctta tgttttttta    11820
ttcctagttg cctaaaatca gctaaatctt caacaacatg aaaataattt ataatttctt    11880
ctttacctaa ttttaaaccg tattcccctg cacgttttcc atatttaaag aaatgggatt    11940
ctggtttctt caagaagtta tctaatttct tcattaggta agcttcgttt tcaaattcct    12000
tatcaaatgt ttgataaccc gatgttttaa cttcccatct gtcattagat aatttgtatt    12060
catacactgc cgtatttaaa aataaaccct ctgtaaattc ttctggttct tcaaagatac    12120 ctagaaacttt ataccctta ggactccacc catttgtgtt tatcatttca aattcggata    12180
atacactatc aaaacaatga tccaaataat catatgctgg tctttctgtg ttaggcattt    12240
cgaacttaac acaatctgtt aaaatggaaa ttaccttacc gccatttctt tctatgttta    12300
acgctccttc ttgcactctt attctaccga atgcggttat catagacgat acaatcggat    12360
taaacatata acctacatcg aatccagcga aatatatttc ctgctcacca tcttcatttt    12420
ctgaacaagc atactgttga aaggcttgaa agaactttcc gtatatagca ttcgtaatta    12480
atttaacaat atactcggaa tgatttccta tatctcttag tttcaaacgt agttcccaaa    12540
gtatatcaat tactttacta attggatgta attttccgtc ggtttcgata acaacaactt    12600
caatgatttc tttaataact tcattgtgtt tatctttatc aatttgtgac aaaagaaact    12660
ctacttcttt gtaatgaact gtagtcacaa aattaccaaa acctaaaacg ttacgcctta    12720
tttgatttac agttccttct tctcccttttt gtttaatcat aattgtatgt ctaacatcag    12780
```

-continued

```
gaggtatttc gaattcacaa gttaacataa cgatacgttt taaactaggt ttaggaattt    12840
cagtaaaatc ttttatgtta tcaaagtatt gaaccctgct atttctcaaa tcaggaatac    12900
aataacgcat aattgcggga taactagcac ctatatcagt gtttgctccc cttgctatat    12960
aaccaacttt ttcatgctca attatagctc cttggttagc atcaaaactt aaattgatag    13020
ccttcgctat gatatcaaca tcaatatctt tttcttgcca atcattcata gttgaatcaa    13080
ttgaaaaagt tttcaactca ttttcatcta aaactttagc aatagccgct tcggataatg    13140
tacccgccga ataaaaagaa ttaggaaaac aaccgaaact ttctttaaac atattcatca    13200
cgacataaat taaatcctta gataaaaaag aattatacat gttttccctt aaaatctttt    13260
taacataagt attatcttgt aacttatgat tattttatc taccttttg ttatatccat      13320 tcaaaaataa atcccaatta attttacttt cttttatttc ttcggcatat ttaaggtttg    13380
catttctagc acattcgata ggagtctttt gccaaaatgg tttagaacga aaagtattac    13440
atttactcat cttttttgttt tttataacaa ataattctag attgccattt aaaactttag   13500 ataccctat actttcacca ttgccgatat ctaattctat aatgggaggt tctgtccacg     13560
aaccactttt cttatgaaat tttccgttta tacctttaa aactctttgg aatattttca     13620
cctgttcatc ttgttctaag tattttcttt tcattaataa ctttaaaata aggattgatt    13680
caatttcatt aaagtgacaa ataattttat tattaaaatg acaatcttta atgatatttt     13740
tcagcatgta aataaccgat aaatccatat cctttcgtt ttcccgataa atatagtgat     13800
atccgttttt ctttgtcaca ggattgtacg agcaaaaacc aaataacata atttctccag    13860
tcacttcatc aatttcaaat ttaaatccat ataaccctt aggtttatct gaatataaat     13920
attccgttgg cttcggactt gaaaaagtat gtacattaga tagatgaact tccatctctg    13980
aatattctag cttgtccaat ccttcgacac ctaaaaacga aggatttatt tttttcattt    14040
acataactta cctccttttc aaaaaacata acttacaagc acaattatag cacataaaaa    14100
atgwaatcac gtcatataat tctatattaa gagaaaaaat aaattgaaat cagttaaata    14160
ataattaaat cagtaaaact gaatatgatt ttatgtcaca aataataaga ttaagagagt    14220
gtgacaagtc acaatgaagt tatgctacaa aaatatttcc cgactcataa aaagaattgg    14280
ggttaatcga acaaagtgag attcgtaatt cggctcgag                            14319
```